US010035987B2

(12) United States Patent
Jung et al.

(10) Patent No.: US 10,035,987 B2
(45) Date of Patent: Jul. 31, 2018

(54) MICROORGANISM HAVING ENHANCED ACTIVITY OF ALPHA-KETOGLUTARATE DECARBOXYLASE AND A METHOD OF PRODUCING 1,4-BUTANEDIOL USING THE SAME

(71) Applicant: Samsung Electronics Co., Ltd., Suwon-si, Gyeonggi-do (KR)

(72) Inventors: Yukyung Jung, Hwaseong-si (KR); Jinhwan Park, Suwon-si (KR); Taewook Nam, Seoul (KR); Kwangmyung Cho, Seongnam-si (KR); Hwayoung Cho, Hwaseong-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 0 days.

(21) Appl. No.: 15/308,046

(22) PCT Filed: Sep. 4, 2014

(86) PCT No.: PCT/KR2014/008293
§ 371 (c)(1),
(2) Date: Oct. 31, 2016

(87) PCT Pub. No.: WO2015/167085
PCT Pub. Date: Nov. 5, 2015

(65) Prior Publication Data

US 2017/0051258 A1 Feb. 23, 2017

(30) Foreign Application Priority Data

Apr. 30, 2014 (WO) ................ PCT/KR2014/003843

(51) Int. Cl.
*C12P 7/16* (2006.01)
*C12P 7/18* (2006.01)
*C12P 7/42* (2006.01)
*C12N 9/02* (2006.01)

(52) U.S. Cl.
CPC ............. *C12N 9/0008* (2013.01); *C12P 7/16* (2013.01); *C12P 7/18* (2013.01); *C12P 7/42* (2013.01); *C12Y 102/04002* (2013.01); *Y02E 50/10* (2013.01)

(58) Field of Classification Search
None
See application file for complete search history.

(56) References Cited

U.S. PATENT DOCUMENTS 8,129,169 B2 3/2012 Van Dien et al.
8,377,666 B2 2/2013 Haselbeck et al.
2005/0059124 A1 3/2005 Rieping
(Continued)

FOREIGN PATENT DOCUMENTS

EP 1564297 A1 8/2005
KR 2007-0096348 10/2007

OTHER PUBLICATIONS

Geneseq Accession No. BAS85129, published Oct. 24, 2013.*
(Continued)

*Primary Examiner* — Richard C Ekstrom
(74) *Attorney, Agent, or Firm* — Ledig, Voit & Mayer, Ltd.

(57) ABSTRACT

Provided are a microorganism having an enhanced activity of alpha-ketoglutarate decarboxylase and a method of producing 4-hydroxybutyrate or 1,4-butanediol using the same.

14 Claims, 4 Drawing Sheets

(56) References Cited

U.S. PATENT DOCUMENTS

2007/0289034 A1 12/2007 Korthout et al.
2011/0045575 A1* 2/2011 Van Dien .................. C12P 7/18 435/252.33
2011/0294178 A1* 12/2011 Soucaille ................. C12N 9/88 435/158
2013/0034884 A1* 2/2013 Burgard ................. C12N 15/52 435/126
2013/0217086 A1* 8/2013 Lee ........................... C12P 7/18 435/135
2013/0316416 A1* 11/2013 Stephanopoulos ....... C12P 7/18 435/158
2014/0030779 A1* 1/2014 Pharkya ................. C12N 15/63 435/146
2015/0159184 A1* 6/2015 Ramseier ......... C12Y 101/0107 435/121
2015/0337342 A1* 11/2015 Zhang .................... C12N 15/52 435/110
2015/0368677 A1* 12/2015 Furutani .............. C12N 9/0006 435/158
2016/0031778 A1* 2/2016 Garikipati .............. B01D 3/143 435/158
2017/0016035 A1* 1/2017 Ramseier .................. C12P 7/18
2017/0088840 A1* 3/2017 Burk ...................... C12N 15/52

OTHER PUBLICATIONS

Genseq Accession No. ARV28182, published Jul. 10, 2008.*
Geneseq Accession No. ABU28558, published Jun. 15, 2007.*
Geneseq Accession No. ATN16251, published Nov. 27, 2008.*
Geneseq Accession No. AYL57273, published Jan. 6, 2011.*
Green et al., "Catabolism of α-Ketoglutarate by a sucA Mutant of *Bradyrhizobium japonicum*: Evidence for an Alternative Tricarboxylic Acid Cycle", *Journal of Bacteriology*, 182(10): 2838-2844 (2000).
Holz et al., "Overexpression of alpha-ketoglutarate dehydrogenase in *Yarrowia lipolytica* and its effect on production of organic acids", *Appl. Microbiol. Biotechnol.*, 89(5): 1519-1526 (2010).
WIPO, PCT International Search Report in PCT/KR2014/008293 dated Jan. 28, 2015, 3 pages.

* cited by examiner

SEQUENCE LISTING

```
<160> NUMBER OF SEQ ID NOS: 94

<210> SEQ ID NO 1
<211> LENGTH: 933
<212> TYPE: PRT
<213> ORGANISM: Escherichia coli

<400> SEQUENCE: 1

Met Gln Asn Ser Ala Leu Lys Ala Trp Leu Asp Ser Ser Tyr Leu Ser
1               5                   10                  15

Gly Ala Asn Gln Ser Trp Ile Glu Gln Leu Tyr Glu Asp Phe Leu Thr
            20                  25                  30

Asp Pro Asp Ser Val Asp Ala Asn Trp Arg Ser Thr Phe Gln Gln Leu
        35                  40                  45

Pro Gly Thr Gly Val Lys Pro Asp Gln Phe His Ser Gln Thr Arg Glu
    50                  55                  60

Tyr Phe Arg Arg Leu Ala Lys Asp Ala Ser Arg Tyr Ser Ser Thr Ile
65                  70                  75                  80

Ser Asp Pro Asp Thr Asn Val Lys Gln Val Lys Val Leu Gln Leu Ile
                85                  90                  95

Asn Ala Tyr Arg Phe Arg Gly His Gln His Ala Asn Leu Asp Pro Leu
            100                 105                 110

Gly Leu Trp Gln Gln Asp Lys Val Ala Asp Leu Asp Pro Ser Phe His
        115                 120                 125

Asp Leu Thr Glu Ala Asp Phe Gln Glu Thr Phe Asn Val Gly Ser Phe
    130                 135                 140

Ala Ser Gly Lys Glu Thr Met Lys Leu Gly Glu Leu Leu Glu Ala Leu
145                 150                 155                 160

Lys Gln Thr Tyr Cys Gly Pro Ile Gly Ala Glu Tyr Met His Ile Thr
                165                 170                 175

Ser Thr Glu Glu Lys Arg Trp Ile Gln Gln Arg Ile Glu Ser Gly Arg
            180                 185                 190

Ala Thr Phe Asn Ser Glu Glu Lys Lys Arg Phe Leu Ser Glu Leu Thr
        195                 200                 205

Ala Ala Glu Gly Leu Glu Arg Tyr Leu Gly Ala Lys Phe Pro Gly Ala
    210                 215                 220

Lys Arg Phe Ser Leu Glu Gly Gly Asp Ala Leu Ile Pro Met Leu Lys
225                 230                 235                 240

Glu Met Ile Arg His Ala Gly Asn Ser Gly Thr Arg Glu Val Val Leu
                245                 250                 255

Gly Met Ala His Arg Gly Arg Leu Asn Val Leu Val Asn Val Leu Gly
            260                 265                 270

Lys Lys Pro Gln Asp Leu Phe Asp Glu Phe Ala Gly Lys His Lys Glu
        275                 280                 285

His Leu Gly Thr Gly Asp Val Lys Tyr His Met Gly Phe Ser Ser Asp
    290                 295                 300

Phe Gln Thr Asp Gly Gly Leu Val His Leu Ala Leu Ala Phe Asn Pro
305                 310                 315                 320

Ser His Leu Glu Ile Val Ser Pro Val Val Ile Gly Ser Val Arg Ala
                325                 330                 335

Arg Leu Asp Arg Leu Asp Glu Pro Ser Ser Asn Lys Val Leu Pro Ile
```

```
            340                 345                 350

Thr Ile His Gly Asp Ala Ala Val Thr Gly Gln Gly Val Val Gln Glu
        355                 360                 365

Thr Leu Asn Met Ser Lys Ala Arg Gly Tyr Glu Val Gly Gly Thr Val
    370                 375                 380

Arg Ile Val Ile Asn Asn Gln Val Gly Phe Thr Thr Ser Asn Pro Leu
385                 390                 395                 400

Asp Ala Arg Ser Thr Pro Tyr Cys Thr Asp Ile Gly Lys Met Val Gln
                405                 410                 415

Ala Pro Ile Phe His Val Asn Ala Asp Asp Pro Glu Ala Val Ala Phe
            420                 425                 430

Val Thr Arg Leu Ala Leu Asp Phe Arg Asn Thr Phe Lys Arg Asp Val
        435                 440                 445

Phe Ile Asp Leu Val Cys Tyr Arg Arg His Gly His Asn Glu Ala Asp
    450                 455                 460

Glu Pro Ser Ala Thr Gln Pro Leu Met Tyr Gln Lys Ile Lys Lys His
465                 470                 475                 480

Pro Thr Pro Arg Lys Ile Tyr Ala Asp Lys Leu Glu Gln Glu Lys Val
                485                 490                 495

Ala Thr Leu Glu Asp Ala Thr Glu Met Val Asn Leu Tyr Arg Asp Ala
            500                 505                 510

Leu Asp Ala Gly Asp Cys Val Val Ala Glu Trp Arg Pro Met Asn Met
        515                 520                 525

His Ser Phe Thr Trp Ser Pro Tyr Leu Asn His Glu Trp Asp Glu Glu
    530                 535                 540

Tyr Pro Asn Lys Val Glu Met Lys Arg Leu Gln Glu Leu Ala Lys Arg
545                 550                 555                 560

Ile Ser Thr Val Pro Glu Ala Val Glu Met Gln Ser Arg Val Ala Lys
                565                 570                 575

Ile Tyr Gly Asp Arg Gln Ala Met Ala Ala Gly Glu Lys Leu Phe Asp
            580                 585                 590

Trp Gly Gly Ala Glu Asn Leu Ala Tyr Ala Thr Leu Val Asp Glu Gly
        595                 600                 605

Ile Pro Val Arg Leu Ser Gly Glu Asp Ser Gly Arg Gly Thr Phe Phe
    610                 615                 620

His Arg His Ala Val Ile His Asn Gln Ser Asn Gly Ser Thr Tyr Thr
625                 630                 635                 640

Pro Leu Gln His Ile His Asn Gly Gln Gly Ala Phe Arg Val Trp Asp
                645                 650                 655

Ser Val Leu Ser Glu Glu Ala Val Leu Ala Phe Glu Tyr Gly Tyr Ala
            660                 665                 670

Thr Ala Glu Pro Arg Thr Leu Thr Ile Trp Glu Ala Gln Phe Gly Asp
        675                 680                 685

Phe Ala Asn Gly Ala Gln Val Val Ile Asp Gln Phe Ile Ser Ser Gly
    690                 695                 700

Glu Gln Lys Trp Gly Arg Met Cys Gly Leu Val Met Leu Leu Pro His
705                 710                 715                 720

Gly Tyr Glu Gly Gln Gly Pro Glu His Ser Ser Ala Arg Leu Glu Arg
                725                 730                 735

Tyr Leu Gln Leu Cys Ala Glu Gln Asn Met Gln Val Cys Val Pro Ser
            740                 745                 750

Thr Pro Ala Gln Val Tyr His Met Leu Arg Arg Gln Ala Leu Arg Gly
        755                 760                 765
```

```
Met Arg Arg Pro Leu Val Val Met Ser Pro Lys Ser Leu Leu Arg His
    770                 775                 780

Pro Leu Ala Val Ser Ser Leu Glu Glu Leu Ala Asn Gly Thr Phe Leu
785                 790                 795                 800

Pro Ala Ile Gly Glu Ile Asp Glu Leu Asp Pro Lys Gly Val Lys Arg
                805                 810                 815

Val Val Met Cys Ser Gly Lys Val Tyr Tyr Asp Leu Leu Glu Gln Arg
            820                 825                 830

Arg Lys Asn Asn Gln His Asp Val Ala Ile Val Arg Ile Glu Gln Leu
        835                 840                 845

Tyr Pro Phe Pro His Lys Ala Met Gln Glu Val Leu Gln Gln Phe Ala
    850                 855                 860

His Val Lys Asp Phe Val Trp Cys Gln Glu Glu Pro Leu Asn Gln Gly
865                 870                 875                 880

Ala Trp Tyr Cys Ser Gln His His Phe Arg Glu Val Ile Pro Phe Gly
                885                 890                 895

Ala Ser Leu Arg Tyr Ala Gly Arg Pro Ala Ser Ala Ser Pro Ala Val
            900                 905                 910

Gly Tyr Met Ser Val His Gln Lys Gln Gln Gln Asp Leu Val Asn Asp
        915                 920                 925

Ala Leu Asn Val Glu
    930


<210> SEQ ID NO 2
<211> LENGTH: 2802
<212> TYPE: DNA
<213> ORGANISM: Escherichia coli

<400> SEQUENCE: 2

atgcagaaca gcgctttgaa agcctggttg gactcttctt acctctctgg cgcaaaccag      60

agctggatag aacagctcta tgaagacttc ttaaccgatc ctgactcggt tgacgctaac     120

tggcgttcga cgttccagca gttacctggt acgggagtca aaccggatca attccactct     180

caaacgcgtg aatatttccg ccgcctggcg aaagacgctt cacgttactc ttcaacgatc     240

tccgaccctg acaccaatgt gaagcaggtt aaagtcctgc agctcattaa cgcataccgc     300

ttccgtggtc accagcatgc gaatctcgat ccgctgggac tgtggcagca agataaagtg     360

gccgatctgg atccgtcttt ccacgatctg accgaagcag acttccagga gaccttcaac     420

gtcggttcat ttgccagcgg caaagaaacc atgaaactcg gcgagctgct ggaagccctc     480

aagcaaacct actgcggccc gattggtgcc gagtatatgc acattaccag caccgaagaa     540

aaacgctgga tccaacagcg tatcgagtct ggtcgcgcga ctttcaatag cgaagagaaa     600

aaacgcttct taagcgaact gaccgccgct gaaggtcttg aacgttacct cggcgcaaaa     660

ttccctggcg caaaacgctt ctcgctggaa ggcggtgacg cgttaatccc gatgcttaaa     720

gagatgatcc gccacgctgg caacagcggc acccgcgaag tggttctcgg gatggcgcac     780

cgtggtcgtc tgaacgtgct ggtgaacgtg ctgggtaaaa aaccgcaaga cttgttcgac     840

gagttcgccg gtaaacataa agaacacctc ggcacgggtg acgtgaaata ccacatgggc     900

ttctcgtctg acttccagac cgatggcggc ctggtgcacc tggcgctggc gtttaacccg     960

tctcaccttg agattgtaag cccggtagtt atcggttctg ttcgtgcccg tctggacaga    1020

cttgatgagc cgagcagcaa caaagtgctg ccaatcacca tccacggtga cgccgcagtg    1080

accgggcagg gcgtggttca ggaaaccctg aacatgtcga aagcgcgtgg ttatgaagtt    1140
```

```
ggcggtacgg tacgtatcgt tatcaacaac caggttggtt tcaccacctc taatccgctg   1200

gatgcccgtt ctacgccgta ctgtactgat atcggtaaga tggttcaggc cccgattttc   1260

cacgttaacg cggacgatcc ggaagccgtt gcctttgtga cccgtctggc gctcgatttc   1320

cgtaacacct ttaaacgtga tgtcttcatc gacctggtgt gctaccgccg tcacggccac   1380

aacgaagccg acgagccgag cgcaacccag ccgctgatgt atcagaaaat caaaaaacat   1440

ccgacaccgc gcaaaatcta cgctgacaag ctggagcagg aaaaagtggc gacgctggaa   1500

gatgccaccg agatggttaa cctgtaccgc gatgcgctgg atgctggcga ttgcgtagtg   1560

gcagagtggc gtccgatgaa catgcactct ttcacctggt cgccgtacct caaccacgaa   1620

tgggacgaag agtacccgaa caaagttgag atgaagcgcc tgcaggagct ggcgaaacgc   1680

atcagcacgg tgccggaagc agttgaaatg cagtctcgcg ttgccaagat ttatggcgat   1740

cgccaggcga tggctgccgg tgagaaactg ttcgactggg gcggtgcgga aaacctcgct   1800

tacgccacgc tggttgatga aggcattccg gttcgcctgt cgggtgaaga ctccggtcgc   1860

ggtaccttct tccaccgcca cgcggtgatc cacaaccagt ctaacggttc cacttacacg   1920

ccgctgcaac atatccataa cgggcagggc gcgttccgtg tctgggactc cgtactgtct   1980

gaagaagcag tgctggcgtt tgaatatggt tatgccaccg cagaaccacg cactctgacc   2040

atctgggaag cgcagttcgg tgacttcgcc aacggtgcgc aggtggttat cgaccagttc   2100

atctcctctg gcgaacagaa atggggccgg atgtgtggtc tggtgatgtt gctgccgcac   2160

ggttacgaag ggcaggggcc ggagcactcc tccgcgcgtc tggaacgtta tctgcaactt   2220

tgtgctgagc aaaacatgca ggtttgcgta ccgtctaccc cggcacaggt ttaccacatg   2280

ctgcgtcgtc aggcgctgcg cgggatgcgt cgtccgctgg tcgtgatgtc gccgaaatcc   2340

ctgctgcgtc atccgctggc ggtttccagc ctcgaagaac tggcgaacgg caccttcctg   2400

ccagccatcg gtgaaatcga cgagcttgat ccgaagggcg tgaagcgcgt agtgatgtgt   2460

tctggtaagg tttattacga cctgctggaa cagcgtcgta agaacaatca acacgatgtc   2520

gccattgtgc gtatcgagca actctacccg ttcccgcata aagcgatgca ggaagtgttg   2580

cagcagtttg ctcacgtcaa ggattttgtc tggtgccagg aagagccgct caaccagggc   2640

gcatggtact gcagccagca tcatttccgt gaagtgattc cgtttggggc ttctctgcgt   2700

tatgcaggcc gcccggcctc cgcctctccg gcggtagggt atatgtccgt tcaccagaaa   2760

cagcaacaag atctggttaa tgacgcgctg aacgtcgaat aa                      2802
```

```
<210> SEQ ID NO 3
<211> LENGTH: 1221
<212> TYPE: PRT
<213> ORGANISM: Corynebacterium glutamicum

<400> SEQUENCE: 3

Met Ser Ser Ala Ser Thr Phe Gly Gln Asn Ala Trp Leu Val Asp Glu
1               5                   10                  15

Met Phe Gln Gln Phe Gln Lys Asp Pro Lys Ser Val Asp Lys Glu Trp
            20                  25                  30

Arg Glu Leu Phe Glu Ala Gln Gly Gly Pro Asn Thr Thr Pro Ala Thr
        35                  40                  45

Thr Glu Ala Gln Pro Ser Ala Pro Lys Glu Ser Ala Lys Pro Ala Pro
    50                  55                  60

Lys Ala Ala Pro Ala Ala Lys Ala Ala Pro Arg Val Glu Thr Lys Pro
65                  70                  75                  80
```

```
Ala Asp Lys Thr Ala Pro Lys Ala Lys Glu Ser Ser Val Pro Gln Gln
                 85                  90                  95

Pro Lys Leu Pro Glu Pro Gly Gln Thr Pro Ile Arg Gly Ile Phe Lys
            100                 105                 110

Ser Ile Ala Lys Asn Met Asp Ile Ser Leu Glu Ile Pro Thr Ala Thr
        115                 120                 125

Ser Val Arg Asp Met Pro Ala Arg Leu Met Phe Glu Asn Arg Ala Met
    130                 135                 140

Val Asn Asp Gln Leu Lys Arg Thr Arg Gly Gly Lys Ile Ser Phe Thr
145                 150                 155                 160

His Ile Ile Gly Tyr Ala Met Val Lys Ala Val Met Ala His Pro Asp
                165                 170                 175

Met Asn Asn Ser Tyr Asp Val Ile Asp Gly Lys Pro Thr Leu Ile Val
            180                 185                 190

Pro Glu His Ile Asn Leu Gly Leu Ala Ile Asp Leu Pro Gln Lys Asp
        195                 200                 205

Gly Ser Arg Ala Leu Val Val Ala Ala Ile Lys Glu Thr Glu Lys Met
    210                 215                 220

Asn Phe Ser Glu Phe Leu Ala Ala Tyr Glu Asp Ile Val Ala Arg Ser
225                 230                 235                 240

Arg Lys Gly Lys Leu Thr Met Asp Asp Tyr Gln Gly Val Thr Val Ser
                245                 250                 255

Leu Thr Asn Pro Gly Gly Ile Gly Thr Arg His Ser Val Pro Arg Leu
            260                 265                 270

Thr Lys Gly Gln Gly Thr Ile Ile Gly Val Gly Ser Met Asp Tyr Pro
        275                 280                 285

Ala Glu Phe Gln Gly Ala Ser Glu Asp Arg Leu Ala Glu Leu Gly Val
    290                 295                 300

Gly Lys Leu Val Thr Ile Thr Ser Thr Tyr Asp His Arg Val Ile Gln
305                 310                 315                 320

Gly Ala Val Ser Gly Glu Phe Leu Arg Thr Met Ser Arg Leu Leu Thr
                325                 330                 335

Asp Asp Ser Phe Trp Asp Glu Ile Phe Asp Ala Met Asn Val Pro Tyr
            340                 345                 350

Thr Pro Met Arg Trp Ala Gln Asp Val Pro Asn Thr Gly Val Asp Lys
        355                 360                 365

Asn Thr Arg Val Met Gln Leu Ile Glu Ala Tyr Arg Ser Arg Gly His
    370                 375                 380

Leu Ile Ala Asp Thr Asn Pro Leu Ser Trp Val Gln Pro Gly Met Pro
385                 390                 395                 400

Val Pro Asp His Arg Asp Leu Asp Ile Glu Thr His Asn Leu Thr Ile
                 405                 410                 415

Trp Asp Leu Asp Arg Thr Phe Asn Val Gly Gly Phe Gly Gly Lys Glu
            420                 425                 430

Thr Met Thr Leu Arg Glu Val Leu Ser Arg Leu Arg Ala Ala Tyr Thr
        435                 440                 445

Leu Lys Val Gly Ser Glu Tyr Thr His Ile Leu Asp Arg Asp Glu Arg
    450                 455                 460

Thr Trp Leu Gln Asp Arg Leu Glu Ala Gly Met Pro Lys Pro Thr Gln
465                 470                 475                 480

Ala Glu Gln Lys Tyr Ile Leu Gln Lys Leu Asn Ala Ala Glu Ala Phe
                485                 490                 495
```

```
Glu Asn Phe Leu Gln Thr Lys Tyr Val Gly Gln Lys Arg Phe Ser Leu
            500                 505                 510

Glu Gly Ala Glu Ala Leu Ile Pro Leu Met Asp Ser Ala Ile Asp Thr
        515                 520                 525

Ala Ala Gly Gln Gly Leu Asp Glu Val Val Ile Gly Met Pro His Arg
    530                 535                 540

Gly Arg Leu Asn Val Leu Phe Asn Ile Val Gly Lys Pro Leu Ala Ser
545                 550                 555                 560

Ile Phe Asn Glu Phe Glu Gly Gln Met Glu Gln Gly Gln Ile Gly Gly
                565                 570                 575

Ser Gly Asp Val Lys Tyr His Leu Gly Ser Glu Gly Gln His Leu Gln
            580                 585                 590

Met Phe Gly Asp Gly Glu Ile Lys Val Ser Leu Thr Ala Asn Pro Ser
        595                 600                 605

His Leu Glu Ala Val Asn Pro Val Met Glu Gly Ile Val Arg Ala Lys
    610                 615                 620

Gln Asp Tyr Leu Asp Lys Gly Val Asp Gly Lys Thr Val Val Pro Leu
625                 630                 635                 640

Leu Leu His Gly Asp Ala Ala Phe Ala Gly Leu Gly Ile Val Pro Glu
                645                 650                 655

Thr Ile Asn Leu Ala Lys Leu Arg Gly Tyr Asp Val Gly Gly Thr Ile
            660                 665                 670

His Ile Val Val Asn Asn Gln Ile Gly Phe Thr Thr Thr Pro Asp Ser
        675                 680                 685

Ser Arg Ser Met His Tyr Ala Thr Asp Tyr Ala Lys Ala Phe Gly Cys
    690                 695                 700

Pro Val Phe His Val Asn Gly Asp Asp Pro Glu Ala Val Val Trp Val
705                 710                 715                 720

Gly Gln Leu Ala Thr Glu Tyr Arg Arg Arg Phe Gly Lys Asp Val Phe
                725                 730                 735

Ile Asp Leu Val Cys Tyr Arg Leu Arg Gly His Asn Glu Ala Asp Asp
            740                 745                 750

Pro Ser Met Thr Gln Pro Lys Met Tyr Glu Leu Ile Thr Gly Arg Glu
        755                 760                 765

Thr Val Arg Ala Gln Tyr Thr Glu Asp Leu Leu Gly Arg Gly Asp Leu
    770                 775                 780

Ser Asn Glu Asp Ala Glu Ala Val Val Arg Asp Phe His Asp Gln Met
785                 790                 795                 800

Glu Ser Val Phe Asn Glu Val Lys Glu Gly Gly Lys Lys Gln Ala Glu
                805                 810                 815

Ala Gln Thr Gly Ile Thr Gly Ser Gln Lys Leu Pro His Gly Leu Glu
            820                 825                 830

Thr Asn Ile Ser Arg Glu Glu Leu Leu Glu Leu Gly Gln Ala Phe Ala
        835                 840                 845

Asn Thr Pro Glu Gly Phe Asn Tyr His Pro Arg Val Ala Pro Val Ala
    850                 855                 860

Lys Lys Arg Val Ser Ser Val Thr Glu Gly Gly Ile Asp Trp Ala Trp
865                 870                 875                 880

Gly Glu Leu Leu Ala Phe Gly Ser Leu Ala Asn Ser Gly Arg Leu Val
                885                 890                 895

Arg Leu Ala Gly Glu Asp Ser Arg Arg Gly Thr Phe Thr Gln Arg His
            900                 905                 910

Ala Val Ala Ile Asp Pro Ala Thr Ala Glu Glu Phe Asn Pro Leu His
```

```
        915                 920                 925

Glu Leu Ala Gln Ser Lys Gly Asn Asn Gly Lys Phe Leu Val Tyr Asn
    930                 935                 940

Ser Ala Leu Thr Glu Tyr Ala Gly Met Gly Phe Glu Tyr Gly Tyr Ser
945                 950                 955                 960

Val Gly Asn Glu Asp Ser Ile Val Ala Trp Glu Ala Gln Phe Gly Asp
                965                 970                 975

Phe Ala Asn Gly Ala Gln Thr Ile Ile Asp Glu Tyr Val Ser Ser Gly
            980                 985                 990

Glu Ala Lys Trp Gly Gln Thr Ser Lys Leu Ile Leu Leu Leu Pro His
        995                1000                1005

Gly Tyr Glu Gly Gln Gly Pro Asp His Ser Ser Ala Arg Ile Glu Arg
    1010                1015                1020

Phe Leu Gln Leu Cys Ala Glu Gly Ser Met Thr Val Ala Gln Pro Ser
1025               1030                1035                1040

Thr Pro Ala Asn His Phe His Leu Leu Arg Arg His Ala Leu Ser Asp
                1045                1050                1055

Leu Lys Arg Pro Leu Val Ile Phe Thr Pro Lys Ser Met Leu Arg Asn
            1060                1065                1070

Lys Ala Ala Ala Ser Ala Pro Glu Asp Phe Thr Glu Val Thr Lys Phe
        1075                1080                1085

Gln Ser Val Ile Asn Asp Pro Asn Val Ala Asp Ala Ala Lys Val Lys
    1090                1095                1100

Lys Val Met Leu Val Ser Gly Lys Leu Tyr Tyr Glu Leu Ala Lys Arg
1105               1110                1115                1120

Lys Glu Lys Asp Gly Arg Asp Asp Ile Ala Ile Val Arg Ile Glu Met
                1125                1130                1135

Leu His Pro Ile Pro Phe Asn Arg Ile Ser Glu Ala Leu Ala Gly Tyr
            1140                1145                1150

Pro Asn Ala Glu Glu Val Leu Phe Val Gln Asp Glu Pro Ala Asn Gln
        1155                1160                1165

Gly Pro Trp Pro Phe Tyr Gln Glu His Leu Pro Glu Leu Ile Pro Asn
    1170                1175                1180

Met Pro Lys Met Arg Arg Val Ser Arg Arg Ala Gln Ser Ser Thr Ala
1185               1190                1195                1200

Thr Gly Val Ala Lys Val His Gln Leu Glu Glu Lys Gln Leu Ile Asp
                1205                1210                1215

Glu Ala Phe Glu Ala
            1220


<210> SEQ ID NO 4
<211> LENGTH: 3666
<212> TYPE: DNA
<213> ORGANISM: Corynebacterium glutamicum

<400> SEQUENCE: 4

atgagcagcg ctagtacttt cggccagaat gcgtggctgg tagacgagat gttccagcag      60

ttccagaagg accccaagtc cgtggacaag gaatggagag aactctttga ggcgcagggg     120

ggaccaaata ctacccccgc tacaacagaa gcacagcctt cagcgcccaa ggagtctgcg     180

aaaccagcac caaaggctgc ccctgcagcc aaggcagcac cgcgcgtaga aaccaagccg     240

gccgacaaga ccgcccctaa ggccaaggag tcctcagtgc cacagcaacc taagcttccg     300

gagccaggac aaaccccaat caggggtatt ttcaagtcca tcgcgaagaa catggatatc     360
```

```
tccctggaaa tcccaaccgc aacctcggtt cgcgatatgc cagctcgcct catgttcgaa    420

aaccgcgcga tggtcaacga tcagctcaag cgcacccgcg gtggcaagat ctccttcacc    480

cacatcattg gctacgccat ggtgaaggca gtcatggctc acccggacat gaacaactcc    540

tacgacgtca tcgacggcaa gccaaccctg atcgtgcctg agcacatcaa cctgggcctt    600

gctatcgacc ttcctcagaa ggacggctcc cgcgcacttg tcgtagcagc catcaaggaa    660

accgagaaga tgaacttctc cgagttcctc gcagcctacg aagacatcgt ggcacgctcc    720

cgcaagggca agctcaccat ggatgactac cagggcgtta ccgtttcctt gaccaaccca    780

ggtggcatcg gtacccgcca ctctgttcca cgtctaacca agggccaggg caccatcatc    840

ggtgtcggtt ccatggatta cccagcagag ttccagggcg cttcagaaga ccgccttgca    900

gagctcggcg ttggcaaact tgtcaccatc acctccacct acgatcaccg cgtgatccag    960

ggtgctgtgt ccggtgaatt cctgcgcacc atgtctcgcc tgctcaccga tgattccttc   1020

tgggatgaga tcttcgacgc aatgaacgtt ccttacaccc caatgcgttg ggcacaggac   1080

gttccaaaca ccggtgttga taagaacacc cgcgtcatgc agctcattga ggcataccgc   1140

tcccgtggac acctcatcgc tgacaccaac ccactttcat gggttcagcc tggcatgcca   1200

gttccagacc accgcgacct cgacatcgag acccacaacc tgaccatctg ggatctggac   1260

cgtaccttca acgtcggtgg cttcggcggc aaggagacca tgaccctgcg cgaggtactg   1320

tcccgcctcc gcgctgcgta caccctcaag gtcggctccg aatacaccca catcctggac   1380

cgcgacgagc gcacctggct gcaggaccgc ctcgaggccg gaatgccaaa gccaacccag   1440

gcagagcaga agtacatcct gcagaagctg aacgccgcgg aggctttcga gaacttcctg   1500

cagaccaagt acgtcggcca gaagcgcttc tccctcgaag gtgcagaagc acttatccca   1560

ctgatggact ccgccatcga caccgccgca ggccaaggcc tcgacgaagt tgtcatcggt   1620

atgccacacc gtggtcgcct caacgtgctg ttcaacatcg tgggcaagcc actggcatcc   1680

atcttcaacg agtttgaagg ccaaatggag cagggccaga tcggtggctc cggtgacgtg   1740

aagtaccacc tcggttccga aggccagcac ctgcagatgt tcggcgacgg cgagatcaag   1800

gtctccctga ctgctaaccc gtcccacctg gaagctgtta acccagtgat ggaaggtatc   1860

gtccgcgcaa agcaggacta cctggacaag ggcgtagacg gcaagactgt tgtgccactg   1920

ctgctccacg gtgacgctgc attcgcaggc ctgggcatcg tgccagaaac catcaacctg   1980

gctaagctgc gtggctacga cgtcggcggc accatccaca tcgtggtgaa caaccagatc   2040

ggcttcacca ccaccccaga ctccagccgc tccatgcact acgcaaccga ctacgccaag   2100

gcattcggct gcccagtctt ccacgtcaac ggcgacgacc cagaggcagt tgtctgggtt   2160

ggccagctgg ccaccgagta ccgtcgtcgc ttcggcaagg acgtcttcat cgacctcgtc   2220

tgctaccgcc tccgcggcca caacgaagct gatgatcctt ccatgaccca gccaaagatg   2280

tatgagctca tcaccggccg cgagaccgtt cgtgctcagt acaccgaaga cctgctcgga   2340

cgtggagacc tctccaacga agatgcagaa gcagtcgtcc gcgacttcca cgaccagatg   2400

gaatctgtgt tcaacgaagt caaggaaggc ggcaagaagc aggctgaggc acagaccggc   2460

atcaccggct cccagaagct tccacacggc cttgagacca acatctcccg tgaagagctc   2520

ctggaactgg gacaggcttt cgccaacacc ccagaaggct tcaactacca cccacgtgtg   2580

gctcccgttg ctaagaagcg cgtctcctct gtcaccgaag gtggcatcga ctgggcatgg   2640

ggcgagctcc tcgccttcgg ttccctggct aactccggcc gcttggttcg ccttgcaggt   2700

gaagattccc gccgcggtac cttcacccag cgccacgcag ttgccatcga cccagcgacc   2760
```

```
gctgaagagt tcaacccact ccacgagctt gcacagtcca agggcaacaa cggtaagttc   2820

ctggtctaca actccgcact gaccgagtac gcaggcatgg gcttcgagta cggctactcc   2880

gtaggaaacg aagactccat cgttgcatgg gaagcacagt tcggcgactt cgccaacggc   2940

gctcagacca tcatcgatga gtacgtctcc tcaggcgaag ctaagtgggg ccagacctcc   3000

aagctgatcc ttctgctgcc tcacggctac gaaggccagg gcccagacca ctcttccgca   3060

cgtatcgagc gcttcctgca gctgtgcgct gagggttcca tgactgttgc tcagccatcc   3120

accccagcaa accacttcca cctactgcgt cgtcacgctc tgtccgacct gaagcgtcca   3180

ctggttatct tcaccccgaa gtccatgctg cgtaacaagg ctgctgcctc cgcaccagaa   3240

gacttcactg aggtcaccaa gttccagtcc gtgatcaacg atccaaacgt tgcagatgca   3300

gccaaggtga agaaggtcat gctggtctcc ggcaagctgt actacgaatt ggcaaagcgc   3360

aaggagaagg acggacgcga cgacatcgcg atcgttcgta tcgaaatgct ccacccaatt   3420

ccgttcaacc gcatctccga ggctcttgcc ggctacccta acgctgagga agtcctcttc   3480

gttcaggatg agccagcaaa ccagggccca tggccgttct accaggagca cctcccagag   3540

ctgatcccga acatgccaaa gatgcgccgc gtttcccgcc gcgctcagtc ctccaccgca   3600

actggtgttg ccaaggtgca ccagctggag gagaagcagc ttatcgacga ggctttcgag   3660

gcttaa                                                              3666
```

<210> SEQ ID NO 5
<211> LENGTH: 371
<212> TYPE: PRT
<213> ORGANISM: Porphyromonas gingivalis

<400> SEQUENCE: 5

```
Met Gln Leu Phe Lys Leu Lys Ser Val Thr His His Phe Asp Thr Phe
 1               5                  10                  15

Ala Glu Phe Ala Lys Glu Phe Cys Leu Gly Glu Arg Asp Leu Val Ile
            20                  25                  30

Thr Asn Glu Phe Ile Tyr Glu Pro Tyr Met Lys Ala Cys Gln Leu Pro
        35                  40                  45

Cys His Phe Val Met Gln Glu Lys Tyr Gly Gln Gly Glu Pro Ser Asp
    50                  55                  60

Glu Met Met Asn Asn Ile Leu Ala Asp Ile Arg Asn Ile Gln Phe Asp
65                  70                  75                  80

Arg Val Ile Gly Ile Gly Gly Gly Thr Val Ile Asp Ile Ser Lys Leu
                85                  90                  95

Phe Val Leu Lys Gly Leu Asn Asp Val Leu Asp Ala Phe Asp Arg Lys
            100                 105                 110

Ile Pro Leu Ile Lys Glu Lys Glu Leu Ile Ile Val Pro Thr Thr Cys
        115                 120                 125

Gly Thr Gly Ser Glu Val Thr Asn Ile Ser Ile Ala Glu Ile Lys Ser
    130                 135                 140

Arg His Thr Lys Met Gly Leu Ala Asp Asp Ala Ile Val Ala Asp His
145                 150                 155                 160

Ala Ile Ile Ile Pro Glu Leu Leu Lys Ser Leu Pro Phe His Phe Tyr
                165                 170                 175

Ala Cys Ser Ala Ile Asp Ala Leu Ile His Ala Ile Glu Ser Tyr Val
            180                 185                 190

Ser Pro Lys Ala Ser Pro Tyr Ser Arg Leu Phe Ser Glu Ala Ala Trp
        195                 200                 205
```

```
Asp Ile Ile Leu Glu Val Phe Lys Lys Ile Ala Glu His Gly Pro Glu
    210                 215                 220

Tyr Arg Phe Glu Lys Leu Gly Glu Met Ile Met Ala Ser Asn Tyr Ala
225                 230                 235                 240

Gly Ile Ala Phe Gly Asn Ala Gly Val Gly Ala Val His Ala Leu Ser
                245                 250                 255

Tyr Pro Leu Gly Gly Asn Tyr His Val Pro His Gly Glu Ala Asn Tyr
            260                 265                 270

Gln Phe Phe Thr Glu Val Phe Lys Val Tyr Gln Lys Lys Asn Pro Phe
        275                 280                 285

Gly Tyr Ile Val Glu Leu Asn Trp Lys Leu Ser Lys Ile Leu Asn Cys
    290                 295                 300

Gln Pro Glu Tyr Val Tyr Pro Lys Leu Asp Glu Leu Leu Gly Cys Leu
305                 310                 315                 320

Leu Thr Lys Lys Pro Leu His Glu Tyr Gly Met Lys Asp Glu Glu Val
                325                 330                 335

Arg Gly Phe Ala Glu Ser Val Leu Lys Thr Gln Gln Arg Leu Leu Ala
            340                 345                 350

Asn Asn Tyr Val Glu Leu Thr Val Asp Glu Ile Glu Gly Ile Tyr Arg
        355                 360                 365

Arg Leu Tyr
    370


<210> SEQ ID NO 6
<211> LENGTH: 1116
<212> TYPE: DNA
<213> ORGANISM: Porphyromonas gingivalis

<400> SEQUENCE: 6

atgcaactgt tcaaactgaa atcagtcaca catcacttcg atactttcgc ggaatttgcc      60

aaagagttct gtcttggaga acgtgattta gtaattacca acgaattcat ttacgaaccg     120

tatatgaagg catgtcagtt gccctgccat tttgttatgc aggagaaata tgggcaaggc     180

gagccatctg acgagatgat gaataacatc ttggcagaca tccgtaatat ccagtttgac     240

cgcgtgatcg gtattggggg tggtacggtt attgacatct cgaaattatt tgtgctgaaa     300

ggactaaatg atgtgctcga tgcgttcgat cgcaagatac cgctgattaa agagaaagaa     360

ctgatcattg tgcccaccac atgcgggacg ggtagcgagg tgacgaatat ttcgatcgcg     420

gagatcaaaa gccgtcatac caaaatgggt ttggctgacg atgctattgt tgcagaccac     480

gcgatcatca taccagagct tctgaaaagc ctgccgttcc atttttatgc atgcagtgca     540

atagatgctc tgatccatgc catcgagtca tatgtttctc ctaaagccag tccatattct     600

cgtctgttca gtgaggcggc atgggatatt atcctggagg tattcaagaa aatagccgaa     660

cacggccctg aataccgctt tgagaagctg ggagaaatga tcatggcctc caactatgct     720

ggtatagcct tcgggaatgc aggcgtgggt gccgttcacg ctctaagcta tccattggga     780

ggcaattatc atgtgccgca tggcgaggct aactatcagt tttttacaga ggtctttaaa     840

gtataccaaa agaaaaatcc tttcggctat atagtcgaac tcaactggaa gctgtccaag     900

attctgaact gtcagcctga atacgtctat ccgaaactgg atgagttact cggctgtctt     960

ctgaccaaaa aaccgctgca cgaatacggc atgaaagatg aagaggtacg tggatttgcg    1020

gaatcagtgc ttaagactca gcagcggttg ctcgcgaata attatgttga gcttactgtt    1080

gatgaaattg aaggtatcta cagacgactg tactaa                              1116
```

<210> SEQ ID NO 7
<211> LENGTH: 431
<212> TYPE: PRT
<213> ORGANISM: Porphyromonas gingivalis

<400> SEQUENCE: 7

```
Met Lys Asp Val Leu Ala Glu Tyr Ala Ser Arg Ile Val Ser Ala Glu
  1               5                  10                  15

Glu Ala Val Lys His Ile Lys Asn Gly Glu Arg Val Ala Leu Ser His
             20                  25                  30

Ala Ala Gly Val Pro Gln Ser Cys Val Asp Ala Leu Val Gln Gln Ala
         35                  40                  45

Asp Leu Phe Gln Asn Val Glu Ile Tyr His Met Leu Cys Leu Gly Glu
     50                  55                  60

Gly Lys Tyr Met Ala Pro Glu Met Ala Pro His Phe Arg His Ile Thr
 65                  70                  75                  80

Asn Phe Val Gly Gly Asn Ser Arg Lys Ala Val Glu Glu Asn Arg Ala
                 85                  90                  95

Asp Phe Ile Pro Val Phe Phe Tyr Glu Val Pro Ser Met Ile Arg Lys
            100                 105                 110

Asp Ile Leu His Ile Asp Val Ala Ile Val Gln Leu Ser Met Pro Asp
        115                 120                 125

Glu Asn Gly Tyr Cys Ser Phe Gly Val Ser Cys Asp Tyr Ser Lys Pro
    130                 135                 140

Ala Ala Glu Ser Ala His Leu Val Ile Gly Glu Ile Asn Arg Gln Met
145                 150                 155                 160

Pro Tyr Val His Gly Asp Asn Leu Ile His Ile Ser Lys Leu Asp Tyr
                165                 170                 175

Ile Val Met Ala Asp Tyr Pro Ile Tyr Ser Leu Ala Lys Pro Lys Ile
            180                 185                 190

Gly Glu Val Glu Glu Ala Ile Gly Arg Asn Cys Ala Glu Leu Ile Glu
        195                 200                 205

Asp Gly Ala Thr Leu Gln Leu Gly Ile Gly Ala Ile Pro Asp Ala Ala
    210                 215                 220

Leu Leu Phe Leu Lys Asp Lys Lys Asp Leu Gly Ile His Thr Glu Met
225                 230                 235                 240

Phe Ser Asp Gly Val Val Glu Leu Val Arg Ser Gly Val Ile Thr Gly
                245                 250                 255

Lys Lys Lys Thr Leu His Pro Gly Lys Met Val Ala Thr Phe Leu Met
            260                 265                 270

Gly Ser Glu Asp Val Tyr His Phe Ile Asp Lys Asn Pro Asp Val Glu
        275                 280                 285

Leu Tyr Pro Val Asp Tyr Val Asn Asp Pro Arg Val Ile Ala Gln Asn
    290                 295                 300

Asp Asn Met Val Ser Ile Asn Ser Cys Ile Glu Ile Asp Leu Met Gly
305                 310                 315                 320

Gln Val Val Ser Glu Cys Ile Gly Ser Lys Gln Phe Ser Gly Thr Gly
                325                 330                 335

Gly Gln Val Asp Tyr Val Arg Gly Ala Ala Trp Ser Lys Asn Gly Lys
            340                 345                 350

Ser Ile Met Ala Ile Pro Ser Thr Ala Lys Asn Gly Thr Ala Ser Arg
        355                 360                 365

Ile Val Pro Ile Ile Ala Glu Gly Ala Ala Val Thr Thr Leu Arg Asn
```

```
    370                 375                 380

Glu Val Asp Tyr Val Val Thr Glu Tyr Gly Ile Ala Gln Leu Lys Gly
385                 390                 395                 400

Lys Ser Leu Arg Gln Arg Ala Glu Ala Leu Ile Ala Ile Ala His Pro
                405                 410                 415

Asp Phe Arg Glu Glu Leu Thr Lys His Leu Arg Lys Arg Phe Gly
            420                 425                 430


<210> SEQ ID NO 8
<211> LENGTH: 1296
<212> TYPE: DNA
<213> ORGANISM: Porphyromonas gingivalis

<400> SEQUENCE: 8

atgaaagacg tgttagcgga atatgcctcc cgaattgttt cggccgaaga ggcagtcaaa      60

catatcaaaa atggagagcg tgtcgcttta tcacatgctg ccggagttcc tcagagttgt     120

gttgacgcac tggtgcaaca ggcggacctg tttcagaatg tggagattta ccacatgctg     180

tgtctcggcg aaggaaaata tatggcacct gaaatggccc ctcacttccg gcacataacc     240

aattttgttg gtggtaactc tcgtaaagca gtggaggaaa atagagccga cttcattccg     300

gtattctttt atgaagtgcc atcaatgatt cggaaagata tccttcatat agatgtggcc     360

attgtccaac tctcaatgcc agatgagaat ggttactgca gctttggcgt atcttgcgat     420

tatagcaaac cggcggcgga atcggcgcat ttagttattg gggaaatcaa ccgtcagatg     480

ccatatgtgc atggtgacaa cttgattcac atatcgaagt tggattacat cgtgatggcg     540

gattacccaa tttattctct ggcgaagccc aaaatcggag aagtagagga agctatcggc     600

cgtaactgtg ccgagcttat tgaagatggt gccaccctac agctgggtat cggcgcgatt     660

ccggatgcag ctctgctgtt tctgaaggac aaaaaagatc tggggattca tactgaaatg     720

ttctccgatg gcgttgttga actggtgcgc agtggtgtaa ttactggaaa aaaaaagaca     780

ttgcatcccg gtaagatggt cgcgacgttt cttatgggat cagaagacgt gtatcatttc     840

atcgacaaga atccggatgt ggaactgtat ccggttgatt acgtcaatga tccgagggtt     900

atcgctcaga atgataatat ggtcagcatc aatagctgta tcgagatcga tctaatgggc     960

caagtggtga gcgagtgcat aggctccaaa cagtttagtg gcaccggggg tcaagtagat    1020

tatgtccgcg gggcagcttg gtctaaaaac ggcaaaagca tcatggcaat tccctcaaca    1080

gccaaaaacg gtactgcatc tcggatagtt cctataattg cagagggcgc tgctgtaaca    1140

accctccgca acgaagtcga ctacgttgtt acggaatatg ggatagcaca gttaaaaggt    1200

aagagtttgc gtcagcgcgc agaagctctt attgcgatag cccacccgga ctttagagag    1260

gaactgacga agcatctgcg caaacgtttt ggttaa                              1296


<210> SEQ ID NO 9
<211> LENGTH: 468
<212> TYPE: PRT
<213> ORGANISM: Clostridium saccharoperbutylacetonicum

<400> SEQUENCE: 9

Met Ile Lys Asp Thr Leu Val Ser Ile Thr Lys Asp Leu Lys Leu Lys
  1               5                  10                  15

Thr Asn Val Glu Asn Ala Asn Leu Lys Asn Tyr Lys Asp Asp Ser Ser
             20                  25                  30

Cys Phe Gly Val Phe Glu Asn Val Glu Asn Ala Ile Ser Asn Ala Val
         35                  40                  45
```

```
His Ala Gln Lys Ile Leu Ser Leu His Tyr Thr Lys Glu Gln Arg Glu
     50                  55                  60

Lys Ile Ile Thr Glu Ile Arg Lys Ala Ala Leu Glu Asn Lys Glu Ile
 65                  70                  75                  80

Leu Ala Thr Met Ile Leu Glu Glu Thr His Met Gly Arg Tyr Glu Asp
                 85                  90                  95

Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
        115                 120                 125

Glu Met Ser Pro Tyr Gly Val Ile Gly Ala Ile Thr Pro Ser Thr Asn
    130                 135                 140

Pro Thr Glu Thr Val Ile Cys Asn Ser Ile Gly Met Ile Ala Ala Gly
145                 150                 155                 160

Asn Thr Val Val Phe Asn Gly His Pro Gly Ala Lys Lys Cys Val Ala
                165                 170                 175

Phe Ala Val Glu Met Ile Asn Lys Ala Ile Ile Ser Cys Gly Gly Pro
            180                 185                 190

Glu Asn Leu Val Thr Thr Ile Lys Asn Pro Thr Met Asp Ser Leu Asp
        195                 200                 205

Ala Ile Ile Lys His Pro Ser Ile Lys Leu Leu Cys Gly Thr Gly Gly
    210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Lys Ser Ile Ile Glu Gly Cys Ser Phe Asp Asn Asn
            260                 265                 270

Leu Pro Cys Ile Ala Glu Lys Glu Val Phe Val Phe Glu Asn Val Ala
        275                 280                 285

Asp Asp Leu Ile Ser Asn Met Leu Lys Asn Asn Ala Val Ile Ile Asn
    290                 295                 300

Glu Asp Gln Val Ser Lys Leu Ile Asp Leu Val Leu Gln Lys Asn Asn
305                 310                 315                 320

Glu Thr Gln Glu Tyr Ser Ile Asn Lys Lys Trp Val Gly Lys Asp Ala
                325                 330                 335

Lys Leu Phe Leu Asp Glu Ile Asp Val Glu Ser Pro Ser Ser Val Lys
            340                 345                 350

Cys Ile Ile Cys Glu Val Ser Ala Arg His Pro Phe Val Met Thr Glu
        355                 360                 365

Leu Met Met Pro Ile Leu Pro Ile Val Arg Val Lys Asp Ile Asp Glu
    370                 375                 380

Ala Ile Glu Tyr Ala Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415

Ile Asp Thr Thr Ile Phe Val Lys Asn Ala Lys Ser Phe Ala Gly Val
            420                 425                 430

Gly Tyr Glu Ala Glu Gly Phe Thr Thr Phe Thr Ile Ala Gly Ser Thr
        435                 440                 445

Gly Glu Gly Ile Thr Ser Ala Arg Asn Phe Thr Arg Gln Arg Arg Cys
    450                 455                 460
```

Val Leu Ala Gly
465

<210> SEQ ID NO 10
<211> LENGTH: 1407
<212> TYPE: DNA
<213> ORGANISM: Clostridium saccharoperbutylacetonicum

<400> SEQUENCE: 10

```
atgattaaag acacgctagt ttctataaca aaagatttaa aattaaaaac aaatgttgaa      60

aatgccaatc taaagaacta caaggatgat tcttcatgtt tcggagtttt cgaaaatgtt     120

gaaaatgcta taagcaatgc cgtacacgca caaaagatat tatcccttca ttatacaaaa     180

gaacaaagag aaaaaatcat aactgagata agaaaggccg cattagaaaa taaagagatt     240

ctagctacaa tgattcttga agaaacacat atgggaagat atgaagataa aatattaaag     300

catgaattag tagctaaata cactcctggg acagaagatt taactactac tgcttggtca     360

ggagataacg ggcttacagt tgtagaaatg tctccatatg gcgttatagg tgcaataact     420

ccttctacga atccaactga aactgtaata tgtaatagta taggcatgat agctgctgga     480

aatactgtgg tatttaacgg acatccaggc gctaaaaaat gtgttgcttt tgctgtcgaa     540

atgataaata aagctattat ttcatgtggt ggtcctgaga atttagtaac aactataaaa     600

aatccaacta tggactctct agatgcaatt attaagcacc cttcaataaa actactttgc     660

ggaactggag ggccaggaat ggtaaaaacc ctcttaaatt ctggtaagaa agctataggt     720

gctggtgctg gaaatccacc agttattgta gatgatactg ctgatataga aaaggctggt     780

aagagtatca ttgaaggctg ttcttttgat aataatttac cttgtattgc agaaaaagaa     840

gtatttgttt ttgagaacgt tgcagatgat ttaatatcta acatgctaaa aaataatgct     900

gtaattataa atgaagatca agtatcaaag ttaatagatt tagtattaca aaaaaataat     960

gaaactcaag aatactctat aaataagaaa tgggtcggaa aagatgcaaa attattctta    1020

gatgaaatag atgttgagtc tccttcaagt gttaaatgca taatctgcga agtaagtgca    1080

aggcatccat ttgttatgac agaactcatg atgccaatat taccaattgt aagagttaaa    1140

gatatagatg aagctattga atatgcaaaa atagcagaac aaaatagaaa acatagtgcc    1200

tatatttatt caaaaaatat agacaaccta aataggtttg aaagagaaat cgatactact    1260

atctttgtaa agaatgctaa atcttttgcc ggtgttggtt atgaagcaga aggctttaca    1320

actttcacta ttgctggatc cactggtgaa ggaataactt ctgcaagaaa ttttacaaga    1380

caaagaagat gtgtactcgc cggttaa                                        1407
```

<210> SEQ ID NO 11
<211> LENGTH: 858
<212> TYPE: PRT
<213> ORGANISM: Clostridium acetobutylicum

<400> SEQUENCE: 11

```
Met Lys Val Thr Asn Gln Lys Glu Leu Lys Gln Lys Leu Asn Glu Leu
  1               5                  10                  15

Arg Glu Ala Gln Lys Lys Phe Ala Thr Tyr Thr Gln Glu Gln Val Asp
             20                  25                  30

Lys Ile Phe Lys Gln Cys Ala Ile Ala Ala Ala Lys Glu Arg Ile Asn
         35                  40                  45

Leu Ala Lys Leu Ala Val Glu Glu Thr Gly Ile Gly Leu Val Glu Asp
     50                  55                  60
```

```
Lys Ile Ile Lys Asn His Phe Ala Ala Glu Tyr Ile Tyr Asn Lys Tyr
 65                 70                  75                  80

Lys Asn Glu Lys Thr Cys Gly Ile Ile Asp His Asp Asp Ser Leu Gly
                85                  90                  95

Ile Thr Lys Val Ala Glu Pro Ile Gly Ile Val Ala Ala Ile Val Pro
            100                 105                 110

Thr Thr Asn Pro Thr Ser Thr Ala Ile Phe Lys Ser Leu Ile Ser Leu
        115                 120                 125

Lys Thr Arg Asn Ala Ile Phe Phe Ser Pro His Pro Arg Ala Lys Lys
    130                 135                 140

Ser Thr Ile Ala Ala Ala Lys Leu Ile Leu Asp Ala Ala Val Lys Ala
145                 150                 155                 160

Gly Ala Pro Lys Asn Ile Ile Gly Trp Ile Asp Glu Pro Ser Ile Glu
                165                 170                 175

Leu Ser Gln Asp Leu Met Ser Glu Ala Asp Ile Ile Leu Ala Thr Gly
            180                 185                 190

Gly Pro Ser Met Val Lys Ala Ala Tyr Ser Ser Gly Lys Pro Ala Ile
        195                 200                 205

Gly Val Gly Ala Gly Asn Thr Pro Ala Ile Ile Asp Glu Ser Ala Asp
    210                 215                 220

Ile Asp Met Ala Val Ser Ser Ile Ile Leu Ser Lys Thr Tyr Asp Asn
225                 230                 235                 240

Gly Val Ile Cys Ala Ser Glu Gln Ser Ile Leu Val Met Asn Ser Ile
                245                 250                 255

Tyr Glu Lys Val Lys Glu Glu Phe Val Lys Arg Gly Ser Tyr Ile Leu
            260                 265                 270

Asn Gln Asn Glu Ile Ala Lys Ile Lys Glu Thr Met Phe Lys Asn Gly
        275                 280                 285

Ala Ile Asn Ala Asp Ile Val Gly Lys Ser Ala Tyr Ile Ile Ala Lys
    290                 295                 300

Met Ala Gly Ile Glu Val Pro Gln Thr Thr Lys Ile Leu Ile Gly Glu
305                 310                 315                 320

Val Gln Ser Val Glu Lys Ser Glu Leu Phe Ser His Glu Lys Leu Ser
                325                 330                 335

Pro Val Leu Ala Met Tyr Lys Val Lys Asp Phe Asp Glu Ala Leu Lys
            340                 345                 350

Lys Ala Gln Arg Leu Ile Glu Leu Gly Gly Ser Gly His Thr Ser Ser
        355                 360                 365

Leu Tyr Ile Asp Ser Gln Asn Asn Lys Asp Lys Val Lys Glu Phe Gly
    370                 375                 380

Leu Ala Met Lys Thr Ser Arg Thr Phe Ile Asn Met Pro Ser Ser Gln
385                 390                 395                 400

Gly Ala Ser Gly Asp Leu Tyr Asn Phe Ala Ile Ala Pro Ser Phe Thr
                405                 410                 415

Leu Gly Cys Gly Thr Trp Gly Gly Asn Ser Val Ser Gln Asn Val Glu
            420                 425                 430

Pro Lys His Leu Leu Asn Ile Lys Ser Val Ala Glu Arg Arg Glu Asn
        435                 440                 445

Met Leu Trp Phe Lys Val Pro Gln Lys Ile Tyr Phe Lys Tyr Gly Cys
    450                 455                 460

Leu Arg Phe Ala Leu Lys Glu Leu Lys Asp Met Asn Lys Lys Arg Ala
465                 470                 475                 480

Phe Ile Val Thr Asp Lys Asp Leu Phe Lys Leu Gly Tyr Val Asn Lys
```

```
                485                 490                 495

Ile Thr Lys Val Leu Asp Glu Ile Asp Ile Lys Tyr Ser Ile Phe Thr
            500                 505                 510

Asp Ile Lys Ser Asp Pro Thr Ile Asp Ser Val Lys Lys Gly Ala Lys
        515                 520                 525

Glu Met Leu Asn Phe Glu Pro Asp Thr Ile Ile Ser Ile Gly Gly Gly
    530                 535                 540

Ser Pro Met Asp Ala Ala Lys Val Met His Leu Leu Tyr Glu Tyr Pro
545                 550                 555                 560

Glu Ala Glu Ile Glu Asn Leu Ala Ile Asn Phe Met Asp Ile Arg Lys
                565                 570                 575

Arg Ile Cys Asn Phe Pro Lys Leu Gly Thr Lys Ala Ile Ser Val Ala
            580                 585                 590

Ile Pro Thr Thr Ala Gly Thr Gly Ser Glu Ala Thr Pro Phe Ala Val
        595                 600                 605

Ile Thr Asn Asp Glu Thr Gly Met Lys Tyr Pro Leu Thr Ser Tyr Glu
    610                 615                 620

Leu Thr Pro Asn Met Ala Ile Ile Asp Thr Glu Leu Met Leu Asn Met
625                 630                 635                 640

Pro Arg Lys Leu Thr Ala Ala Thr Gly Ile Asp Ala Leu Val His Ala
                645                 650                 655

Ile Glu Ala Tyr Val Ser Val Met Ala Thr Asp Tyr Thr Asp Glu Leu
            660                 665                 670

Ala Leu Arg Ala Ile Lys Met Ile Phe Lys Tyr Leu Pro Arg Ala Tyr
        675                 680                 685

Lys Asn Gly Thr Asn Asp Ile Glu Ala Arg Glu Lys Met Ala His Ala
    690                 695                 700

Ser Asn Ile Ala Gly Met Ala Phe Ala Asn Ala Phe Leu Gly Val Cys
705                 710                 715                 720

His Ser Met Ala His Lys Leu Gly Ala Met His His Val Pro His Gly
                725                 730                 735

Ile Ala Cys Ala Val Leu Ile Glu Glu Val Ile Lys Tyr Asn Ala Thr
            740                 745                 750

Asp Cys Pro Thr Lys Gln Thr Ala Phe Pro Gln Tyr Lys Ser Pro Asn
        755                 760                 765

Ala Lys Arg Lys Tyr Ala Glu Ile Ala Glu Tyr Leu Asn Leu Lys Gly
    770                 775                 780

Thr Ser Asp Thr Glu Lys Val Thr Ala Leu Ile Glu Ala Ile Ser Lys
785                 790                 795                 800

Leu Lys Ile Asp Leu Ser Ile Pro Gln Asn Ile Ser Ala Ala Gly Ile
                805                 810                 815

Asn Lys Lys Asp Phe Tyr Asn Thr Leu Asp Lys Met Ser Glu Leu Ala
            820                 825                 830

Phe Asp Asp Gln Cys Thr Thr Ala Asn Pro Arg Tyr Pro Leu Ile Ser
        835                 840                 845

Glu Leu Lys Asp Ile Tyr Ile Lys Ser Phe
    850                 855
```

<210> SEQ ID NO 12
<211> LENGTH: 2577
<212> TYPE: DNA
<213> ORGANISM: Clostridium acetobutylicum

<400> SEQUENCE: 12

```
atgaaagtca ccaaccagaa agagctgaaa cagaaactga acgaactgcg tgaagcccag      60
aagaagttcg ctacgtacac ccaggaacag gtggacaaaa tcttcaaaca gtgcgcgatt     120
gctgctgcaa aagaacgtat caacctggct aaactggccg tggaagagac gggcattggt     180
ctggtggaag acaagatcat caaaaaccac tttgcggcgg aatacatcta caacaagtac     240
aaaaacgaga aaacttgcgg catcatcgac cacgatgatt ccctgggcat caccaaagtg     300
gcagaaccta tcggtattgt tgcagcaatt gtaccgacta ctaacccgac ttctaccgct     360
attttcaagt ctctgatttc tctgaaaacc cgcaacgcga ttttcttctc tccgcaccca     420
cgtgcgaaaa aatccaccat cgctgccgcc aaactgatcc tggacgcggc agttaaagcg     480
ggtgctccga aaaatatcat tggttggatc gatgaaccgt ctatcgaact gagccaggat     540
ctgatgtccg aagcagacat tatcctggca accggcggtc cgtctatggt aaaagccgcc     600
tactcttctg gcaaaccggc aattggtgtt ggtgctggta acacgccggc gattatcgac     660
gagtccgcag acatcgatat ggcagtttcc tctatcattc tgtccaaaac ctacgataac     720
ggcgtgatct gcgcgagcga acagtccatc ctggttatga attctatcta tgaaaaggtc     780
aaggaagaat ttgttaagcg tggcagctac atcctgaacc agaacgagat cgcgaaaatc     840
aaagaaacta tgttcaaaaa cggtgccatc aatgccgaca tcgtcggcaa atctgcttac     900
attattgcca aaatggctgg tatcgaagtg ccgcagacca cgaagatcct gatcggtgag     960
gtacagagcg ttgaaaagtc tgaactgttc tctcatgaaa aactgtcccc ggtcctggct    1020
atgtacaaag taaaagactt cgacgaagca ctgaaaaaag cgcaacgtct gatcgagctg    1080
ggtggtagcg gccacacctc tagcctgtac atcgacagcc agaacaacaa agataaagtt    1140
aaagaattcg gcctggcaat gaaaaccagc cgcaccttta ttaacatgcc ttctagccaa    1200
ggtgcttctg gcgacctgta taacttcgct attgcgcctt cctttaccct gggttgcggt    1260
acctggggcg gtaacagcgt ttcccaaaac gttgaaccga aacacctgct gaacattaaa    1320
tctgtagcag aacgccgtga gaacatgctg tggtttaaag ttccgcagaa aatctacttc    1380
aagtacggtt gtctgcgctt cgctctgaaa gaactgaagg atatgaacaa gaaacgtgcg    1440
ttcatcgtga ctgataaaga tctgttcaaa ctgggctacg ttaacaaaat cactaaagta    1500
ctggacgaaa tcgatattaa gtattccatc tttaccgaca tcaaatctga cccgaccatc    1560
gattccgtaa aaaagggtgc taaggaaatg ctgaacttcg aaccggacac tattatcagc    1620
atcggcggtg gctctccgat ggatgcagca aaagtgatgc atctgctgta cgaatacccg    1680
gaagcggaaa tcgaaaacct ggcgatcaat ttcatggaca tccgtaaacg tatctgcaat    1740
tttccgaagc tgggtacgaa agccatttcc gttgcgattc cgactaccgc gggtactggt    1800
tctgaagcga ccccgttcgc tgttattact aacgatgaaa ctggtatgaa atacccactg    1860
acgagctatg agctgacccc aaacatggca atcattgata ccgagctgat gctgaatatg    1920
ccgcgtaaac tgaccgcggc gactggcatc gacgccctgg ttcacgcgat cgaagcttat    1980
gtttctgtca tggccaccga ttatacggac gaactggctc tgcgtgctat caaaatgatt    2040
ttcaaatatc tgcctcgcgc gtacaagaac ggcaccaacg atattgaggc tcgtgaaaaa    2100
atggcacacg ccagcaacat cgcaggcatg gcattcgcta acgcttttct gggcgtatgc    2160
cattccatgg ctcataaact gggtgcaatg caccacgttc cacacggcat cgcgtgtgcg    2220
gtgctgatcg aagaggtgat caaatacaac gctactgact gtccgactaa acaaaccgcg    2280
tttccgcagt acaaatcccc aaatgcgaaa cgtaaatatg cggagatcgc cgaatatctg    2340
aacctgaaag gcacctccga caccgaaaaa gtgaccgctc tgattgaagc catcagcaaa    2400
```

```
ctgaaaattg acctgtctat cccgcagaac atcagcgcgg caggtatcaa caaaaaagat   2460

ttctataaca ccctggataa aatgagcgag ctggcgttcg atgaccagtg tacgaccgca   2520

aacccgcgct acccgctgat ctccgaactg aaagacattt atattaaatc cttctaa      2577


<210> SEQ ID NO 13
<211> LENGTH: 329
<212> TYPE: PRT
<213> ORGANISM: Escherichia coli

<400> SEQUENCE: 13

Met Lys Leu Ala Val Tyr Ser Thr Lys Gln Tyr Asp Lys Lys Tyr Leu
  1               5                  10                  15

Gln Gln Val Asn Glu Ser Phe Gly Phe Glu Leu Glu Phe Phe Asp Phe
             20                  25                  30

Leu Leu Thr Glu Lys Thr Ala Lys Thr Ala Asn Gly Cys Glu Ala Val
         35                  40                  45

Cys Ile Phe Val Asn Asp Asp Gly Ser Arg Pro Val Leu Glu Glu Leu
     50                  55                  60

Lys Lys His Gly Val Lys Tyr Ile Ala Leu Arg Cys Ala Gly Phe Asn
 65                  70                  75                  80

Asn Val Asp Leu Asp Ala Ala Lys Glu Leu Gly Leu Lys Val Val Arg
                 85                  90                  95

Val Pro Ala Tyr Asp Pro Glu Ala Val Ala Glu His Ala Ile Gly Met
            100                 105                 110

Met Met Thr Leu Asn Arg Arg Ile His Arg Ala Tyr Gln Arg Thr Arg
        115                 120                 125

Asp Ala Asn Phe Ser Leu Glu Gly Leu Thr Gly Phe Thr Met Tyr Gly
    130                 135                 140

Lys Thr Ala Gly Val Ile Gly Thr Gly Lys Ile Gly Val Ala Met Leu
145                 150                 155                 160

Arg Ile Leu Lys Gly Phe Gly Met Arg Leu Leu Ala Phe Asp Pro Tyr
                165                 170                 175

Pro Ser Ala Ala Ala Leu Glu Leu Gly Val Glu Tyr Val Asp Leu Pro
            180                 185                 190

Thr Leu Phe Ser Glu Ser Asp Val Ile Ser Leu His Cys Pro Leu Thr
        195                 200                 205

Pro Glu Asn Tyr His Leu Leu Asn Glu Ala Ala Phe Asp Gln Met Lys
    210                 215                 220

Asn Gly Val Met Ile Val Asn Thr Ser Arg Gly Ala Leu Ile Asp Ser
225                 230                 235                 240

Gln Ala Ala Ile Glu Ala Leu Lys Asn Gln Lys Ile Gly Ser Leu Gly
                245                 250                 255

Met Asp Val Tyr Glu Asn Glu Arg Asp Leu Phe Phe Glu Asp Lys Ser
            260                 265                 270

Asn Asp Val Ile Gln Asp Asp Val Phe Arg Arg Leu Ser Ala Cys His
        275                 280                 285

Asn Val Leu Phe Thr Gly His Gln Ala Phe Leu Thr Ala Glu Ala Leu
    290                 295                 300

Thr Ser Ile Ser Gln Thr Thr Leu Gln Asn Leu Ser Asn Leu Glu Lys
305                 310                 315                 320

Gly Glu Thr Cys Pro Asn Glu Leu Val
                325
```

```
<210> SEQ ID NO 14
<211> LENGTH: 990
<212> TYPE: DNA
<213> ORGANISM: Escherichia coli

<400> SEQUENCE: 14

atgaaactcg ccgtttatag cacaaaacag tacgacaaga agtacctgca acaggtgaac     60

gagtcctttg gctttgagct ggaatttttt gactttctgc tgacggaaaa aaccgctaaa    120

actgccaatg gctgcgaagc ggtatgtatt ttcgtaaacg atgacggcag ccgcccggtg    180

ctggaagagc tgaaaaagca cggcgttaaa tatatcgccc tgcgctgtgc cggtttcaat    240

aacgtcgacc ttgacgcggc aaaagaactg gggctgaaag tagtccgtgt tccagcctat    300

gatccagagg ccgttgctga acacgccatc ggtatgatga tgacgctgaa ccgccgtatt    360

caccgcgcgt atcagcgtac ccgtgacgct aacttctctc tggaaggtct gaccggcttt    420

actatgtatg gcaaaacggc aggcgttatc ggtaccggta aaatcggtgt ggcgatgctg    480

cgcattctga aaggttttgg tatgcgtctg ctggcgttcg atccgtatcc aagtgcagcg    540

gcgctggaac tcggtgtgga gtatgtcgat ctgccaaccc tgttctctga atcagacgtt    600

atctctctgc actgcccgct gacaccggaa aactaccatc tgttgaacga agccgccttc    660

gatcagatga aaaatggcgt gatgatcgtc aataccagtc gcggtgcatt gattgattct    720

caggcagcaa ttgaagcgct gaaaaatcag aaaattggtt cgttgggtat ggacgtgtat    780

gagaacgaac gcgatctatt ctttgaagat aaatccaacg acgtaattca ggatgacgta    840

ttccgtcgcc tgtctgcctg ccacaacgtg ctatttaccg ggcaccaggc attcctgaca    900

gcagaagctc tgaccagtat ttctcagact acgctgcaaa acttaagcaa tctggaaaaa    960

ggcgaaacct gcccgaacga actggtttaa                                     990


<210> SEQ ID NO 15
<211> LENGTH: 760
<212> TYPE: PRT
<213> ORGANISM: Escherichia coli

<400> SEQUENCE: 15

Met Ser Glu Leu Asn Glu Lys Leu Ala Thr Ala Trp Glu Gly Phe Thr
  1               5                  10                  15

Lys Gly Asp Trp Gln Asn Glu Val Asn Val Arg Asp Phe Ile Gln Lys
             20                  25                  30

Asn Tyr Thr Pro Tyr Glu Gly Asp Glu Ser Phe Leu Ala Gly Ala Thr
         35                  40                  45

Glu Ala Thr Thr Thr Leu Trp Asp Lys Val Met Glu Gly Val Lys Leu
     50                  55                  60

Glu Asn Arg Thr His Ala Pro Val Asp Phe Asp Thr Ala Val Ala Ser
 65                  70                  75                  80

Thr Ile Thr Ser His Asp Ala Gly Tyr Ile Asn Lys Ala Leu Glu Lys
                 85                  90                  95

Val Val Gly Leu Gln Thr Glu Ala Pro Leu Lys Arg Ala Leu Ile Pro
            100                 105                 110

Phe Gly Gly Ile Lys Met Ile Glu Gly Ser Cys Lys Ala Tyr Asn Arg
        115                 120                 125

Glu Leu Asp Pro Met Ile Lys Lys Ile Phe Thr Glu Tyr Arg Lys Thr
    130                 135                 140

His Asn Gln Gly Val Phe Asp Val Tyr Thr Pro Asp Ile Leu Arg Cys
145                 150                 155                 160
```

```
Arg Lys Ser Gly Val Leu Thr Gly Leu Pro Asp Ala Tyr Gly Arg Gly
                165                 170                 175

Arg Ile Ile Gly Asp Tyr Arg Arg Val Ala Leu Tyr Gly Ile Asp Tyr
            180                 185                 190

Leu Met Lys Asp Lys Tyr Ala Gln Phe Thr Ser Leu Gln Ala Asp Leu
        195                 200                 205

Glu Asn Gly Val Asn Leu Glu Gln Thr Ile Arg Leu Arg Glu Glu Ile
    210                 215                 220

Ala Glu Gln His Arg Ala Leu Gly Gln Met Lys Glu Met Ala Ala Lys
225                 230                 235                 240

Tyr Gly Tyr Asp Ile Ser Gly Pro Ala Thr Asn Ala Gln Glu Ala Ile
                245                 250                 255

Gln Trp Thr Tyr Phe Gly Tyr Leu Ala Ala Val Lys Ser Gln Asn Gly
            260                 265                 270

Ala Ala Met Ser Phe Gly Arg Thr Ser Thr Phe Leu Asp Val Tyr Ile
        275                 280                 285

Glu Arg Asp Leu Lys Ala Gly Lys Ile Thr Glu Gln Glu Ala Gln Glu
    290                 295                 300

Met Val Asp His Leu Val Met Lys Leu Arg Met Val Arg Phe Leu Arg
305                 310                 315                 320

Thr Pro Glu Tyr Asp Glu Leu Phe Ser Gly Asp Pro Ile Trp Ala Thr
                325                 330                 335

Glu Ser Ile Gly Gly Met Gly Leu Asp Gly Arg Thr Leu Val Thr Lys
            340                 345                 350

Asn Ser Phe Arg Phe Leu Asn Thr Leu Tyr Thr Met Gly Pro Ser Pro
        355                 360                 365

Glu Pro Asn Met Thr Ile Leu Trp Ser Glu Lys Leu Pro Leu Asn Phe
    370                 375                 380

Lys Lys Phe Ala Ala Lys Val Ser Ile Asp Thr Ser Ser Leu Gln Tyr
385                 390                 395                 400

Glu Asn Asp Asp Leu Met Arg Pro Asp Phe Asn Asn Asp Asp Tyr Ala
                405                 410                 415

Ile Ala Cys Cys Val Ser Pro Met Ile Val Gly Lys Gln Met Gln Phe
            420                 425                 430

Phe Gly Ala Arg Ala Asn Leu Ala Lys Thr Met Leu Tyr Ala Ile Asn
        435                 440                 445

Gly Gly Val Asp Glu Lys Leu Lys Met Gln Val Gly Pro Lys Ser Glu
    450                 455                 460

Pro Ile Lys Gly Asp Val Leu Asn Tyr Asp Glu Val Met Glu Arg Met
465                 470                 475                 480

Asp His Phe Met Asp Trp Leu Ala Lys Gln Tyr Ile Thr Ala Leu Asn
                485                 490                 495

Ile Ile His Tyr Met His Asp Lys Tyr Ser Tyr Glu Ala Ser Leu Met
            500                 505                 510

Ala Leu His Asp Arg Asp Val Ile Arg Thr Met Ala Cys Gly Ile Ala
        515                 520                 525

Gly Leu Ser Val Ala Ala Asp Ser Leu Ser Ala Ile Lys Tyr Ala Lys
    530                 535                 540

Val Lys Pro Ile Arg Asp Glu Asp Gly Leu Ala Ile Asp Phe Glu Ile
545                 550                 555                 560

Glu Gly Glu Tyr Pro Gln Phe Gly Asn Asn Asp Pro Arg Val Asp Asp
                565                 570                 575

Leu Ala Val Asp Leu Val Glu Arg Phe Met Lys Lys Ile Gln Lys Leu
```

```
            580                 585                 590

His Thr Tyr Arg Asp Ala Ile Pro Thr Gln Ser Val Leu Thr Ile Thr
        595                 600                 605

Ser Asn Val Val Tyr Gly Lys Lys Thr Gly Asn Thr Pro Asp Gly Arg
    610                 615                 620

Arg Ala Gly Ala Pro Phe Gly Pro Gly Ala Asn Pro Met His Gly Arg
625                 630                 635                 640

Asp Gln Lys Gly Ala Val Ala Ser Leu Thr Ser Val Ala Lys Leu Pro
                645                 650                 655

Phe Ala Tyr Ala Lys Asp Gly Ile Ser Tyr Thr Phe Ser Ile Val Pro
            660                 665                 670

Asn Ala Leu Gly Lys Asp Asp Glu Val Arg Lys Thr Asn Leu Ala Gly
        675                 680                 685

Leu Met Asp Gly Tyr Phe His His Glu Ala Ser Ile Glu Gly Gly Gln
    690                 695                 700

His Leu Asn Val Asn Val Met Asn Arg Glu Met Leu Leu Asp Ala Met
705                 710                 715                 720

Glu Asn Pro Glu Lys Tyr Pro Gln Leu Thr Ile Arg Val Ser Gly Tyr
                725                 730                 735

Ala Val Arg Phe Asn Ser Leu Thr Lys Glu Gln Gln Gln Asp Val Ile
            740                 745                 750

Thr Arg Thr Phe Thr Gln Ser Met
        755                 760


<210> SEQ ID NO 16
<211> LENGTH: 2283
<212> TYPE: DNA
<213> ORGANISM: Escherichia coli

<400> SEQUENCE: 16

atgtccgagc ttaatgaaaa gttagccaca gcctgggaag gttttaccaa aggtgactgg      60

cagaatgaag taaacgtccg tgacttcatt cagaaaaact acactccgta cgagggtgac     120

gagtccttcc tggctggcgc tactgaagcg accaccaccc tgtgggacaa agtaatggaa     180

ggcgttaaac tggaaaaccg cactcacgcg ccagttgact ttgacaccgc tgttgcttcc     240

accatcacct ctcacgacgc tggctacatc aacaaagcgt tggaaaaagt tgttggtcta     300

cagactgaag ctccgctgaa acgtgctctt atcccgttcg gtggtatcaa aatgatcgag     360

ggttcctgca aagcgtacaa ccgcgaactg gacccgatga tcaaaaaaat cttcactgaa     420

taccgtaaaa ctcacaacca gggcgtgttc gacgtttaca ctccggacat cctgcgttgc     480

cgtaaatccg gtgttctgac cggtctgcca gatgcttatg gccgtggccg tatcatcggt     540

gactaccgtc gcgttgcgct gtacggtatc gactacctga tgaaagacaa atacgctcag     600

ttcacctctc tgcaggctga tctggaaaac ggcgtaaacc tggaacagac tatccgtctg     660

cgcgaagaaa tcgctgaaca gcaccgcgct ctgggtcaga tgaaagaaat ggctgcgaaa     720

tacggctacg acatctctgg tccggctacc aacgctcagg aagctatcca gtggacttac     780

ttcggctacc tggctgctgt taagtctcag aacggtgctg caatgtcctt cggtcgtacc     840

tccaccttcc tggatgtgta catcgaacgt gacctgaaag ctggcaagat caccgaacaa     900

gaagcgcagg aaatggttga ccacctggtc atgaaactgc gtatggttcg cttcctgcgt     960

actccggaat acgatgaact gttctctggc gacccgatct gggcaaccga atctatcggt    1020

ggtatgggcc tcgacggtcg taccctggtt accaaaaaca gcttccgttt cctgaacacc    1080
```

```
ctgtacacca tgggtccgtc tccggaaccg aacatgacca ttctgtggtc tgaaaaactg   1140

ccgctgaact tcaagaaatt cgccgctaaa gtgtccatcg acacctcttc tctgcaatat   1200

gagaacgatg acctgatgcg tccggacttc aacaacgatg actacgctat tgcttgctgc   1260

gtaagcccga tgatcgttgg taaacaaatg cagttcttcg gtgcgcgtgc aaacctggcg   1320

aaaaccatgc tgtacgcaat caacggcggc gttgacgaaa aactgaaaat gcaggttggt   1380

ccgaagtctg aaccgatcaa aggcgatgtc ctgaactatg atgaagtgat ggagcgcatg   1440

gatcacttca tggactggct ggctaaacag tacatcactg cactgaacat catccactac   1500

atgcacgaca agtacagcta cgaagcctct ctgatggcgc tgcacgaccg tgacgttatc   1560

cgcaccatgg cgtgtggtat cgctggtctg tccgttgctg ctgactccct gtctgcaatc   1620

aaatatgcga aagttaaacc gattcgtgac gaagacggtc tggctatcga cttcgaaatc   1680

gaaggcgaat acccgcagtt tggtaacaat gatccgcgtg tagatgacct ggctgttgac   1740

ctggtagaac gtttcatgaa gaaaattcag aaactgcaca cctaccgtga cgctatcccg   1800

actcagtctg ttctgaccat cacttctaac gttgtgtatg gtaagaaaac tggtaacacc   1860

ccagacggtc gtcgtgctgg cgcgccgttc ggaccgggtg ctaacccgat gcacggtcgt   1920

gaccagaaag gtgctgtagc gtctctgact tccgttgcta aactaccgtt tgcttacgct   1980

aaagatggta tctcctacac cttctctatc gttccgaacg cactgggtaa agacgacgaa   2040

gttcgtaaga ccaacctggc tggtctgatg gatggttact tccaccacga agcatccatc   2100

gaaggtggtc agcacctgaa cgttaacgtg atgaaccgtg aaatgctgct cgacgcgatg   2160

gaaaacccgg aaaaatatcc gcagctgacc atccgtgtat ctggctacgc agtacgtttc   2220

aactcgctga ctaaagaaca gcagcaggac gttattactc gtaccttcac tcaatctatg   2280

taa                                                                 2283
```

```
<210> SEQ ID NO 17
<211> LENGTH: 891
<212> TYPE: PRT
<213> ORGANISM: Escherichia coli

<400> SEQUENCE: 17

Met Ala Val Thr Asn Val Ala Glu Leu Asn Ala Leu Val Glu Arg Val
  1               5                  10                  15

Lys Lys Ala Gln Arg Glu Tyr Ala Ser Phe Thr Gln Glu Gln Val Asp
             20                  25                  30

Lys Ile Phe Arg Ala Ala Ala Leu Ala Ala Ala Asp Ala Arg Ile Pro
         35                  40                  45

Leu Ala Lys Met Ala Val Ala Glu Ser Gly Met Gly Ile Val Glu Asp
     50                  55                  60

Lys Val Ile Lys Asn His Phe Ala Ser Glu Tyr Ile Tyr Asn Ala Tyr
 65                  70                  75                  80

Lys Asp Glu Lys Thr Cys Gly Val Leu Ser Glu Asp Asp Thr Phe Gly
                 85                  90                  95

Thr Ile Thr Ile Ala Glu Pro Ile Gly Ile Ile Cys Gly Ile Val Pro
            100                 105                 110

Thr Thr Asn Pro Thr Ser Thr Ala Ile Phe Lys Ser Leu Ile Ser Leu
        115                 120                 125

Lys Thr Arg Asn Ala Ile Ile Phe Ser Pro His Pro Arg Ala Lys Asp
    130                 135                 140

Ala Thr Asn Lys Ala Ala Asp Ile Val Leu Gln Ala Ala Ile Ala Ala
145                 150                 155                 160
```

```
Gly Ala Pro Lys Asp Leu Ile Gly Trp Ile Asp Gln Pro Ser Val Glu
                165                 170                 175

Leu Ser Asn Ala Leu Met His His Pro Asp Ile Asn Leu Ile Leu Ala
            180                 185                 190

Thr Gly Gly Pro Gly Met Val Lys Ala Ala Tyr Ser Ser Gly Lys Pro
        195                 200                 205

Ala Ile Gly Val Gly Ala Gly Asn Thr Pro Val Val Ile Asp Glu Thr
    210                 215                 220

Ala Asp Ile Lys Arg Ala Val Ala Ser Val Leu Met Ser Lys Thr Phe
225                 230                 235                 240

Asp Asn Gly Val Ile Cys Ala Ser Glu Gln Ser Val Val Val Val Asp
                245                 250                 255

Ser Val Tyr Asp Ala Val Arg Glu Arg Phe Ala Thr His Gly Gly Tyr
            260                 265                 270

Leu Leu Gln Gly Lys Glu Leu Lys Ala Val Gln Asp Val Ile Leu Lys
        275                 280                 285

Asn Gly Ala Leu Asn Ala Ala Ile Val Gly Gln Pro Ala Tyr Lys Ile
    290                 295                 300

Ala Glu Leu Ala Gly Phe Ser Val Pro Glu Asn Thr Lys Ile Leu Ile
305                 310                 315                 320

Gly Glu Val Thr Val Val Asp Glu Ser Glu Pro Phe Ala His Glu Lys
                325                 330                 335

Leu Ser Pro Thr Leu Ala Met Tyr Arg Ala Lys Asp Phe Glu Asp Ala
            340                 345                 350

Val Glu Lys Ala Glu Lys Leu Val Ala Met Gly Gly Ile Gly His Thr
        355                 360                 365

Ser Cys Leu Tyr Thr Asp Gln Asp Asn Gln Pro Ala Arg Val Ser Tyr
    370                 375                 380

Phe Gly Gln Lys Met Lys Thr Ala Arg Ile Leu Ile Asn Thr Pro Ala
385                 390                 395                 400

Ser Gln Gly Gly Ile Gly Asp Leu Tyr Asn Phe Lys Leu Ala Pro Ser
                405                 410                 415

Leu Thr Leu Gly Cys Gly Ser Trp Gly Gly Asn Ser Ile Ser Glu Asn
            420                 425                 430

Val Gly Pro Lys His Leu Ile Asn Lys Lys Thr Val Ala Lys Arg Ala
        435                 440                 445

Glu Asn Met Leu Trp His Lys Leu Pro Lys Ser Ile Tyr Phe Arg Arg
    450                 455                 460

Gly Ser Leu Pro Ile Ala Leu Asp Glu Val Ile Thr Asp Gly His Lys
465                 470                 475                 480

Arg Ala Leu Ile Val Thr Asp Arg Phe Leu Phe Asn Asn Gly Tyr Ala
                485                 490                 495

Asp Gln Ile Thr Ser Val Leu Lys Ala Ala Gly Val Glu Thr Glu Val
            500                 505                 510

Phe Phe Glu Val Glu Ala Asp Pro Thr Leu Ser Ile Val Arg Lys Gly
        515                 520                 525

Ala Glu Leu Ala Asn Ser Phe Lys Pro Asp Val Ile Ile Ala Leu Gly
    530                 535                 540

Gly Gly Ser Pro Met Asp Ala Ala Lys Ile Met Trp Val Met Tyr Glu
545                 550                 555                 560

His Pro Glu Thr His Phe Glu Glu Leu Ala Leu Arg Phe Met Asp Ile
                565                 570                 575
```

```
Arg Lys Arg Ile Tyr Lys Phe Pro Lys Met Gly Val Lys Ala Lys Met
            580                 585                 590

Ile Ala Val Thr Thr Thr Ser Gly Thr Gly Ser Glu Val Thr Pro Phe
        595                 600                 605

Ala Val Val Thr Asp Asp Ala Thr Gly Gln Lys Tyr Pro Leu Ala Asp
    610                 615                 620

Tyr Ala Leu Thr Pro Asp Met Ala Ile Val Asp Ala Asn Leu Val Met
625                 630                 635                 640

Asp Met Pro Lys Ser Leu Cys Ala Phe Gly Gly Leu Asp Ala Val Thr
                645                 650                 655

His Ala Met Glu Ala Tyr Val Ser Val Leu Ala Ser Glu Phe Ser Asp
            660                 665                 670

Gly Gln Ala Leu Gln Ala Leu Lys Leu Leu Lys Glu Tyr Leu Pro Ala
        675                 680                 685

Ser Tyr His Glu Gly Ser Lys Asn Pro Val Ala Arg Glu Arg Val His
    690                 695                 700

Ser Ala Ala Thr Ile Ala Gly Ile Ala Phe Ala Asn Ala Phe Leu Gly
705                 710                 715                 720

Val Cys His Ser Met Ala His Lys Leu Gly Ser Gln Phe His Ile Pro
                725                 730                 735

His Gly Leu Ala Asn Ala Leu Leu Ile Cys Asn Val Ile Arg Tyr Asn
            740                 745                 750

Ala Asn Asp Asn Pro Thr Lys Gln Thr Ala Phe Ser Gln Tyr Asp Arg
        755                 760                 765

Pro Gln Ala Arg Arg Arg Tyr Ala Glu Ile Ala Asp His Leu Gly Leu
    770                 775                 780

Ser Ala Pro Gly Asp Arg Thr Ala Ala Lys Ile Glu Lys Leu Leu Ala
785                 790                 795                 800

Trp Leu Glu Thr Leu Lys Ala Glu Leu Gly Ile Pro Lys Ser Ile Arg
                805                 810                 815

Glu Ala Gly Val Gln Glu Ala Asp Phe Leu Ala Asn Val Asp Lys Leu
            820                 825                 830

Ser Glu Asp Ala Phe Asp Asp Gln Cys Thr Gly Ala Asn Pro Arg Tyr
        835                 840                 845

Pro Leu Ile Ser Glu Leu Lys Gln Ile Leu Leu Asp Thr Tyr Tyr Gly
    850                 855                 860

Arg Asp Tyr Val Glu Gly Glu Thr Ala Ala Lys Lys Glu Ala Ala Pro
865                 870                 875                 880

Ala Lys Ala Glu Lys Lys Ala Lys Lys Ser Ala
                885                 890
```

<210> SEQ ID NO 18
<211> LENGTH: 2676
<212> TYPE: DNA
<213> ORGANISM: Escherichia coli

<400> SEQUENCE: 18

```
atggctgtta ctaatgtcgc tgaacttaac gcactcgtag agcgtgtaaa aaaagcccag      60

cgtgaatatg ccagtttcac tcaagagcaa gtagacaaaa tcttccgcgc cgccgctctg     120

gctgctgcag atgctcgaat cccactcgcg aaaatggccg ttgccgaatc cggcatgggt     180

atcgtcgaag ataaagtgat caaaaaccac tttgcttctg aatatatcta caacgcctat     240

aaagatgaaa aaacctgtgg tgttctgtct gaagacgaca cttttggtac catcactatc     300

gctgaaccaa tcggtattat ttgcggtatc gttccgacca ctaacccgac ttcaactgct     360
```

```
atcttcaaat cgctgatcag tctgaagacc cgtaacgcca ttatcttctc cccgcacccg    420
cgtgcaaaag atgccaccaa caaagcggct gatatcgttc tgcaggctgc tatcgctgcc    480
ggtgctccga aagatctgat cggctggatc gatcaacctt ctgttgaact gtctaacgca    540
ctgatgcacc acccagacat caacctgatc ctcgcgactg gtggtccggg catggttaaa    600
gccgcataca gctccggtaa accagctatc ggtgtaggcg cgggcaacac tccagttgtt    660
atcgatgaaa ctgctgatat caaacgtgca gttgcatctg tactgatgtc caaaaccttc    720
gacaacggcg taatctgtgc ttctgaacag tctgttgttg ttgttgactc tgtttatgac    780
gctgtacgtg aacgttttgc aacccacggc ggctatctgt tgcagggtaa agagctgaaa    840
gctgttcagg atgttatcct gaaaaacggt gcgctgaacg cggctatcgt tggtcagcca    900
gcctataaaa ttgctgaact ggcaggcttc tctgtaccag aaaacaccaa gattctgatc    960
ggtgaagtga ccgttgttga tgaaagcgaa ccgttcgcac atgaaaaact gtccccgact   1020
ctggcaatgt accgcgctaa agatttcgaa gacgcggtag aaaaagcaga gaaactggtt   1080
gctatgggcg gtatcggtca tacctcttgc ctgtacactg accaggataa ccaaccggct   1140
cgcgtttctt acttcggtca gaaaatgaaa acggctcgta tcctgattaa caccccagcg   1200
tctcagggtg gtatcggtga cctgtataac ttcaaactcg caccttccct gactctgggt   1260
tgtggttctt ggggtggtaa ctccatctct gaaaacgttg gtccgaaaca cctgatcaac   1320
aagaaaaccg ttgctaagcg agctgaaaac atgttgtggc acaaacttcc gaaatctatc   1380
tacttccgcc gtggctccct gccaatcgcg ctggatgaag tgattactga tggccacaaa   1440
cgtgcgctca tcgtgactga ccgcttcctg ttcaacaatg gttatgctga tcagatcact   1500
tccgtactga aagcagcagg cgttgaaact gaagtcttct tcgaagtaga agcggacccg   1560
accctgagca tcgttcgtaa aggtgcagaa ctggcaaact ccttcaaacc agacgtgatt   1620
atcgcgctgg gtggtggttc cccgatggac gccgcgaaga tcatgtgggt tatgtacgaa   1680
catccggaaa ctcacttcga agagctggcg ctgcgcttta tggatatccg taaacgtatc   1740
tacaagttcc cgaaaatggg cgtgaaagcg aaaatgatcg ctgtcaccac cacttctggt   1800
acaggttctg aagtcactcc gtttgcggtt gtaactgacg acgctactgg tcagaaatat   1860
ccgctggcag actatgcgct gactccggat atggcgattg tcgacgccaa cctggttatg   1920
gacatgccga agtccctgtg tgctttcggt ggtctggacg cagtaactca cgccatggaa   1980
gcttatgttt ctgtactggc atctgagttc tctgatggtc aggctctgca ggcactgaaa   2040
ctgctgaaag aatatctgcc agcgtcctac cacgaagggt ctaaaaatcc ggtagcgcgt   2100
gaacgtgttc acagtgcagc gactatcgcg ggtatcgcgt ttgcgaacgc cttcctgggt   2160
gtatgtcact caatggcgca caaactgggt tcccagttcc atattccgca cggtctggca   2220
aacgccctgc tgatttgtaa cgttattcgc tacaatgcga acgacaaccc gaccaagcag   2280
actgcattca gccagtatga ccgtccgcag gctcgccgtc gttatgctga aattgccgac   2340
cacttgggtc tgagcgcacc gggcgaccgt actgctgcta agatcgagaa actgctggca   2400
tggctggaaa cgctgaaagc tgaactgggt attccgaaat ctatccgtga agctggcgtt   2460
caggaagcag acttcctggc gaacgtggat aaactgtctg aagatgcgtt cgatgaccag   2520
tgcaccggcg ctaacccgcg ttacccgctg atctccgagc tgaaacagat cctgctggat   2580
acctactacg gtcgtgatta tgtagaaggt gaaactgcag cgaaaaaaga agccgctccg   2640
gctaaagctg agaaaaaagc gaaaaaatcc gcttaa                             2676
```

```
<210> SEQ ID NO 19
<211> LENGTH: 312
<212> TYPE: PRT
<213> ORGANISM: Escherichia coli

<400> SEQUENCE: 19

Met Lys Val Ala Val Leu Gly Ala Ala Gly Gly Ile Gly Gln Ala Leu
1               5                   10                  15

Ala Leu Leu Leu Lys Thr Gln Leu Pro Ser Gly Ser Glu Leu Ser Leu
            20                  25                  30

Tyr Asp Ile Ala Pro Val Thr Pro Gly Val Ala Val Asp Leu Ser His
        35                  40                  45

Ile Pro Thr Ala Val Lys Ile Lys Gly Phe Ser Gly Glu Asp Ala Thr
    50                  55                  60

Pro Ala Leu Glu Gly Ala Asp Val Val Leu Ile Ser Ala Gly Val Ala
65                  70                  75                  80

Arg Lys Pro Gly Met Asp Arg Ser Asp Leu Phe Asn Val Asn Ala Gly
                85                  90                  95

Ile Val Lys Asn Leu Val Gln Gln Val Ser Lys Thr Cys Pro Lys Ala
            100                 105                 110

Cys Ile Gly Ile Ile Thr Asn Pro Val Asn Thr Thr Val Ala Ile Ala
        115                 120                 125

Ala Glu Val Leu Lys Lys Ala Gly Val Tyr Asp Lys Asn Lys Leu Phe
    130                 135                 140

Gly Val Thr Thr Leu Asp Ile Ile Arg Ser Asn Thr Phe Val Ala Glu
145                 150                 155                 160

Leu Lys Gly Lys Gln Pro Gly Glu Val Glu Val Pro Val Ile Gly Gly
                165                 170                 175

His Ser Gly Val Thr Ile Leu Pro Leu Leu Ser Gln Val Pro Gly Val
            180                 185                 190

Ser Phe Thr Glu Gln Glu Val Ala Asp Leu Thr Lys Arg Ile Gln Asn
        195                 200                 205

Ala Gly Thr Glu Val Val Glu Ala Lys Ala Gly Gly Gly Ser Ala Thr
    210                 215                 220

Leu Ser Met Gly Gln Ala Ala Ala Arg Phe Gly Leu Ser Leu Val Arg
225                 230                 235                 240

Ala Leu Gln Gly Glu Gln Gly Val Val Glu Cys Ala Tyr Val Glu Gly
                245                 250                 255

Asp Gly Gln Tyr Ala Arg Phe Phe Ser Gln Pro Leu Leu Leu Gly Lys
            260                 265                 270

Asn Gly Val Glu Glu Arg Lys Ser Ile Gly Thr Leu Ser Ala Phe Glu
        275                 280                 285

Gln Ser Ala Leu Glu Gly Met Leu Asp Thr Leu Lys Lys Asp Ile Ala
    290                 295                 300

Leu Gly Glu Glu Phe Val Asn Lys
305                 310


<210> SEQ ID NO 20
<211> LENGTH: 939
<212> TYPE: DNA
<213> ORGANISM: Escherichia coli

<400> SEQUENCE: 20

atgaaagtcg cagtcctcgg cgctgctggc ggtattggcc aggcgcttgc actactgtta      60

aaaacccaac tgccttcagg ttcagaactc tctctgtatg atatcgctcc agtgactccc     120
```

```
ggtgtggctg tcgatctgag ccatatccct actgctgtga aaatcaaagg tttttctggt    180

gaagatgcga ctccggcgct ggaaggcgca gatgtcgttc ttatctctgc aggtgtagcg    240

cgtaaaccgg gtatggatcg ttccgacctg tttaacgtta acgccggcat cgtgaaaaac    300

ctggtacagc aagtttcgaa aacctgcccg aaagcgtgca ttggtattat cactaacccg    360

gttaacacca cagttgcgat tgctgctgaa gtgctgaaaa aagccggtgt ttatgacaaa    420

aacaaactgt tcggcgttac cacgctggat atcattcgtt ccaacacctt tgttgcggaa    480

ctgaaaggca aacagccagg cgaagttgaa gtgccggtta ttggcggtca ctctggtgtt    540

accattctgc cgctgctgtc acaggttcct ggcgttagtt ttaccgagca ggaagtggct    600

gatctgacca aacgtatcca gaacgcaggt actgaagtgg ttgaagcgaa agccggtggc    660

gggtctgcaa ccctgtctat gggccaggca gctgcacgtt ttggtctgtc tctggtacgc    720

gcactgcagg gcgaacaagg cgttgtcgaa tgtgcctatg ttgaaggcga cggtcagtac    780

gcacgtttct tctctcaacc gctgctgctg ggtaaaaacg gcgtggaaga gcgtaaatct    840

atcggtaccc tgagcgcatt tgaacagagc gcactggaag gtatgctgga tacgctgaag    900

aaagatatcg ccctgggcga agagttcgtt aataagtaa                           939
```

```
<210> SEQ ID NO 21
<211> LENGTH: 238
<212> TYPE: PRT
<213> ORGANISM: Escherichia coli

<400> SEQUENCE: 21

Met Gln Thr Pro His Ile Leu Ile Val Glu Asp Glu Leu Val Thr Arg
  1               5                  10                  15

Asn Thr Leu Lys Ser Ile Phe Glu Ala Glu Gly Tyr Asp Val Phe Glu
             20                  25                  30

Ala Thr Asp Gly Ala Glu Met His Gln Ile Leu Ser Glu Tyr Asp Ile
         35                  40                  45

Asn Leu Val Ile Met Asp Ile Asn Leu Pro Gly Lys Asn Gly Leu Leu
     50                  55                  60

Leu Ala Arg Glu Leu Arg Glu Gln Ala Asn Val Ala Leu Met Phe Leu
 65                  70                  75                  80

Thr Gly Arg Asp Asn Glu Val Asp Lys Ile Leu Gly Leu Glu Ile Gly
                 85                  90                  95

Ala Asp Asp Tyr Ile Thr Lys Pro Phe Asn Pro Arg Glu Leu Thr Ile
            100                 105                 110

Arg Ala Arg Asn Leu Leu Ser Arg Thr Met Asn Leu Gly Thr Val Ser
        115                 120                 125

Glu Glu Arg Arg Ser Val Glu Ser Tyr Lys Phe Asn Gly Trp Glu Leu
    130                 135                 140

Asp Ile Asn Ser Arg Ser Leu Ile Gly Pro Asp Gly Glu Gln Tyr Lys
145                 150                 155                 160

Leu Pro Arg Ser Glu Phe Arg Ala Met Leu His Phe Cys Glu Asn Pro
                165                 170                 175

Gly Lys Ile Gln Ser Arg Ala Glu Leu Leu Lys Lys Met Thr Gly Arg
            180                 185                 190

Glu Leu Lys Pro His Asp Arg Thr Val Asp Val Thr Ile Arg Arg Ile
        195                 200                 205

Arg Lys His Phe Glu Ser Thr Pro Asp Thr Pro Glu Ile Ile Ala Thr
    210                 215                 220
```

```
Ile His Gly Glu Gly Tyr Arg Phe Cys Gly Asp Leu Glu Asp
225                 230                 235


<210> SEQ ID NO 22
<211> LENGTH: 717
<212> TYPE: DNA
<213> ORGANISM: Escherichia coli

<400> SEQUENCE: 22

atgcagaccc cgcacattct tatcgttgaa gacgagttgg taacacgcaa cacgttgaaa      60

agtattttcg aagcggaagg ctatgatgtt ttcgaagcga cagatggcgc ggaaatgcat     120

cagatcctct ctgaatatga catcaacctg gtgatcatgg atatcaatct gccgggtaag     180

aacggtcttc tgttagcgcg tgaactgcgc gagcaggcga atgttgcgtt gatgttcctg     240

actggccgtg acaacgaagt cgataaaatt ctcggcctcg aaatcggtgc agatgactac     300

atcaccaaac cgttcaaccc gcgtgaactg acgattcgtg cacgcaacct gctgtcccgt     360

accatgaatc tgggtactgt cagcgaagaa cgtcgtagcg ttgaaagcta caagttcaat     420

ggttgggaac tggatatcaa cagccgttcg ttgatcggcc ctgatggcga gcagtacaag     480

ctgccgcgca gcgagttccg cgccatgctt cacttctgtg aaaacccagg caaaattcag     540

tctcgtgctg aactgctgaa gaaaatgacc ggccgtgagc tgaaaccaca cgaccgtact     600

gtagacgtga cgatccgccg tattcgtaaa catttcgaat ctacgccgga tacgccggaa     660

atcatcgcca ccatccacgg tgaaggttat cgcttctgtg gtgatctgga agattaa        717


<210> SEQ ID NO 23
<211> LENGTH: 462
<212> TYPE: PRT
<213> ORGANISM: Escherichia coli

<400> SEQUENCE: 23

Met Thr Ile Thr Pro Ala Thr His Ala Ile Ser Ile Asn Pro Ala Thr
  1               5                  10                  15

Gly Glu Gln Leu Ser Val Leu Pro Trp Ala Gly Ala Asn Asp Ile Glu
             20                  25                  30

Asn Ala Leu Gln Leu Ala Ala Ala Gly Phe Arg Asp Trp Arg Glu Thr
         35                  40                  45

Asn Ile Asp Tyr Arg Ala Glu Lys Leu Arg Gly Ile Gly Lys Ala Leu
     50                  55                  60

Arg Ala Arg Ser Glu Glu Met Ala Gln Met Ile Thr Arg Glu Met Gly
 65                  70                  75                  80

Lys Pro Ile Asn Gln Ala Arg Ala Glu Val Ala Lys Ser Ala Asn Leu
                 85                  90                  95

Cys Asp Trp Tyr Ala Glu His Gly Pro Ala Met Leu Lys Ala Glu Pro
            100                 105                 110

Thr Leu Val Glu Asn Gln Gln Ala Val Ile Glu Tyr Arg Pro Leu Gly
        115                 120                 125

Thr Ile Leu Ala Ile Met Pro Trp Asn Phe Pro Leu Trp Gln Val Met
    130                 135                 140

Arg Gly Ala Val Pro Ile Ile Leu Ala Gly Asn Gly Tyr Leu Leu Lys
145                 150                 155                 160

His Ala Pro Asn Val Met Gly Cys Ala Gln Leu Ile Ala Gln Val Phe
                165                 170                 175

Lys Asp Ala Gly Ile Pro Gln Gly Val Tyr Gly Trp Leu Asn Ala Asp
            180                 185                 190
```

```
Asn Asp Gly Val Ser Gln Met Ile Lys Asp Ser Arg Ile Ala Ala Val
        195                 200                 205

Thr Val Thr Gly Ser Val Arg Ala Gly Ala Ala Ile Gly Ala Gln Ala
    210                 215                 220

Gly Ala Ala Leu Lys Lys Cys Val Leu Glu Leu Gly Gly Ser Asp Pro
225                 230                 235                 240

Phe Ile Val Leu Asn Asp Ala Asp Leu Glu Leu Ala Val Lys Ala Ala
                245                 250                 255

Val Ala Gly Arg Tyr Gln Asn Thr Gly Gln Val Cys Ala Ala Ala Lys
            260                 265                 270

Arg Phe Ile Ile Glu Glu Gly Ile Ala Ser Ala Phe Thr Glu Arg Phe
        275                 280                 285

Val Ala Ala Ala Ala Ala Leu Lys Met Gly Asp Pro Arg Asp Glu Glu
    290                 295                 300

Asn Ala Leu Gly Pro Met Ala Arg Phe Asp Leu Arg Asp Glu Leu His
305                 310                 315                 320

His Gln Val Glu Lys Thr Leu Ala Gln Gly Ala Arg Leu Leu Leu Gly
                325                 330                 335

Gly Glu Lys Met Ala Gly Ala Gly Asn Tyr Tyr Pro Pro Thr Val Leu
            340                 345                 350

Ala Asn Val Thr Pro Glu Met Thr Ala Phe Arg Glu Glu Met Phe Gly
        355                 360                 365

Pro Val Ala Ala Ile Thr Val Ala Lys Asp Ala Glu His Ala Leu Glu
    370                 375                 380

Leu Ala Asn Asp Ser Glu Phe Gly Leu Ser Ala Thr Ile Phe Thr Thr
385                 390                 395                 400

Asp Glu Thr Gln Ala Arg Gln Met Ala Ala Arg Leu Glu Cys Gly Gly
                405                 410                 415

Val Phe Ile Asn Gly Tyr Cys Ala Ser Asp Ala Arg Val Ala Phe Gly
            420                 425                 430

Gly Val Lys Lys Ser Gly Phe Gly Arg Glu Leu Ser His Phe Gly Leu
        435                 440                 445

His Glu Phe Cys Asn Ile Gln Thr Val Trp Lys Asp Arg Ile
    450                 455                 460


<210> SEQ ID NO 24
<211> LENGTH: 1389
<212> TYPE: DNA
<213> ORGANISM: Escherichia coli

<400> SEQUENCE: 24

atgaccatta ctccggcaac tcatgcaatt tcgataaatc ctgccacggg tgaacaactt      60

tctgtgctgc cgtgggctgg cgctaacgat atcgaaaacg cacttcagct ggcggcagca     120

ggctttcgcg actggcgcga gacaaatata gattatcgtg ctgaaaaact gcgtggtatc     180

ggtaaggctc tgcgcgcccg tagcgaagaa atggcgcaaa tgatcacccg tgaaatgggc     240

aaaccaatca atcaggcgcg cgctgaagtg gcgaaatcgg cgaatttgtg tgactggtat     300

gcagaacatg gtccggcaat gctgaaggcg gaacctacgc tggtggaaaa tcagcaggca     360

gttattgagt atcgaccgtt ggggacgatt ctggcgatta tgccgtggaa ctttccgtta     420

tggcaggtga tgcgtggcgc ggttcccatc attcttgcag gtaacggcta cttacttaaa     480

catgcgccga atgtgatggg ctgtgctcag ctcattgccc aggtgtttaa agatgcggga     540

atcccgcaag gcgtatatgg ctggctgaat gccgacaacg acggtgtcag tcaaatgatt     600
```

```
aaagattcgc gcattgctgc tgtcacggtg accggaagtg ttcgtgcggg agcggctatt    660

ggcgcacagg ctggagcggc actgaaaaaa tgcgtactgg aactgggcgg ttcggatcca    720

tttattgtgc ttaacgatgc cgatctggaa ctggcggtta aagcggcggt agccggacgt    780

tatcagaata ccggacaggt ttgtgcagcg gcaaaacgct ttattatcga agagggaatt    840

gcttctgcat ttaccgaacg ttttgtggca gctgcggcag ccttgaaaat gggcgatccc    900

cgtgatgaag agaacgctct cggaccaatg gctcgttttg atttacgtga tgagctgcat    960

catcaggtgg agaaaaccct ggcgcagggt gcgcgtttgt tactgggcgg ggaaaagatg   1020

gctggggcag gtaattacta tccgccaacg gttctggcga atgttacccc agaaatgacc   1080

gcgtttcggg aagaaatgtt tggccctgtt gcggcaatca ccgttgcgaa agatgcagaa   1140

catgcgctgg aactggctaa tgatagtgag ttcggccttt cagcgaccat tttaccacc    1200

gacgaaacac aggccagaca gatggcggca cgtctggaat gcggtggggt gtttatcaat   1260

ggttattgtg ccagcgacgc gcgagtggcc tttggtggcg tgaaaaagag tggctttggt   1320

cgtgagcttt cccatttcgg cttacacgaa ttctgtaata tccagacggt gtggaaagac   1380

cggatctga                                                           1389


<210> SEQ ID NO 25
<211> LENGTH: 482
<212> TYPE: PRT
<213> ORGANISM: Escherichia coli

<400> SEQUENCE: 25

Met Lys Leu Asn Asp Ser Asn Leu Phe Arg Gln Gln Ala Leu Ile Asn
1               5                   10                  15

Gly Glu Trp Leu Asp Ala Asn Asn Gly Glu Val Ile Asp Val Thr Asn
            20                  25                  30

Pro Ala Asn Gly Asp Lys Leu Gly Ser Val Pro Lys Met Gly Ala Asp
        35                  40                  45

Glu Thr Arg Ala Ala Ile Asp Ala Ala Asn Arg Ala Leu Pro Ala Trp
    50                  55                  60

Arg Ala Leu Thr Ala Lys Glu Arg Ala Asn Ile Leu Arg Asn Trp Phe
65                  70                  75                  80

Asn Leu Met Met Glu His Gln Asp Asp Leu Ala Arg Leu Met Thr Leu
                85                  90                  95

Glu Gln Gly Lys Pro Leu Ala Glu Ala Lys Gly Glu Ile Ser Tyr Ala
            100                 105                 110

Ala Ser Phe Ile Glu Trp Phe Ala Glu Glu Gly Lys Arg Ile Tyr Gly
        115                 120                 125

Asp Thr Ile Pro Gly His Gln Ala Asp Lys Arg Leu Ile Val Ile Lys
    130                 135                 140

Gln Pro Ile Gly Val Thr Ala Ala Ile Thr Pro Trp Asn Phe Pro Ala
145                 150                 155                 160

Ala Met Ile Thr Arg Lys Ala Gly Pro Ala Leu Ala Ala Gly Cys Thr
                165                 170                 175

Met Val Leu Lys Pro Ala Ser Gln Thr Pro Phe Ser Ala Leu Ala Leu
            180                 185                 190

Ala Glu Leu Ala Ile Arg Ala Gly Ile Pro Ala Gly Val Phe Asn Val
        195                 200                 205

Val Thr Gly Ser Ala Gly Ala Val Gly Asn Glu Leu Thr Ser Asn Pro
    210                 215                 220

Leu Val Arg Lys Leu Ser Phe Thr Gly Ser Thr Glu Ile Gly Arg Gln
```

```
225                 230                 235                 240

Leu Met Glu Gln Cys Ala Lys Asp Ile Lys Lys Val Ser Leu Glu Leu
                245                 250                 255

Gly Gly Asn Ala Pro Phe Ile Val Phe Asp Asp Ala Asp Leu Asp Lys
            260                 265                 270

Ala Val Glu Gly Ala Leu Ala Ser Lys Phe Arg Asn Ala Gly Gln Thr
        275                 280                 285

Cys Val Cys Ala Asn Arg Leu Tyr Val Gln Asp Gly Val Tyr Asp Arg
    290                 295                 300

Phe Ala Glu Lys Leu Gln Gln Ala Val Ser Lys Leu His Ile Gly Asp
305                 310                 315                 320

Gly Leu Asp Lys Gly Val Thr Ile Gly Pro Leu Ile Asp Glu Lys Ala
                325                 330                 335

Val Ala Lys Val Glu Glu His Ile Ala Asp Ala Leu Glu Lys Gly Ala
            340                 345                 350

Arg Val Val Cys Gly Gly Lys Ala His Glu Arg Gly Gly Asn Phe Phe
        355                 360                 365

Gln Pro Thr Ile Leu Val Asp Val Pro Ala Asn Ala Lys Val Ser Lys
    370                 375                 380

Glu Glu Thr Phe Gly Pro Leu Ala Pro Leu Phe Arg Phe Lys Asp Glu
385                 390                 395                 400

Ala Asp Val Ile Ala Gln Ala Asn Asp Thr Glu Phe Gly Leu Ala Ala
                405                 410                 415

Tyr Phe Tyr Ala Arg Asp Leu Ser Arg Val Phe Arg Val Gly Glu Ala
            420                 425                 430

Leu Glu Tyr Gly Ile Val Gly Ile Asn Thr Gly Ile Ile Ser Asn Glu
        435                 440                 445

Val Ala Pro Phe Gly Gly Ile Lys Ala Ser Gly Leu Gly Arg Glu Gly
    450                 455                 460

Ser Lys Tyr Gly Ile Glu Asp Tyr Leu Glu Ile Lys Tyr Met Cys Ile
465                 470                 475                 480

Gly Leu
```

<210> SEQ ID NO 26
<211> LENGTH: 1449
<212> TYPE: DNA
<213> ORGANISM: Escherichia coli

<400> SEQUENCE: 26

```
atgaaactta acgacagtaa cttattccgc cagcaggcgt tgattaacgg ggaatggctg      60

gacgccaaca atggcgaggt catcgacgtc accaatccgg cgaacggcga caagctgggt     120

agcgtaccca aaatgggcgc tgatgaaacc cgcgccgcta tcgacgccgc caaccgcgct     180

ctgcccgcct ggcgtgcgct caccgccaaa gaacgcgcca acattctgcg caactggttc     240

aatttgatga tggagcatca ggacgattta gcgcgtctga tgaccctcga acagggtaaa     300

ccgctggctg aagcgaaagg tgaaatcagc tacgccgcct cctttattga gtggtttgct     360

gaagaaggca aacgcattta tggcgacacc attcccggtc atcaggccga taaacgcctg     420

attgttatca agcagccgat tggcgttacc gccgccatca cgccgtggaa cttcccggcg     480

gcgatgatta cccgtaaagc cggtccggcg ctggcggcag gctgcacgat ggtgctgaaa     540

cccgccagtc agacgccgtt ctctgcgctg gcgctggcgg agctggcgat tcgcgcgggc     600

attccggctg ggtatttaa cgtggtcacc ggttcggcgg gcgcagtcgg taacgaactg     660
```

```
accagcaacc cgctggtgcg caaactgtcg tttaccggtt cgaccgaaat tggccgccag     720

ttaatggaac aatgcgcgaa agacatcaaa aaagtgtcgc tggagctcgg cggcaacgcg     780

ccgtttatcg tctttgacga tgccgacctc gacaaagccg tggaaggcgc gctggcctcg     840

aaattccgca acgccgggca aacctgcgtc tgcgccaacc gtttatacgt gcaggacggc     900

gtgtatgacc gctttgccga aaaattgcag caggcggtga gcaaactgca catcggcgac     960

gggctggata aaggcgtcac catcgggccg ctgatcgatg aaaaagcagt agcaaaagtg    1020

gaagagcata ttgccgatgc gctggagaaa ggcgcgcgcg tggtttgcgg cggtaaagca    1080

cacgaacgtg gcggcaactt cttccagccg accattctgg tggacgttcc ggccaacgct    1140

aaagtgtcga aagaagagac gttcggcccc ctcgccccgc tgttccgttt taaagatgaa    1200

gccgatgtga tcgcgcaagc caatgacacc gaatttggtc ttgccgccta tttctacgcc    1260

cgtgatttaa gccgcgtctt ccgcgtgggc gaagcgctgg agtacggcat cgtcggcatc    1320

aataccggga ttatttccaa tgaagtggcc ccgttcggcg gcatcaaagc ctcgggtctg    1380

ggtcgtgaag gttcgaagta tggcatcgaa gattacttag aaatcaaata tatgtgcatc    1440

ggtctttaa                                                            1449
```

```
<210> SEQ ID NO 27
<211> LENGTH: 474
<212> TYPE: PRT
<213> ORGANISM: Klebsiella pneumoniae

<400> SEQUENCE: 27

Met Ser Thr Glu Ile Lys Thr Gln Val Val Val Leu Gly Ala Gly Pro
1               5                   10                  15

Ala Gly Tyr Ser Ala Ala Phe Arg Cys Ala Asp Leu Gly Leu Glu Thr
            20                  25                  30

Val Ile Val Glu Arg Tyr Ser Thr Leu Gly Gly Val Cys Leu Asn Val
        35                  40                  45

Gly Cys Ile Pro Ser Lys Ala Leu Leu His Val Ala Lys Val Ile Glu
    50                  55                  60

Glu Ala Lys Ala Leu Ala Glu His Gly Ile Val Phe Gly Glu Pro Lys
65                  70                  75                  80

Thr Asp Ile Asp Lys Ile Arg Thr Trp Lys Glu Lys Val Ile Thr Gln
                85                  90                  95

Leu Thr Gly Gly Leu Ala Gly Met Ala Lys Gly Arg Lys Val Lys Val
            100                 105                 110

Val Asn Gly Leu Gly Lys Phe Thr Gly Ala Asn Thr Leu Glu Val Glu
        115                 120                 125

Gly Glu Asn Gly Lys Thr Val Ile Asn Phe Asp Asn Ala Ile Ile Ala
    130                 135                 140

Ala Gly Ser Arg Pro Ile Gln Leu Pro Phe Ile Pro His Glu Asp Pro
145                 150                 155                 160

Arg Val Trp Asp Ser Thr Asp Ala Leu Glu Leu Lys Ser Val Pro Lys
                165                 170                 175

Arg Met Leu Val Met Gly Gly Gly Ile Ile Gly Leu Glu Met Gly Thr
            180                 185                 190

Val Tyr His Ala Leu Gly Ser Glu Ile Asp Val Val Glu Met Phe Asp
        195                 200                 205

Gln Val Ile Pro Ala Ala Asp Lys Asp Val Val Lys Val Phe Thr Lys
    210                 215                 220

Arg Ile Ser Lys Lys Phe Asn Leu Met Leu Glu Thr Lys Val Thr Ala
```

```
225                 230                 235                 240

Val Glu Ala Lys Glu Asp Gly Ile Tyr Val Ser Met Glu Gly Lys Lys
                245                 250                 255

Ala Pro Ala Glu Ala Gln Arg Tyr Asp Ala Val Leu Val Ala Ile Gly
            260                 265                 270

Arg Val Pro Asn Gly Lys Asn Leu Asp Ala Gly Lys Ala Gly Val Glu
        275                 280                 285

Val Asp Asp Arg Gly Phe Ile Arg Val Asp Lys Gln Met Arg Thr Asn
    290                 295                 300

Val Pro His Ile Phe Ala Ile Gly Asp Ile Val Gly Gln Pro Met Leu
305                 310                 315                 320

Ala His Lys Gly Val His Glu Gly His Val Ala Ala Glu Val Ile Ser
                325                 330                 335

Gly Leu Lys His Tyr Phe Asp Pro Lys Val Ile Pro Ser Ile Ala Tyr
            340                 345                 350

Thr Glu Pro Glu Val Ala Trp Val Gly Leu Thr Glu Lys Glu Ala Lys
        355                 360                 365

Glu Lys Gly Ile Ser Tyr Glu Thr Ala Thr Phe Pro Trp Ala Ala Ser
    370                 375                 380

Gly Arg Ala Ile Ala Ser Asp Cys Ala Asp Gly Met Thr Lys Leu Ile
385                 390                 395                 400

Phe Asp Lys Glu Thr His Arg Val Ile Gly Gly Ala Ile Val Gly Thr
                405                 410                 415

Asn Gly Gly Glu Leu Leu Gly Glu Ile Gly Leu Ala Ile Glu Met Gly
            420                 425                 430

Cys Asp Ala Glu Asp Ile Ala Leu Thr Ile His Ala His Pro Thr Leu
        435                 440                 445

His Glu Ser Val Gly Leu Ala Ala Glu Val Phe Glu Gly Ser Ile Thr
    450                 455                 460

Asp Leu Pro Asn Ala Lys Ala Lys Lys Lys
465                 470
```

<210> SEQ ID NO 28
<211> LENGTH: 1425
<212> TYPE: DNA
<213> ORGANISM: Klebsiella pneumoniae

<400> SEQUENCE: 28

```
atgagtactg aaatcaaaac tcaggtcgtg gtacttgggg caggccccgc aggttactct      60

gcagccttcc gttgcgctga tttaggtctg gaaaccgtca tcgtagaacg ttacagcacc     120

ctcggtggtg tttgtctgaa cgtgggttgt atcccttcta aagcgctgct gcacgtggca     180

aaagttatcg aagaagcgaa agcgctggcc gaacacggca tcgttttcgg cgaaccgaaa     240

actgacattg acaagatccg cacctggaaa gaaaaagtca tcactcagct gaccggtggt     300

ctggctggca tggccaaagg tcgtaaagtg aaggtggtta acggtctggg taaatttacc     360

ggcgctaaca ccctggaagt ggaaggcgaa aacggcaaaa ccgtgatcaa cttcgacaac     420

gccatcatcg cggcgggttc ccgtccgatt cagctgccgt ttatcccgca tgaagatccg     480

cgcgtatggg actccaccga cgcgctggaa ctgaaatctg taccgaaacg catgctggtg     540

atgggcggcg gtatcatcgg tctggaaatg ggtaccgtat accatgcgct gggttcagag     600

attgacgtgg tggaaatgtt cgaccaggtt atcccggctg ccgacaaaga cgtggtgaaa     660

gtcttcacca aacgcatcag caagaaattt aacctgatgc tggaaaccaa agtgactgcc     720
```

```
gttgaagcga aagaagacgg tatttacgtt tccatggaag gtaaaaaagc accggcggaa    780

gcgcagcgtt acgacgcagt gctggtcgct atcggccgcg taccgaatgg taaaaacctc    840

gatgcaggta aagctggcgt ggaagttgac gatcgcggct tcatccgcgt tgacaaacaa    900

atgcgcacca acgtgccgca catctttgct atcggcgata tcgtcggtca gccgatgctg    960

gcgcacaaag gtgtccatga aggccacgtt gccgcagaag ttatctccgg tctgaaacac   1020

tacttcgatc cgaaagtgat cccatccatc gcctacactg aaccagaagt ggcatgggtc   1080

ggtctgaccg agaaagaagc gaaagagaaa ggcatcagct acgaaaccgc caccttcccg   1140

tgggctgctt ccggccgtgc tatcgcttct gactgcgcag atggtatgac caaactgatc   1200

ttcgacaaag agacccaccg tgttatcggc ggcgcgattg tcggcaccaa cggcggcgag   1260

ctgctgggtg agatcggcct ggctatcgag atgggctgtg acgctgaaga catcgccctg   1320

accatccacg ctcacccgac tctgcacgag tccgttggcc tggcggcgga agtgttcgaa   1380

ggcagcatca ccgacctgcc aaacgccaaa gcgaagaaaa agtaa                   1425


<210> SEQ ID NO 29
<211> LENGTH: 474
<212> TYPE: PRT
<213> ORGANISM: Artificial Sequence
<220> FEATURE:
<223> OTHER INFORMATION: Synthetic LpdA mutant

<400> SEQUENCE: 29

Met Ser Thr Glu Ile Lys Thr Gln Val Val Val Leu Gly Ala Gly Pro
1               5                   10                  15

Ala Gly Tyr Ser Ala Ala Phe Arg Cys Ala Asp Leu Gly Leu Glu Thr
            20                  25                  30

Val Ile Val Glu Arg Tyr Ser Thr Leu Gly Gly Val Cys Leu Asn Val
        35                  40                  45

Gly Cys Ile Pro Ser Lys Ala Leu Leu His Val Ala Lys Val Ile Glu
    50                  55                  60

Glu Ala Lys Ala Leu Ala Glu His Gly Ile Val Phe Gly Glu Pro Lys
65                  70                  75                  80

Thr Asp Ile Asp Lys Ile Arg Thr Trp Lys Glu Lys Val Ile Thr Gln
                85                  90                  95

Leu Thr Gly Gly Leu Ala Gly Met Ala Lys Gly Arg Lys Val Lys Val
            100                 105                 110

Val Asn Gly Leu Gly Lys Phe Thr Gly Ala Asn Thr Leu Glu Val Glu
        115                 120                 125

Gly Glu Asn Gly Lys Thr Val Ile Asn Phe Asp Asn Ala Ile Ile Ala
    130                 135                 140

Ala Gly Ser Arg Pro Ile Gln Leu Pro Phe Ile Pro His Glu Asp Pro
145                 150                 155                 160

Arg Val Trp Asp Ser Thr Asp Ala Leu Glu Leu Lys Ser Val Pro Lys
                165                 170                 175

Arg Met Leu Val Met Gly Gly Gly Ile Ile Gly Leu Glu Met Gly Thr
            180                 185                 190

Val Tyr His Ala Leu Gly Ser Glu Ile Asp Val Val Glu Met Phe Asp
        195                 200                 205

Gln Val Ile Pro Ala Ala Asp Lys Asp Val Val Lys Val Phe Thr Lys
    210                 215                 220

Arg Ile Ser Lys Lys Phe Asn Leu Met Leu Glu Thr Lys Val Thr Ala
225                 230                 235                 240
```

```
Val Glu Ala Lys Glu Asp Gly Ile Tyr Val Ser Met Glu Gly Lys Lys
                245                 250                 255

Ala Pro Ala Glu Ala Gln Arg Tyr Asp Ala Val Leu Val Ala Ile Gly
            260                 265                 270

Arg Val Pro Asn Gly Lys Asn Leu Asp Ala Gly Lys Ala Gly Val Glu
        275                 280                 285

Val Asp Asp Arg Gly Phe Ile Arg Val Asp Lys Gln Met Arg Thr Asn
    290                 295                 300

Val Pro His Ile Phe Ala Ile Gly Asp Ile Val Gly Gln Pro Met Leu
305                 310                 315                 320

Ala His Lys Gly Val His Glu Gly His Val Ala Ala Glu Val Ile Ser
                325                 330                 335

Gly Leu Lys His Tyr Phe Asp Pro Lys Val Ile Pro Ser Ile Ala Tyr
            340                 345                 350

Thr Lys Pro Glu Val Ala Trp Val Gly Leu Thr Glu Lys Glu Ala Lys
        355                 360                 365

Glu Lys Gly Ile Ser Tyr Glu Thr Ala Thr Phe Pro Trp Ala Ala Ser
    370                 375                 380

Gly Arg Ala Ile Ala Ser Asp Cys Ala Asp Gly Met Thr Lys Leu Ile
385                 390                 395                 400

Phe Asp Lys Glu Thr His Arg Val Ile Gly Gly Ala Ile Val Gly Thr
                405                 410                 415

Asn Gly Gly Glu Leu Leu Gly Glu Ile Gly Leu Ala Ile Glu Met Gly
            420                 425                 430

Cys Asp Ala Glu Asp Ile Ala Leu Thr Ile His Ala His Pro Thr Leu
        435                 440                 445

His Glu Ser Val Gly Leu Ala Ala Glu Val Phe Glu Gly Ser Ile Thr
    450                 455                 460

Asp Leu Pro Asn Ala Lys Ala Lys Lys Lys
465                 470
```

```
<210> SEQ ID NO 30
<211> LENGTH: 1425
<212> TYPE: DNA
<213> ORGANISM: Artificial Sequence
<220> FEATURE:
<223> OTHER INFORMATION: Synthetic lpdA mutant

<400> SEQUENCE: 30

atgagtactg aaatcaaaac tcaggtcgtg gtacttgggg caggccccgc aggttactct      60

gcagccttcc gttgcgctga tttaggtctg gaaaccgtca tcgtagaacg ttacagcacc     120

ctcggtggtg tttgtctgaa cgtgggttgt atcccttcta aagcgctgct gcacgtggca     180

aaagttatcg aagaagcgaa agcgctggcc gaacacggca tcgttttcgg cgaaccgaaa     240

actgacattg acaagatccg cacctggaaa gaaaaagtca tcactcagct gaccggtggt     300

ctggctggca tggccaaagg tcgtaaagtg aaggtggtta acggtctggg taaatttacc     360

ggcgctaaca ccctggaagt ggaaggcgaa aacggcaaaa ccgtgatcaa cttcgacaac     420

gccatcatcg cggcgggttc ccgtccgatt cagctgccgt ttatcccgca tgaagatccg     480

cgcgtatggg actccaccga cgcgctggaa ctgaaatctg taccgaaacg catgctggtg     540

atgggcggcg gtatcatcgg tctggaaatg ggtaccgtat accatgcgct gggttcagag     600

attgacgtgg tggaaatgtt cgaccaggtt atcccggctg ccgacaaaga cgtggtgaaa     660

gtcttcacca aacgcatcag caagaaattt aacctgatgc tggaaaccaa agtgactgcc     720
```

```
gttgaagcga aagaagacgg tatttacgtt tccatggaag gtaaaaaagc accggcggaa    780

gcgcagcgtt acgacgcagt gctggtcgct atcggccgcg taccgaatgg taaaaacctc    840

gatgcaggta aagctggcgt ggaagttgac gatcgcggct tcatccgcgt tgacaaacaa    900

atgcgcacca acgtgccgca catctttgct atcggcgata tcgtcggtca gccgatgctg    960

gcgcacaaag gtgtccatga aggccacgtt gccgcagaag ttatctccgg tctgaaacac   1020

tacttcgatc cgaaagtgat cccatccatc gcctacacta agccagaagt ggcatgggtc   1080

ggtctgaccg agaaagaagc gaaagagaaa ggcatcagct acgaaaccgc caccttcccg   1140

tgggctgctt ccggccgtgc tatcgcttct gactgcgcag atggtatgac caaactgatc   1200

ttcgacaaag agacccaccg tgttatcggc ggcgcgattg tcggcaccaa cggcggcgag   1260

ctgctgggtg agatcggcct ggctatcgag atgggctgtg acgctgaaga catcgccctg   1320

accatccacg ctcacccgac tctgcacgag tccgttggcc tggcggcgga agtgttcgaa   1380

ggcagcatca ccgacctgcc aaacgccaaa gcgaagaaaa agtaa                   1425
```

<210> SEQ ID NO 31
<211> LENGTH: 427
<212> TYPE: PRT
<213> ORGANISM: Escherichia coli

<400> SEQUENCE: 31

```
Met Ala Asp Thr Lys Ala Lys Leu Thr Leu Asn Gly Asp Thr Ala Val
  1               5                  10                  15

Glu Leu Asp Val Leu Lys Gly Thr Leu Gly Gln Asp Val Ile Asp Ile
             20                  25                  30

Arg Thr Leu Gly Ser Lys Gly Val Phe Thr Phe Asp Pro Gly Phe Thr
         35                  40                  45

Ser Thr Ala Ser Cys Glu Ser Lys Ile Thr Phe Ile Asp Gly Asp Glu
     50                  55                  60

Gly Ile Leu Leu His Arg Gly Phe Pro Ile Asp Gln Leu Ala Thr Asp
 65                  70                  75                  80

Ser Asn Tyr Leu Glu Val Cys Tyr Ile Leu Leu Asn Gly Glu Lys Pro
                 85                  90                  95

Thr Gln Glu Gln Tyr Asp Glu Phe Lys Thr Thr Val Thr Arg His Thr
            100                 105                 110

Met Ile His Glu Gln Ile Thr Arg Leu Phe His Ala Phe Arg Arg Asp
        115                 120                 125

Ser His Pro Met Ala Val Met Cys Gly Ile Thr Gly Ala Leu Ala Ala
    130                 135                 140

Phe Tyr His Asp Ser Leu Asp Val Asn Asn Pro Arg His Arg Glu Ile
145                 150                 155                 160

Ala Ala Phe Arg Leu Leu Ser Lys Met Pro Thr Met Ala Ala Met Cys
                165                 170                 175

Tyr Lys Tyr Ser Ile Gly Gln Pro Phe Val Tyr Pro Arg Asn Asp Leu
            180                 185                 190

Ser Tyr Ala Gly Asn Phe Leu Asn Met Met Phe Ser Thr Pro Cys Glu
        195                 200                 205

Pro Tyr Glu Val Asn Pro Ile Leu Glu Arg Ala Met Asp Arg Ile Leu
    210                 215                 220

Ile Leu His Ala Asp His Glu Gln Asn Ala Ser Thr Ser Thr Val Arg
225                 230                 235                 240

Thr Ala Gly Ser Ser Gly Ala Asn Pro Phe Ala Cys Ile Ala Ala Gly
                245                 250                 255
```

```
Ile Ala Ser Leu Trp Gly Pro Ala His Gly Gly Ala Asn Glu Ala Ala
            260                 265                 270

Leu Lys Met Leu Glu Glu Ile Ser Ser Val Lys His Ile Pro Glu Phe
        275                 280                 285

Val Arg Arg Ala Lys Asp Lys Asn Asp Ser Phe Arg Leu Met Gly Phe
    290                 295                 300

Gly His Arg Val Tyr Lys Asn Tyr Asp Pro Arg Ala Thr Val Met Arg
305                 310                 315                 320

Glu Thr Cys His Glu Val Leu Lys Glu Leu Gly Thr Lys Asp Asp Leu
                325                 330                 335

Leu Glu Val Ala Met Glu Leu Glu Asn Ile Ala Leu Asn Asp Pro Tyr
            340                 345                 350

Phe Ile Glu Lys Lys Leu Tyr Pro Asn Val Asp Phe Tyr Ser Gly Ile
        355                 360                 365

Ile Leu Lys Ala Met Gly Ile Pro Ser Ser Met Phe Thr Val Ile Phe
    370                 375                 380

Ala Met Ala Arg Thr Val Gly Trp Ile Ala His Trp Ser Glu Met His
385                 390                 395                 400

Ser Asp Gly Met Lys Ile Ala Arg Pro Arg Gln Leu Tyr Thr Gly Tyr
                405                 410                 415

Glu Lys Arg Asp Phe Lys Ser Asp Ile Lys Arg
            420                 425


<210> SEQ ID NO 32
<211> LENGTH: 1284
<212> TYPE: DNA
<213> ORGANISM: Escherichia coli

<400> SEQUENCE: 32

atggctgata caaaagcaaa actcaccctc aacggggaca cagctgttga actggatgtg     60

ctgaaaggca cgctgggtca agatgttatt gatatccgta ctctcggttc aaaaggtgtg    120

ttcacctttg acccaggctt cacttcaacc gcatcctgcg aatctaaaat tacttttatt    180

gatggtgatg aaggtatttt gctgcaccgc ggtttcccga tcgatcagct ggcgaccgat    240

tctaactacc tggaagtttg ttacatcctg ctgaatggtg aaaaaccgac tcaggaacag    300

tatgacgaat ttaaaactac ggtgacccgt cataccatga tccacgagca gattacccgt    360

ctgttccacg ctttccgtcg cgactcacat ccaatggcag tcatgtgtgg tattaccggc    420

gcgctggcgg cgttctatca cgactcgctg gatgttaaca atcctcgtca tcgtgaaatt    480

gccgcgttcc gcctgctgtc gaaaatgccg accatggccg cgatgtgtta caagtattcc    540

attggtcagc catttgttta tccgcgcaac gatctctcct atgccggtaa cttcctgaat    600

atgatgttct ccacgccgtg cgaaccgtat gaagttaatc cgattctgga acgtgctatg    660

gaccgtattc tgatcctgca cgctgaccat gaacagaacg cctctacctc caccgtgcgt    720

accgctggct cttcgggtgc gaacccgttt gcctgtatcg cagcaggtat tgcttcactg    780

tggggacctg cgcacggtgg tgctaacgaa gcggcgctga aaatgctgga agaaattagc    840

tccgttaaac acattccgga atttgttcgt cgtgcgaaag ataaaaatga ttctttccgc    900

ctgatgggct tcggtcaccg cgtgtacaaa aattacgacc cgcgcgccac cgtaatgcgt    960

gaaacctgcc atgaagttct gaaagagctg ggcaccaaag atgacctgct ggaagtggct   1020

atggagctgg aaaacatcgc gctgaacgac ccgtacttta tcgagaagaa actgtacccg   1080

aacgtcgatt tctactctgg tatcatcctg aaagcgatgg gtattccgtc ttccatgttc   1140
```

```
accgtcattt tcgcaatggc acgtaccgtt ggctggatcg cccactggag cgaaatgcac   1200

agtgacggta tgaagattgc ccgtccgcgt cagctgtata caggatatga aaaacgcgac   1260

tttaaaagcg atatcaagcg ttaa                                          1284


<210> SEQ ID NO 33
<211> LENGTH: 427
<212> TYPE: PRT
<213> ORGANISM: Artificial Sequence
<220> FEATURE:
<223> OTHER INFORMATION: Synthetic GltA mutant

<400> SEQUENCE: 33

Met Ala Asp Thr Lys Ala Lys Leu Thr Leu Asn Gly Asp Thr Ala Val
  1               5                  10                  15

Glu Leu Asp Val Leu Lys Gly Thr Leu Gly Gln Asp Val Ile Asp Ile
             20                  25                  30

Arg Thr Leu Gly Ser Lys Gly Val Phe Thr Phe Asp Pro Gly Phe Thr
         35                  40                  45

Ser Thr Ala Ser Cys Glu Ser Lys Ile Thr Phe Ile Asp Gly Asp Glu
     50                  55                  60

Gly Ile Leu Leu His Arg Gly Phe Pro Ile Asp Gln Leu Ala Thr Asp
 65                  70                  75                  80

Ser Asn Tyr Leu Glu Val Cys Tyr Ile Leu Leu Asn Gly Glu Lys Pro
                 85                  90                  95

Thr Gln Glu Gln Tyr Asp Glu Phe Lys Thr Thr Val Thr Arg His Thr
            100                 105                 110

Met Ile His Glu Gln Ile Thr Arg Leu Phe His Ala Phe Arg Arg Asp
        115                 120                 125

Ser His Pro Met Ala Val Met Cys Gly Ile Thr Gly Ala Leu Ala Ala
    130                 135                 140

Phe Tyr His Asp Ser Leu Asp Val Asn Asn Pro Arg His Arg Glu Ile
145                 150                 155                 160

Ala Ala Phe Leu Leu Leu Ser Lys Met Pro Thr Met Ala Ala Met Cys
                165                 170                 175

Tyr Lys Tyr Ser Ile Gly Gln Pro Phe Val Tyr Pro Arg Asn Asp Leu
            180                 185                 190

Ser Tyr Ala Gly Asn Phe Leu Asn Met Met Phe Ser Thr Pro Cys Glu
        195                 200                 205

Pro Tyr Glu Val Asn Pro Ile Leu Glu Arg Ala Met Asp Arg Ile Leu
    210                 215                 220

Ile Leu His Ala Asp His Glu Gln Asn Ala Ser Thr Ser Thr Val Arg
225                 230                 235                 240

Thr Ala Gly Ser Ser Gly Ala Asn Pro Phe Ala Cys Ile Ala Ala Gly
                245                 250                 255

Ile Ala Ser Leu Trp Gly Pro Ala His Gly Gly Ala Asn Glu Ala Ala
            260                 265                 270

Leu Lys Met Leu Glu Glu Ile Ser Ser Val Lys His Ile Pro Glu Phe
        275                 280                 285

Val Arg Arg Ala Lys Asp Lys Asn Asp Ser Phe Arg Leu Met Gly Phe
    290                 295                 300

Gly His Arg Val Tyr Lys Asn Tyr Asp Pro Arg Ala Thr Val Met Arg
305                 310                 315                 320

Glu Thr Cys His Glu Val Leu Lys Glu Leu Gly Thr Lys Asp Asp Leu
                325                 330                 335
```

```
Leu Glu Val Ala Met Glu Leu Glu Asn Ile Ala Leu Asn Asp Pro Tyr
            340                 345                 350

Phe Ile Glu Lys Lys Leu Tyr Pro Asn Val Asp Phe Tyr Ser Gly Ile
        355                 360                 365

Ile Leu Lys Ala Met Gly Ile Pro Ser Ser Met Phe Thr Val Ile Phe
    370                 375                 380

Ala Met Ala Arg Thr Val Gly Trp Ile Ala His Trp Ser Glu Met His
385                 390                 395                 400

Ser Asp Gly Met Lys Ile Ala Arg Pro Arg Gln Leu Tyr Thr Gly Tyr
                405                 410                 415

Glu Lys Arg Asp Phe Lys Ser Asp Ile Lys Arg
            420                 425


<210> SEQ ID NO 34
<211> LENGTH: 1284
<212> TYPE: DNA
<213> ORGANISM: Artificial Sequence
<220> FEATURE:
<223> OTHER INFORMATION: Synthetic gltA mutant

<400> SEQUENCE: 34

atggctgata caaaagcaaa actcaccctc aacggggaca cagctgttga actggatgtg     60

ctgaaaggca cgctgggtca agatgttatt gatatccgta ctctcggttc aaaaggtgtg    120

ttcacctttg acccaggctt cacttcaacc gcatcctgcg aatctaaaat tacttttatt    180

gatggtgatg aaggtatttt gctgcaccgc ggtttcccga tcgatcagct ggcgaccgat    240

tctaactacc tggaagtttg ttacatcctg ctgaatggtg aaaaaccgac tcaggaacag    300

tatgacgaat ttaaaactac ggtgacccgt cataccatga tccacgagca gattacccgt    360

ctgttccacg ctttccgtcg cgactcacat ccaatggcag tcatgtgtgg tattaccggc    420

gcgctggcgg cgttctatca cgactcgctg gatgttaaca atcctcgtca tcgtgaaatt    480

gccgcgttcc tcctgctgtc gaaaatgccg accatggccg cgatgtgtta caagtattcc    540

attggtcagc catttgttta tccgcgcaac gatctctcct atgccggtaa cttcctgaat    600

atgatgttct ccacgccgtg cgaaccgtat gaagttaatc cgattctgga acgtgctatg    660

gaccgtattc tgatcctgca cgctgaccat gaacagaacg cctctacctc caccgtgcgt    720

accgctggct cttcgggtgc gaacccgttt gcctgtatcg cagcaggtat tgcttcactg    780

tggggacctg cgcacggtgg tgctaacgaa gcggcgctga aaatgctgga agaaattagc    840

tccgttaaac acattccgga atttgttcgt cgtgcgaaag ataaaaatga ttctttccgc    900

ctgatgggct tcggtcaccg cgtgtacaaa aattacgacc cgcgcgccac cgtaatgcgt    960

gaaacctgcc atgaagttct gaaagagctg ggcaccaaag atgacctgct ggaagtggct   1020

atggagctgg aaaacatcgc gctgaacgac ccgtacttta tcgagaagaa actgtacccg   1080

aacgtcgatt tctactctgg tatcatcctg aaagcgatgg gtattccgtc ttccatgttc   1140

accgtcattt tcgcaatggc acgtaccgtt ggctggatcg cccactggag cgaaatgcac   1200

agtgacggta tgaagattgc ccgtccgcgt cagctgtata caggatatga aaaacgcgac   1260

tttaaaagcg atatcaagcg ttaa                                          1284


<210> SEQ ID NO 35
<211> LENGTH: 71
<212> TYPE: DNA
<213> ORGANISM: Artificial Sequence
<220> FEATURE:
```

<223> OTHER INFORMATION: Synthetic ldhA KO f

<400> SEQUENCE: 35
atgaaactcg ccgtttatag cacaaaacag tacgacaaga agtacctgca taggtgacac 60
tatagaacgc g 71

<210> SEQ ID NO 36
<211> LENGTH: 70
<212> TYPE: DNA
<213> ORGANISM: Artificial Sequence
<220> FEATURE:
<223> OTHER INFORMATION: Synthetic ldhA KO r

<400> SEQUENCE: 36
ttaaaccagt tcgttcgggc aggtttcgcc tttttccaga ttgcttaagt tagtggatct 60
gatgggtacc 70

<210> SEQ ID NO 37
<211> LENGTH: 20
<212> TYPE: DNA
<213> ORGANISM: Artificial Sequence
<220> FEATURE:
<223> OTHER INFORMATION: Synthetic ldhA KO CUP

<400> SEQUENCE: 37
tacactaagc atagttgttg 20

<210> SEQ ID NO 38
<211> LENGTH: 20
<212> TYPE: DNA
<213> ORGANISM: Artificial Sequence
<220> FEATURE:
<223> OTHER INFORMATION: Synthetic ldhA KO CDO

<400> SEQUENCE: 38
ctttcttcat tgtggttctc 20

<210> SEQ ID NO 39
<211> LENGTH: 71
<212> TYPE: DNA
<213> ORGANISM: Artificial Sequence
<220> FEATURE:
<223> OTHER INFORMATION: Synthetic pflB KO f

<400> SEQUENCE: 39
atgtccgagc ttaatgaaaa gttagccaca gcctgggaag gttttaccaa taggtgacac 60
tatagaacgc g 71

<210> SEQ ID NO 40
<211> LENGTH: 70
<212> TYPE: DNA
<213> ORGANISM: Artificial Sequence
<220> FEATURE:
<223> OTHER INFORMATION: Synthetic pflB KO r

<400> SEQUENCE: 40
ttacatagat tgagtgaagg tacgagtaat aacgtcctgc tgctgttctt tagtggatct 60
gatgggtacc 70

<210> SEQ ID NO 41
<211> LENGTH: 20
<212> TYPE: DNA
<213> ORGANISM: Artificial Sequence
<220> FEATURE:
<223> OTHER INFORMATION: Synthetic pflB KO CUP

<400> SEQUENCE: 41
gggtcattta cctgcgtgaa 20

<210> SEQ ID NO 42
<211> LENGTH: 20
<212> TYPE: DNA
<213> ORGANISM: Artificial Sequence
<220> FEATURE:
<223> OTHER INFORMATION: Synthetic pflB KO CDO

<400> SEQUENCE: 42
agtctgtttt ggcagtcacc 20

<210> SEQ ID NO 43
<211> LENGTH: 71
<212> TYPE: DNA
<213> ORGANISM: Artificial Sequence
<220> FEATURE:
<223> OTHER INFORMATION: Synthetic adhE KO f

<400> SEQUENCE: 43
atggctgtta ctaatgtcgc tgaacttaac gcactcgtag agcgtgtaaa taggtgacac 60
tatagaacgc g 71

<210> SEQ ID NO 44
<211> LENGTH: 70
<212> TYPE: DNA
<213> ORGANISM: Artificial Sequence
<220> FEATURE:
<223> OTHER INFORMATION: Synthetic adhE KO r

<400> SEQUENCE: 44
ttaagcggat tttttcgctt ttttctcagc tttagccgga gcggcttctt tagtggatct 60
gatgggtacc 70

<210> SEQ ID NO 45
<211> LENGTH: 20
<212> TYPE: DNA
<213> ORGANISM: Artificial Sequence
<220> FEATURE:
<223> OTHER INFORMATION: Synthetic adhE KO CUP

<400> SEQUENCE: 45
caccgcactg actatactct 20

<210> SEQ ID NO 46
<211> LENGTH: 20
<212> TYPE: DNA
<213> ORGANISM: Artificial Sequence
<220> FEATURE:
<223> OTHER INFORMATION: Synthetic adhE KO CDO

<400> SEQUENCE: 46
gatgaaggct aatgctgtcg 20

<210> SEQ ID NO 47
<211> LENGTH: 71
<212> TYPE: DNA
<213> ORGANISM: Artificial Sequence
<220> FEATURE:
<223> OTHER INFORMATION: Synthetic mdh KO f

```
<400> SEQUENCE: 47

atgaaagtcg cagtcctcgg cgctgctggc ggtattggcc aggcgcttgc taggtgacac     60

tatagaacgc g                                                          71


<210> SEQ ID NO 48
<211> LENGTH: 70
<212> TYPE: DNA
<213> ORGANISM: Artificial Sequence
<220> FEATURE:
<223> OTHER INFORMATION: Synthetic mdh KO r

<400> SEQUENCE: 48

ttacttatta acgaactctt cgcccagggc gatatctttc ttcagcgtat tagtggatct     60

gatgggtacc                                                            70


<210> SEQ ID NO 49
<211> LENGTH: 20
<212> TYPE: DNA
<213> ORGANISM: Artificial Sequence
<220> FEATURE:
<223> OTHER INFORMATION: Synthetic mdh KO CUP

<400> SEQUENCE: 49

ggttcctgat tacggcaatt                                                 20


<210> SEQ ID NO 50
<211> LENGTH: 20
<212> TYPE: DNA
<213> ORGANISM: Artificial Sequence
<220> FEATURE:
<223> OTHER INFORMATION: Synthetic mdh KO CDO

<400> SEQUENCE: 50

attcaggaat atccggcaac                                                 20


<210> SEQ ID NO 51
<211> LENGTH: 71
<212> TYPE: DNA
<213> ORGANISM: Artificial Sequence
<220> FEATURE:
<223> OTHER INFORMATION: Synthetic arcA KO f

<400> SEQUENCE: 51

atgcagaccc cgcacattct tatcgttgaa gacgagttgg taacacgcaa taggtgacac     60

tatagaacgc g                                                          71


<210> SEQ ID NO 52
<211> LENGTH: 70
<212> TYPE: DNA
<213> ORGANISM: Artificial Sequence
<220> FEATURE:
<223> OTHER INFORMATION: Synthetic arcA KO r

<400> SEQUENCE: 52

ttaatcttcc agatcaccac agaagcgata accttcaccg tggatggtgg tagtggatct     60

gatgggtacc                                                            70


<210> SEQ ID NO 53
<211> LENGTH: 20
<212> TYPE: DNA
<213> ORGANISM: Artificial Sequence
<220> FEATURE:
<223> OTHER INFORMATION: Synthetic arcA KO CUP
```

<400> SEQUENCE: 53
ttgacgttga tggaaagtgc 20

<210> SEQ ID NO 54
<211> LENGTH: 20
<212> TYPE: DNA
<213> ORGANISM: Artificial Sequence
<220> FEATURE:
<223> OTHER INFORMATION: Synthetic arcA KO CDO

<400> SEQUENCE: 54
ccgaaaatga aagccagtaa 20

<210> SEQ ID NO 55
<211> LENGTH: 71
<212> TYPE: DNA
<213> ORGANISM: Artificial Sequence
<220> FEATURE:
<223> OTHER INFORMATION: Synthetic sad KO f

<400> SEQUENCE: 55
atgaccatta ctccggcaac tcatgcaatt tcgataaatc ctgccacggg taggtgacac 60
tatagaacgc g 71

<210> SEQ ID NO 56
<211> LENGTH: 70
<212> TYPE: DNA
<213> ORGANISM: Artificial Sequence
<220> FEATURE:
<223> OTHER INFORMATION: Synthetic sad KO r

<400> SEQUENCE: 56
tcagatccgg tctttccaca ccgtctggat attacagaat tcgtgtaagc tagtggatct 60
gatgggtacc 70

<210> SEQ ID NO 57
<211> LENGTH: 20
<212> TYPE: DNA
<213> ORGANISM: Artificial Sequence
<220> FEATURE:
<223> OTHER INFORMATION: Synthetic sad KO CUP

<400> SEQUENCE: 57
tcgattcgtg aataagtggc 20

<210> SEQ ID NO 58
<211> LENGTH: 20
<212> TYPE: DNA
<213> ORGANISM: Artificial Sequence
<220> FEATURE:
<223> OTHER INFORMATION: Synthetic sad KO CDO

<400> SEQUENCE: 58
ccactttcta ctcctggacc 20

<210> SEQ ID NO 59
<211> LENGTH: 71
<212> TYPE: DNA
<213> ORGANISM: Artificial Sequence
<220> FEATURE:
<223> OTHER INFORMATION: Synthetic gabD KO f

<400> SEQUENCE: 59
atgaaactta acgacagtaa cttattccgc cagcaggcgt tgattaacgg taggtgacac 60
tatagaacgc g 71

<210> SEQ ID NO 60
<211> LENGTH: 70
<212> TYPE: DNA
<213> ORGANISM: Artificial Sequence
<220> FEATURE:
<223> OTHER INFORMATION: Synthetic gabD KO r

<400> SEQUENCE: 60
ttaaagaccg atgcacatat atttgatttc taagtaatct tcgatgccat tagtggatct 60
gatgggtacc 70

<210> SEQ ID NO 61
<211> LENGTH: 20
<212> TYPE: DNA
<213> ORGANISM: Artificial Sequence
<220> FEATURE:
<223> OTHER INFORMATION: Synthetic gabD KO CUP

<400> SEQUENCE: 61
cacgccgcat ttaatcaata 20

<210> SEQ ID NO 62
<211> LENGTH: 20
<212> TYPE: DNA
<213> ORGANISM: Artificial Sequence
<220> FEATURE:
<223> OTHER INFORMATION: Synthetic gabD KO CDO

<400> SEQUENCE: 62
ctctttattg ctgctcattc 20

<210> SEQ ID NO 63
<211> LENGTH: 28
<212> TYPE: DNA
<213> ORGANISM: Artificial Sequence
<220> FEATURE:
<223> OTHER INFORMATION: Synthetic K lpd F

<400> SEQUENCE: 63
ccatcgccta cactaagcca gaagtggc 28

<210> SEQ ID NO 64
<211> LENGTH: 28
<212> TYPE: DNA
<213> ORGANISM: Artificial Sequence
<220> FEATURE:
<223> OTHER INFORMATION: Synthetic K lpd R

<400> SEQUENCE: 64
gccacttctg gcttagtgta ggcgatgg 28

<210> SEQ ID NO 65
<211> LENGTH: 82
<212> TYPE: DNA
<213> ORGANISM: Artificial Sequence
<220> FEATURE:
<223> OTHER INFORMATION: Synthetic K lpd 3

<400> SEQUENCE: 65
gccgctgcgg cctgaaagac gacgggtatg accgccggag ataaatatat agaggtcatg 60
aactgtctgc ttacataaac ag 82

<210> SEQ ID NO 66
<211> LENGTH: 77
<212> TYPE: DNA
<213> ORGANISM: Artificial Sequence
<220> FEATURE:
<223> OTHER INFORMATION: Synthetic K lpd 4

<400> SEQUENCE: 66
taaaaaaagc ggcgtggtta gccgcttttt taattgccgg atgttccggc aaacgaacaa 60
ttggtcggtc atttcgc 77

<210> SEQ ID NO 67
<211> LENGTH: 90
<212> TYPE: DNA
<213> ORGANISM: Artificial Sequence
<220> FEATURE:
<223> OTHER INFORMATION: Synthetic K lpd 5

<400> SEQUENCE: 67
ccggatccgc cgctgcggcc tgaaagacga cgggtatgac cgccggagat aaatatatag 60
aggtcatgat gagtactgaa atcaaaactc 90

<210> SEQ ID NO 68
<211> LENGTH: 89
<212> TYPE: DNA
<213> ORGANISM: Artificial Sequence
<220> FEATURE:
<223> OTHER INFORMATION: Synthetic K lpd 6

<400> SEQUENCE: 68
gggtcgacta aaaaaagcgg cgtggttagc cgctttttta attgccggat gttccggcaa 60
acgaacaatt actttttctt cgctttggc 89

<210> SEQ ID NO 69
<211> LENGTH: 19
<212> TYPE: DNA
<213> ORGANISM: Artificial Sequence
<220> FEATURE:
<223> OTHER INFORMATION: Synthetic K lpd 7

<400> SEQUENCE: 69
catcattaac aacacgctg 19

<210> SEQ ID NO 70
<211> LENGTH: 19
<212> TYPE: DNA
<213> ORGANISM: Artificial Sequence
<220> FEATURE:
<223> OTHER INFORMATION: Synthetic K lpd 8

<400> SEQUENCE: 70
cgacagtaac catactgtc 19

<210> SEQ ID NO 71
<211> LENGTH: 17
<212> TYPE: DNA
<213> ORGANISM: Artificial Sequence
<220> FEATURE:
<223> OTHER INFORMATION: Synthetic gltA F

<400> SEQUENCE: 71
tcgacagcag gaggaac 17

<210> SEQ ID NO 72
<211> LENGTH: 17
<212> TYPE: DNA
<213> ORGANISM: Artificial Sequence
<220> FEATURE:
<223> OTHER INFORMATION: Synthetic gltA R

<400> SEQUENCE: 72
tcgacagcag gaggaac 17

<210> SEQ ID NO 73
<211> LENGTH: 80
<212> TYPE: DNA
<213> ORGANISM: Artificial Sequence
<220> FEATURE:
<223> OTHER INFORMATION: Synthetic gltA 3

<400> SEQUENCE: 73
gtgcgaaggc aaatttaagt tccggcagtc ttacgtaata aggcgctaag gagaccttaa 60
ctgtctgctt acataaacag 80

<210> SEQ ID NO 74
<211> LENGTH: 78
<212> TYPE: DNA
<213> ORGANISM: Artificial Sequence
<220> FEATURE:
<223> OTHER INFORMATION: Synthetic gltA 4

<400> SEQUENCE: 74
ataaaaatta acccgccatt tgaacggcgg gttaaaatat ttacaactta gcaatcaacc 60
attggtcggt catttcgc 78

<210> SEQ ID NO 75
<211> LENGTH: 67
<212> TYPE: DNA
<213> ORGANISM: Artificial Sequence
<220> FEATURE:
<223> OTHER INFORMATION: Synthetic gltA 5

<400> SEQUENCE: 75
gtgcgaaggc aaatttaagt tccggcagtc ttacgtaata aggcgctaag gagaccttaa 60
atggctg 67

<210> SEQ ID NO 76
<211> LENGTH: 78
<212> TYPE: DNA
<213> ORGANISM: Artificial Sequence
<220> FEATURE:
<223> OTHER INFORMATION: Synthetic gltA 6

<400> SEQUENCE: 76
ataaaaatta acccgccatt tgaacggcgg gttaaaatat ttacaactta gcaatcaacc 60
attaacgctt gatatcgc 78

<210> SEQ ID NO 77
<211> LENGTH: 21
<212> TYPE: DNA
<213> ORGANISM: Artificial Sequence
<220> FEATURE:
<223> OTHER INFORMATION: Synthetic gltA 7

<400> SEQUENCE: 77
ggacagttat tagtggtaga c 21

<210> SEQ ID NO 78
<211> LENGTH: 22
<212> TYPE: DNA
<213> ORGANISM: Artificial Sequence
<220> FEATURE:
<223> OTHER INFORMATION: Synthetic gltA 8

<400> SEQUENCE: 78
gatgtatttc acacggtgct tc 22

<210> SEQ ID NO 79
<211> LENGTH: 371
<212> TYPE: PRT
<213> ORGANISM: Porphyromonas gingivalis

<400> SEQUENCE: 79

```
Met Gln Leu Phe Lys Leu Lys Ser Val Thr His His Phe Asp Thr Phe
  1               5                  10                  15

Ala Glu Phe Ala Lys Glu Phe Cys Leu Gly Glu Arg Asp Leu Val Ile
             20                  25                  30

Thr Asn Glu Phe Ile Tyr Glu Pro Tyr Met Lys Ala Cys Gln Leu Pro
         35                  40                  45

Cys His Phe Val Met Gln Glu Lys Tyr Gly Gln Gly Glu Pro Ser Asp
     50                  55                  60

Glu Met Met Asn Asn Ile Leu Ala Asp Ile Arg Asn Ile Gln Phe Asp
 65                  70                  75                  80

Arg Val Ile Gly Ile Gly Gly Gly Thr Val Ile Asp Ile Ser Lys Leu
                 85                  90                  95

Phe Val Leu Lys Gly Leu Asn Asp Val Leu Asp Ala Phe Asp Arg Lys
            100                 105                 110

Ile Pro Leu Ile Lys Glu Lys Glu Leu Ile Ile Val Pro Thr Thr Cys
        115                 120                 125

Gly Thr Gly Ser Glu Val Thr Asn Ile Ser Ile Ala Glu Ile Lys Ser
    130                 135                 140

Arg His Thr Lys Met Gly Leu Ala Asp Asp Ala Ile Val Ala Asp His
145                 150                 155                 160

Ala Ile Ile Ile Pro Glu Leu Leu Lys Ser Leu Pro Phe His Phe Tyr
                165                 170                 175

Ala Cys Ser Ala Ile Asp Ala Leu Ile His Ala Ile Glu Ser Tyr Val
            180                 185                 190

Ser Pro Lys Ala Ser Pro Tyr Ser Arg Leu Phe Ser Glu Ala Ala Trp
        195                 200                 205

Asp Ile Ile Leu Glu Val Phe Lys Lys Ile Ala Glu His Gly Pro Glu
    210                 215                 220

Tyr Arg Phe Glu Lys Leu Gly Glu Met Ile Met Ala Ser Asn Tyr Ala
225                 230                 235                 240

Gly Ile Ala Phe Gly Asn Ala Gly Val Gly Ala Val His Ala Leu Ser
                245                 250                 255

Tyr Pro Leu Gly Gly Asn Tyr His Val Pro His Gly Glu Ala Asn Tyr
            260                 265                 270

Gln Phe Phe Thr Glu Val Phe Lys Val Tyr Gln Lys Lys Asn Pro Phe
        275                 280                 285

Gly Tyr Ile Val Glu Leu Asn Trp Lys Leu Ser Lys Ile Leu Asn Cys
    290                 295                 300

Gln Pro Glu Tyr Val Tyr Pro Lys Leu Asp Glu Leu Leu Gly Cys Leu
```

```
305                 310                 315                 320

Leu Thr Lys Lys Pro Leu His Glu Tyr Gly Met Lys Asp Glu Glu Val
                325                 330                 335

Arg Gly Phe Ala Glu Ser Val Leu Lys Thr Gln Gln Arg Leu Leu Ala
            340                 345                 350

Asn Asn Tyr Val Glu Leu Thr Val Asp Glu Ile Glu Gly Ile Tyr Arg
        355                 360                 365

Arg Leu Tyr
    370


<210> SEQ ID NO 80
<211> LENGTH: 1116
<212> TYPE: DNA
<213> ORGANISM: Porphyromonas gingivalis

<400> SEQUENCE: 80

atgcaactgt tcaaactgaa atcagtcaca catcacttcg atactttcgc ggaatttgcc     60

aaagagttct gtcttggaga acgtgattta gtaattacca acgaattcat ttacgaaccg    120

tatatgaagg catgtcagtt gccctgccat tttgttatgc aggagaaata tgggcaaggc    180

gagccatctg acgagatgat gaataacatc ttggcagaca tccgtaatat ccagtttgac    240

cgcgtgatcg gtattggggg tggtacggtt attgacatct cgaaattatt tgtgctgaaa    300

ggactaaatg atgtgctcga tgcgttcgat cgcaagatac cgctgattaa agagaaagaa    360

ctgatcattg tgcccaccac atgcgggacg ggtagcgagg tgacgaatat ttcgatcgcg    420

gagatcaaaa gccgtcatac caaaatgggt ttggctgacg atgctattgt tgcagaccac    480

gcgatcatca taccagagct tctgaaaagc ctgccgttcc atttttatgc atgcagtgca    540

atagatgctc tgatccatgc catcgagtca tatgtttctc ctaaagccag tccatattct    600

cgtctgttca gtgaggcggc atgggatatt atcctggagg tattcaagaa aatagccgaa    660

cacggccctg aataccgctt tgagaagctg ggagaaatga tcatggcctc caactatgct    720

ggtatagcct tcgggaatgc aggcgtgggt gccgttcacg ctctaagcta tccattggga    780

ggcaattatc atgtgccgca tggcgaggct aactatcagt tttttacaga ggtctttaaa    840

gtataccaaa agaaaaatcc tttcggctat atagtcgaac tcaactggaa gctgtccaag    900

attctgaact gtcagcctga atacgtctat ccgaaactgg atgagttact cggctgtctt    960

ctgaccaaaa aaccgctgca cgaatacggc atgaaagatg aagaggtacg tggatttgcg   1020

gaatcagtgc ttaagactca gcagcggttg ctcgcgaata attatgttga gcttactgtt   1080

gatgaaattg aaggtatcta cagacgactg tactaa                             1116


<210> SEQ ID NO 81
<211> LENGTH: 1214
<212> TYPE: PRT
<213> ORGANISM: Mycobacterium bovis

<400> SEQUENCE: 81

Met Tyr Arg Lys Phe Arg Asp Asp Pro Ser Ser Val Asp Pro Ser Trp
  1               5                  10                  15

His Glu Phe Leu Val Asp Tyr Ser Pro Glu Pro Thr Ser Gln Pro Ala
             20                  25                  30

Ala Glu Pro Thr Arg Val Thr Ser Pro Leu Val Ala Glu Arg Ala Ala
         35                  40                  45

Ala Ala Ala Pro Gln Ala Pro Pro Lys Pro Ala Asp Thr Ala Ala Ala
     50                  55                  60
```

```
Gly Asn Gly Val Val Ala Ala Leu Ala Ala Lys Thr Ala Val Pro Pro
 65                  70                  75                  80

Pro Ala Glu Gly Asp Glu Val Ala Val Leu Arg Gly Ala Ala Ala Ala
                 85                  90                  95

Val Val Lys Asn Met Ser Ala Ser Leu Glu Val Pro Thr Ala Thr Ser
            100                 105                 110

Val Arg Ala Val Pro Ala Lys Leu Leu Ile Asp Asn Arg Ile Val Ile
        115                 120                 125

Asn Asn Gln Leu Lys Arg Thr Arg Gly Gly Lys Ile Ser Phe Thr His
    130                 135                 140

Leu Leu Gly Tyr Ala Leu Val Gln Ala Val Lys Lys Phe Pro Asn Met
145                 150                 155                 160

Asn Arg His Tyr Thr Glu Val Asp Gly Lys Pro Thr Ala Val Thr Pro
                165                 170                 175

Ala His Thr Asn Leu Gly Leu Ala Ile Asp Leu Gln Gly Lys Asp Gly
            180                 185                 190

Lys Arg Ser Leu Val Val Ala Gly Ile Lys Arg Cys Glu Thr Met Arg
        195                 200                 205

Phe Ala Gln Phe Val Thr Ala Tyr Glu Asp Ile Val Arg Arg Ala Arg
    210                 215                 220

Asp Gly Lys Leu Thr Thr Glu Asp Phe Ala Gly Val Thr Ile Ser Leu
225                 230                 235                 240

Thr Asn Pro Gly Thr Ile Gly Thr Val His Ser Val Pro Arg Leu Met
                245                 250                 255

Pro Gly Gln Gly Ala Ile Ile Gly Val Gly Ala Met Glu Tyr Pro Ala
            260                 265                 270

Glu Phe Gln Gly Ala Ser Glu Glu Arg Ile Ala Glu Leu Gly Ile Gly
        275                 280                 285

Lys Leu Ile Thr Leu Thr Ser Thr Tyr Asp His Arg Ile Ile Gln Gly
    290                 295                 300

Ala Glu Ser Gly Asp Phe Leu Arg Thr Ile His Glu Leu Leu Leu Ser
305                 310                 315                 320

Asp Gly Phe Trp Asp Glu Val Phe Arg Glu Leu Ser Ile Pro Tyr Leu
                325                 330                 335

Pro Val Arg Trp Ser Thr Asp Asn Pro Asp Ser Ile Val Asp Lys Asn
            340                 345                 350

Ala Arg Val Met Asn Leu Ile Ala Ala Tyr Arg Asn Arg Gly His Leu
        355                 360                 365

Met Ala Asp Thr Asp Pro Leu Arg Leu Asp Lys Ala Arg Phe Arg Ser
    370                 375                 380

His Pro Asp Leu Glu Val Leu Thr His Gly Leu Thr Leu Trp Asp Leu
385                 390                 395                 400

Asp Arg Val Phe Lys Val Asp Gly Phe Ala Gly Ala Gln Tyr Lys Lys
                405                 410                 415

Leu Arg Asp Val Leu Gly Leu Leu Arg Asp Ala Tyr Cys Arg His Ile
            420                 425                 430

Gly Val Glu Tyr Ala His Ile Leu Asp Pro Glu Gln Lys Glu Trp Leu
        435                 440                 445

Glu Gln Arg Val Glu Thr Lys His Val Lys Pro Thr Val Ala Gln Gln
    450                 455                 460

Lys Tyr Ile Leu Ser Lys Leu Asn Ala Ala Glu Ala Phe Glu Thr Phe
465                 470                 475                 480
```

```
Leu Gln Thr Lys Tyr Val Gly Gln Lys Arg Phe Ser Leu Glu Gly Ala
                485                 490                 495

Glu Ser Val Ile Pro Met Met Asp Ala Ala Ile Asp Gln Cys Ala Glu
            500                 505                 510

His Gly Leu Asp Glu Val Val Ile Gly Met Pro His Arg Gly Arg Leu
        515                 520                 525

Asn Val Leu Ala Asn Ile Val Gly Lys Pro Tyr Ser Gln Ile Phe Thr
    530                 535                 540

Glu Phe Glu Gly Asn Leu Asn Pro Ser Gln Ala His Gly Ser Gly Asp
545                 550                 555                 560

Val Lys Tyr His Leu Gly Ala Thr Gly Leu Tyr Leu Gln Met Phe Gly
                565                 570                 575

Asp Asn Asp Ile Gln Val Ser Leu Thr Ala Asn Pro Ser His Leu Glu
            580                 585                 590

Ala Val Asp Pro Val Leu Glu Gly Leu Val Arg Ala Lys Gln Asp Leu
        595                 600                 605

Leu Asp His Gly Ser Ile Asp Ser Asp Gly Gln Arg Ala Phe Ser Val
    610                 615                 620

Val Pro Leu Met Leu His Gly Asp Ala Ala Phe Ala Gly Gln Gly Val
625                 630                 635                 640

Val Ala Glu Thr Leu Asn Leu Ala Asn Leu Pro Gly Tyr Arg Val Gly
                645                 650                 655

Gly Thr Ile His Ile Ile Val Asn Asn Gln Ile Gly Phe Thr Thr Ala
            660                 665                 670

Pro Glu Tyr Ser Arg Ser Ser Glu Tyr Cys Thr Asp Val Ala Lys Met
        675                 680                 685

Ile Gly Ala Pro Ile Phe His Val Asn Gly Asp Asp Pro Glu Ala Cys
    690                 695                 700

Val Trp Val Ala Arg Leu Ala Val Asp Phe Arg Gln Arg Phe Lys Lys
705                 710                 715                 720

Asp Val Val Ile Asp Met Leu Cys Tyr Arg Arg Arg Gly His Asn Glu
                725                 730                 735

Gly Asp Asp Pro Ser Met Thr Asn Pro Tyr Met Tyr Asp Val Val Asp
            740                 745                 750

Thr Lys Arg Gly Ala Arg Lys Ser Tyr Thr Glu Ala Leu Ile Gly Arg
        755                 760                 765

Gly Asp Ile Ser Met Lys Glu Ala Glu Asp Ala Leu Arg Asp Tyr Gln
    770                 775                 780

Gly Gln Leu Glu Arg Val Phe Asn Glu Val Arg Glu Leu Glu Lys His
785                 790                 795                 800

Gly Val Gln Pro Ser Glu Ser Val Glu Ser Asp Gln Met Ile Pro Ala
                805                 810                 815

Gly Leu Ala Thr Ala Val Asp Lys Ser Leu Leu Ala Arg Ile Gly Asp
            820                 825                 830

Ala Phe Leu Ala Leu Pro Asn Gly Phe Thr Ala His Pro Arg Val Gln
        835                 840                 845

Pro Val Leu Glu Lys Arg Arg Glu Met Ala Tyr Glu Gly Lys Ile Asp
    850                 855                 860

Trp Ala Phe Gly Glu Leu Leu Ala Leu Gly Ser Leu Val Ala Glu Gly
865                 870                 875                 880

Lys Leu Val Arg Leu Ser Gly Gln Asp Ser Arg Arg Gly Thr Phe Ser
                885                 890                 895

Gln Arg His Ser Val Leu Ile Asp Arg His Thr Gly Glu Glu Phe Thr
```

```
            900                 905                 910

Pro Leu Gln Leu Leu Ala Thr Asn Ser Asp Gly Ser Pro Thr Gly Gly
        915                 920                 925

Lys Phe Leu Val Tyr Asp Ser Pro Leu Ser Glu Tyr Ala Ala Val Gly
    930                 935                 940

Phe Glu Tyr Gly Tyr Thr Val Gly Asn Pro Asp Ala Val Val Leu Trp
945                 950                 955                 960

Glu Ala Gln Phe Gly Asp Phe Val Asn Gly Ala Gln Ser Ile Ile Asp
                965                 970                 975

Glu Phe Ile Ser Ser Gly Glu Ala Lys Trp Gly Gln Leu Ser Asn Val
            980                 985                 990

Val Leu Leu Leu Pro His Gly His Glu Gly Gln Gly Pro Asp His Thr
        995                 1000                1005

Ser Ala Arg Ile Glu Arg Phe Leu Gln Leu Trp Ala Glu Gly Ser Met
    1010                1015                1020

Thr Ile Ala Met Pro Ser Thr Pro Ser Asn Tyr Phe His Leu Leu Arg
1025                1030                1035                1040

Arg His Ala Leu Asp Gly Ile Gln Arg Pro Leu Ile Val Phe Thr Pro
                1045                1050                1055

Lys Ser Met Leu Arg His Lys Ala Ala Val Ser Glu Ile Lys Asp Phe
            1060                1065                1070

Thr Glu Ile Lys Phe Arg Ser Val Leu Glu Glu Pro Thr Tyr Glu Asp
        1075                1080                1085

Gly Ile Gly Asp Arg Asn Lys Val Ser Arg Ile Leu Leu Thr Ser Gly
    1090                1095                1100

Lys Leu Tyr Tyr Glu Leu Ala Ala Arg Lys Ala Lys Asp Asn Arg Asn
1105                1110                1115                1120

Asp Leu Ala Ile Val Arg Leu Glu Gln Leu Ala Pro Leu Pro Arg Arg
                1125                1130                1135

Arg Leu Arg Glu Thr Leu Asp Arg Tyr Glu Asn Val Lys Glu Phe Phe
            1140                1145                1150

Trp Val Gln Glu Glu Pro Ala Asn Gln Gly Ala Trp Pro Arg Phe Gly
        1155                1160                1165

Leu Glu Leu Pro Glu Leu Leu Pro Asp Lys Leu Ala Gly Ile Lys Arg
    1170                1175                1180

Ile Ser Arg Arg Ala Met Ser Ala Pro Ser Ser Gly Ser Ser Lys Val
1185                1190                1195                1200

His Ala Val Glu Gln Gln Glu Ile Leu Asp Glu Ala Phe Gly
                1205                1210


<210> SEQ ID NO 82
<211> LENGTH: 3645
<212> TYPE: DNA
<213> ORGANISM: Mycobacterium bovis

<400> SEQUENCE: 82

atgtaccgta aattccgtga tgacccgtct tctgttgatc cgtcttggca cgaatttctg      60

gtcgattact ccccggaacc aacttcccag ccggccgctg aaccgacccg cgttacgtcc     120

cctctggtcg cggaacgtgc agctgcggca gcaccgcagg cgccaccaaa acctgctgat     180

accgctgcag ctggtaatgg tgtggttgct gcactggctg ctaaaacggc tgttccgccg     240

cctgctgaag gtgatgaagt ggccgtgctg cgtggtgcgg cagccgcggt cgtcaaaaac     300

atgagcgcgt ctctggaagt gccgacggcg accagcgtgc gcgcggttcc agcgaaactg     360
```

-continued

```
ctgattgata atcgtattgt gatcaacaac cagctgaaac gtacccgtgg tggcaaaatt    420
agctttaccc acctgctggg ttatgccctg gtgcaggcgg tgaagaaatt cccgaacatg    480
aaccgtcact acaccgaagt cgacggtaaa ccgactgccg tgaccccggc acacaccaac    540
ctgggcctgg caattgacct gcagggcaag gatggcaagc gttccctggt agtagctggt    600
attaaacgtt gcgaaaccat gcgctttgca cagttcgtaa ccgcgtacga agatatcgta    660
cgtcgcgcac gtgatggcaa actgactacc gaagacttcg cgggtgtgac catttccctg    720
accaacccgg gcaccatcgg tactgtacat agcgtaccac gtctgatgcc gggtcagggt    780
gcgattatcg gcgttggtgc tatggagtat ccggccgagt ttcagggtgc ttccgaagag    840
cgtatcgcgg aactgggtat tggtaaactg attaccctga cgagcaccta cgaccaccgc    900
atcatccagg gcgccgaaag cggtgacttc ctgcgtacca tccatgaact gctgctgtcc    960
gatggtttct gggatgaagt cttccgcgaa ctgtctattc cgtacctgcc ggtccgttgg   1020
tccaccgata acccggattc tattgtagac aaaaacgccc gcgttatgaa cctgatcgca   1080
gcgtatcgta atcgtggcca cctgatggca gacacggacc ctctgcgtct ggacaaagcg   1140
cgttttcgca gccacccgga cctggaagtt ctgactcatg gcctgactct gtgggatctg   1200
gatcgcgtat ttaaagtgga tggctttgca ggtgcccagt acaagaaact gcgtgatgtt   1260
ctgggcctgc tgcgtgacgc ctattgccgc catattggtg ttgaatacgc gcacatcctg   1320
gacccagagc agaaagaatg gctggagcag cgtgtggaaa ccaaacacgt taagccgacc   1380
gtagcgcagc agaaatacat cctgtctaag ctgaacgctg ccgaggcttt cgaaaccttt   1440
ctgcagacga aatatgttgg tcagaaacgc ttctccctgg agggtgcaga atctgtgatc   1500
ccgatgatgg atgctgcgat cgaccagtgc gctgaacacg gcctggacga ggtagtgatc   1560
ggtatgccgc accgtggccg tctgaacgtt ctggctaaca tcgttggtaa accgtacagc   1620
cagatcttta ctgaattcga aggcaacctg aacccgtccc aggctcatgg ttccggcgac   1680
gtgaaatacc atctgggcgc aactggtctg tacctgcaga tgttcggtga taatgacatc   1740
caggtatctc tgaccgctaa tccgtcccac ctggaagcgg ttgacccggt actggaaggc   1800
ctggttcgtg caaaacaaga tctgctggac cacggtagca tcgattctga cggtcagcgt   1860
gccttctctg tggttccgct gatgctgcac ggcgatgcgg cttttgcagg ccagggtgtt   1920
gttgctgaaa cgctgaacct ggcgaacctg ccgggctacc gtgttggtgg cactatccat   1980
atcatcgtta acaaccagat cggcttcacg accgcgccgg aatactctcg ctctagcgaa   2040
tactgcactg atgtggctaa gatgattggc gccccaatct tccacgttaa cggtgacgac   2100
ccggaagcgt gtgtgtgggt tgcccgtctg gctgtggatt tccgtcaacg tttcaaaaag   2160
gacgttgtta tcgacatgct gtgttaccgt cgtcgcggcc acaacgaagg cgacgatccg   2220
agcatgacta acccttacat gtacgatgta gttgacacca aacgtggcgc acgtaaaagc   2280
tatactgaag cgctgatcgg tcgtggtgat atctctatga aagaagcaga agacgcactg   2340
cgcgactatc aaggccaact ggaacgcgtt ttcaacgaag ttcgcgagct ggagaaacac   2400
ggtgtccaac ctagcgaatc tgtggaatct gaccagatga tcccggcggg tctggcaact   2460
gcagtggaca aaagcctgct ggcacgtatt ggcgacgcgt tcctggctct gccgaacggt   2520
ttcactgcac acccacgtgt acagccggtt ctggaaaaac gtcgtgaaat ggcctacgaa   2580
ggtaaaatcg actgggcttt tggtgagctg ctggcgctgg gctccctggt tgcggagggt   2640
aaactggtcc gtctgagcgg tcaagattct cgtcgtggta ctttcagcca gcgtcactct   2700
gtgctgatcg atcgtcacac gggtgaagaa ttcaccccgc tgcaactgct ggcgaccaac   2760
```

```
tccgatggct ctcctaccgg tggtaaattc ctggtatacg actctccact gtctgaatat   2820

gctgcagttg gcttcgaata cggttacact gttggtaacc cggacgctgt tgtgctgtgg   2880

gaagctcagt tcggcgactt cgtaaatggc gcgcagtcca tcattgacga attcatttcc   2940

tctggcgaag cgaaatgggg ccagctgtcc aacgtcgtgc tgctgctgcc acacggccat   3000

gaaggtcagg gtccggatca tacttctgcg cgcatcgagc gtttcctgca gctgtgggcc   3060

gagggctcca tgaccatcgc catgccgtcc accccgtcta attattttca cctgctgcgc   3120

cgtcacgcgc tggacggtat ccagcgcccg ctgattgttt tcaccccgaa atccatgctg   3180

cgccacaaag cggcagtcag cgagattaaa gatttcaccg aaatcaaatt ccgctccgtc   3240

ctggaagaac cgacctatga agacggcatc ggtgaccgca acaaggtaag ccgcattctg   3300

ctgacctccg gcaaactgta ttacgagctg gcagctcgca aggcgaagga taaccgcaac   3360

gatctggcaa tcgtgcgcct ggaacagctg gcgccgctgc cgcgtcgccg tctgcgtgaa   3420

accctggatc gctatgaaaa cgtaaaagag ttcttctggg ttcaagaaga gccggcaaac   3480

cagggcgctt ggccgcgttt tggcctggag ctgccggagc tgctgccgga caagctggcc   3540

ggtatcaaac gtatctcccg tcgtgctatg agcgcccctt ctagcggttc ttctaaagtt   3600

catgctgttg aacagcaaga aatcctggac gaagcgttcg gctaa                   3645
```

```
<210> SEQ ID NO 83
<211> LENGTH: 633
<212> TYPE: PRT
<213> ORGANISM: Euglena gracilis

<400> SEQUENCE: 83

Met Tyr Arg Leu Lys Asn Leu Gln Ala Val Pro Trp Lys Ala Pro Thr
  1               5                  10                  15

Arg Ala Ile Arg Gly Ile Ala Leu Asp Gly Pro Asp Arg Asp Arg Met
             20                  25                  30

Phe Asn Ala Tyr Leu His Ser Ser Arg Pro Ser Phe Gly Pro Ala Thr
         35                  40                  45

Asp Val Phe Val Gln Cys Leu Glu Ala Glu Lys Ile Asp Trp Ile Phe
     50                  55                  60

Gly Ile Pro Gly Glu Glu Asn Leu Asp Leu Leu His Ser Leu Ala Lys
 65                  70                  75                  80

Ala His Arg Arg Glu Gly Gly Glu Thr Met Lys Leu Val Val Thr Arg
                 85                  90                  95

His Glu Gln Ala Ala Gly Phe Met Ala Ala Thr Val Gly Arg Leu Thr
            100                 105                 110

Gly His Pro Ala Ala Cys Leu Ser Thr Leu Gly Pro Gly Ala Thr Asn
        115                 120                 125

Phe Thr Thr Ala Leu Ala Tyr Ser Lys Leu Gly Gly Phe Pro Leu Ile
    130                 135                 140

Cys Ile Thr Gly Gln Lys Pro Ile Arg His Ser Lys Gln Gly Ala Phe
145                 150                 155                 160

Gln Ile Leu Asp Ile Cys Gly His Phe Arg Asp Val Val Lys Ser Thr
                165                 170                 175

Lys Ser Ile Glu Asp Pro Asp Leu Ile Pro Ser Thr Ile Arg Asn Ala
            180                 185                 190

Val Leu Gln Ala Arg Glu Glu Lys Pro Gly Pro Val His Ile Glu Leu
        195                 200                 205

Ala Glu Asp Ile Ala Ala Leu Glu Val Ser Lys Glu Gly Gly Trp Val
```

```
    210                 215                 220

Phe Pro Ala Pro Thr Arg Thr Pro Ile Ala Arg Gly Arg Arg Pro Leu
225                 230                 235                 240

Val Glu Pro Lys Cys Ile Glu His Ala Val Thr Leu Ile His Ala Ala
                245                 250                 255

Lys Arg Pro Leu Ile Cys Ile Ala Ala Gly Ala Asn Arg Lys Asn Thr
            260                 265                 270

His His Ala Met Glu Val Leu Met Arg Lys Thr Gly Leu Met Val Val
        275                 280                 285

Cys Thr Gln Met Gly Lys Gly Val Val Tyr Glu Asp Asn Leu Gly Tyr
    290                 295                 300

Ile Gly Cys Thr Ala Leu Ser Asp Lys Asp Leu Val His Val Ala Ile
305                 310                 315                 320

Asn Thr Ala Asp Leu Ile Val Asn Val Gly His Asp Ile Ser Glu Lys
                325                 330                 335

Pro Pro Phe Ile Met Asn His Asn Lys Pro Pro Leu Val Ile His Ala
            340                 345                 350

Asn Phe Thr Arg Pro Leu Val Asp Pro Val Tyr Phe Pro His Leu Val
        355                 360                 365

Leu Val Gly Asp Ile Asn Asp Cys Leu Trp Gln Leu Ala Thr Arg Ile
    370                 375                 380

Arg Pro Gln Pro His Trp Asp Phe Asn Pro Phe Gln Met Val Arg Arg
385                 390                 395                 400

Glu Ile Glu Arg Thr Val Trp Asn Ser Pro Tyr Ala Gln Ser Asp Ala
                405                 410                 415

Phe Pro Leu Thr Val Gln Arg Leu Val Ser Asp Val Arg Lys Ala Met
            420                 425                 430

Pro Val Asp Gly Ile Val Ser Leu Asp Asn Gly Met Tyr Lys Ile Trp
        435                 440                 445

Phe Ala Arg Gln Tyr Lys Thr Met Met Gly Asn Thr Leu Leu Leu Asp
    450                 455                 460

Asn Ala Leu Ala Thr Met Gly Ala Gly Leu Pro Ser Cys Ile Ala Ala
465                 470                 475                 480

Lys Leu Val Tyr Pro Glu Arg Val Cys Ile Ala Val Cys Gly Asp Gly
                485                 490                 495

Gly Phe Met Met Asn Ser Gln Glu Ile Glu Thr Ala Leu Arg Leu Asn
            500                 505                 510

Leu His Ile Val Val Ile Val Leu Asn Asn Asn Ser Tyr Gly Met Ile
        515                 520                 525

Ala Trp Lys Ala Thr Ala Met Gly Met Asp Asp Phe Gly Leu Asn Tyr
    530                 535                 540

Gly Asn Pro Asp Phe Ala Gln Tyr Ala Arg Ala Tyr Gly Ala Ile Gly
545                 550                 555                 560

His Asn Val Lys Ser Thr Ala Glu Phe Leu Pro Thr Leu Glu Lys Ala
                565                 570                 575

Ile Lys Glu His Gly Val His Ile Ile Asp Leu Pro Ile Ser Tyr Glu
            580                 585                 590

Thr Ser Asp Lys Ala Leu Phe Glu Asp Leu Pro Lys Glu Val Glu Glu
        595                 600                 605

Leu Lys Lys Ala Val Ala Lys Ala Ile Ser Glu Glu Lys Lys Phe Asp
    610                 615                 620

Trp Asp Ala Val Thr Ala Ala Gln Ser
625                 630
```

<210> SEQ ID NO 84
<211> LENGTH: 1902
<212> TYPE: DNA
<213> ORGANISM: Euglena gracilis

<400> SEQUENCE: 84

```
atgtatcgtc tgaaaaatct gcaagctgta ccatggaaag ccccaacccg cgcgattcgc     60
ggcatcgcgc tggatggtcc ggatcgtgat cgtatgttca acgcgtacct gcattcttct    120
cgcccttcct tcggcccggc cactgacgtt ttcgttcagt gcctggaagc tgaaaaaatc    180
gactggatct tcggcattcc gggcgaagaa aacctggatc tgctgcacag cctggcaaag    240
gcgcaccgtc gtgaaggtgg tgaaactatg aaactggtcg taacccgtca tgaacaggcg    300
gcaggtttca tggcagcaac cgttggtcgt ctgactggtc atccggcagc gtgcctgtct    360
accctgggtc caggtgctac caattttacc accgcgctgg cttacagcaa actgggcggc    420
ttcccgctga tctgtatcac tggccagaaa ccgatccgtc actctaagca gggtgcgttt    480
cagattctgg acatttgtgg ccacttccgc gacgtggtca aatccaccaa gtccattgaa    540
gacccggacc tgattccgtc taccattcgt aacgcggtgc tgcaggcacg tgaagagaag    600
ccgggtccgg tacacatcga actggctgaa gatattgcgg ctctggaagt gtctaaagaa    660
ggtggctggg tgtttccggc tccaacccgt accccgatcg cacgtggtcg tcgccctctg    720
gtggaaccaa aatgcatcga acatgcggtt actctgatcc acgcagcgaa acgtccgctg    780
atttgtatcg cagcgggtgc taaccgtaaa aacacgcatc acgctatgga agtactgatg    840
cgtaaaaccg gcctgatggt tgtttgtacc cagatgggca aaggtgttgt gtacgaagac    900
aacctgggct acatcggctg taccgccctg tccgacaaag acctggttca cgttgcaatc    960
aacaccgcgg atctgatcgt gaacgtaggt cacgacatca gcgaaaaacc gccgttcatt   1020
atgaaccaca acaaacctcc gctggtaatt cacgcgaact tcactcgccc gctggttgat   1080
ccggtgtatt tcccgcatct ggtcctggtt ggtgacatta acgattgcct gtggcagctg   1140
gctacccgca tccgtccgca gccgcattgg gatttcaatc cgttccaaat ggttcgtcgt   1200
gagatcgaac gcaccgtttg gaactcccca tatgcccaat ctgacgcgtt tcctctgact   1260
gttcagcgcc tggtttctga cgttcgcaaa gccatgccgg ttgacggcat cgtgagcctg   1320
gataacggca tgtacaaaat ctggtttgct cgtcagtaca aaaccatgat gggtaacacg   1380
ctgctgctgg ataatgcgct ggcaacgatg ggtgctggtc tgccgtcttg catcgcagcc   1440
aaactggttt atccggaacg tgtctgcatc gccgtatgcg gcgatggtgg cttcatgatg   1500
aactcccagg agatcgagac tgcactgcgc ctgaacctgc acatcgtagt tatcgtactg   1560
aacaacaact cctacggcat gatcgcttgg aaggccactg cgatgggcat ggacgatttt   1620
ggcctgaact acggtaaccc ggacttcgct cagtatgcac gtgcttacgg tgctatcggt   1680
cacaatgtga aatctaccgc ggaattcctg ccgacgctgg agaaagctat caaagaacac   1740
ggtgtccaca tcattgatct gccgattagc tacgaaacta gcgataaagc actgttcgaa   1800
gacctgccga aagaggtcga ggaactgaaa aaggcagtgg cgaaagcgat ctccgaggaa   1860
aaaaagtttg attgggacgc cgtgacggcc gctcagagct aa                      1902
```

<210> SEQ ID NO 85
<211> LENGTH: 59
<212> TYPE: DNA
<213> ORGANISM: Artificial Sequence
<220> FEATURE:

<223> OTHER INFORMATION: Synthetic M. bovis sucA F

<400> SEQUENCE: 85
agacgactgt actaatctag tcacacagga aacagaattc atgtaccgta aattccgtg 59

<210> SEQ ID NO 86
<211> LENGTH: 46
<212> TYPE: DNA
<213> ORGANISM: Artificial Sequence
<220> FEATURE:
<223> OTHER INFORMATION: Synthetic M. bovis sucA R

<400> SEQUENCE: 86
ttgcatgcct gcaggtcgac tctagttagc tctgagcggc cgtcac 46

<210> SEQ ID NO 87
<211> LENGTH: 59
<212> TYPE: DNA
<213> ORGANISM: Artificial Sequence
<220> FEATURE:
<223> OTHER INFORMATION: Synthetic E. grac sucA F

<400> SEQUENCE: 87
agacgactgt actaatctag tcacacagga aacagaattc atgtatcgtc tgaaaaatc 59

<210> SEQ ID NO 88
<211> LENGTH: 46
<212> TYPE: DNA
<213> ORGANISM: Artificial Sequence
<220> FEATURE:
<223> OTHER INFORMATION: Synthetic E. grac sucA R

<400> SEQUENCE: 88
ttgcatgcct gcaggtcgac tctagttagc tctgagcggc cgtcac 46

<210> SEQ ID NO 89
<211> LENGTH: 60
<212> TYPE: DNA
<213> ORGANISM: Artificial Sequence
<220> FEATURE:
<223> OTHER INFORMATION: Synthetic E. coli sucA F

<400> SEQUENCE: 89
agacgactgt actaatctag tcacacagga aacagaattc atgcagaaca gcgctttgaa 60

<210> SEQ ID NO 90
<211> LENGTH: 45
<212> TYPE: DNA
<213> ORGANISM: Artificial Sequence
<220> FEATURE:
<223> OTHER INFORMATION: Synthetic E. coli sucA R

<400> SEQUENCE: 90
ttgcatgcct gcaggtcgac tctagttatt cgacgttcag cgcgt 45

<210> SEQ ID NO 91
<211> LENGTH: 61
<212> TYPE: DNA
<213> ORGANISM: Artificial Sequence
<220> FEATURE:
<223> OTHER INFORMATION: Synthetic Cgl kgd F

<400> SEQUENCE: 91
agacgactgt actaatctag tcacacagga aacagaattc atgagcagcg ctagtacttt 60
c 61

<210> SEQ ID NO 92
<211> LENGTH: 46
<212> TYPE: DNA
<213> ORGANISM: Artificial Sequence
<220> FEATURE:
<223> OTHER INFORMATION: Synthetic Cgl kgd R

<400> SEQUENCE: 92
ttgcatgcct gcaggtcgac tctagttaag cctcgaaagc ctcgtc 46

<210> SEQ ID NO 93
<211> LENGTH: 468
<212> TYPE: PRT
<213> ORGANISM: Artificial Sequence
<220> FEATURE:
<223> OTHER INFORMATION: Synthetic BldI

<400> SEQUENCE: 93

```
Met Ile Lys Asp Thr Leu Val Ser Ile Thr Lys Asp Leu Lys Leu Lys
1               5                   10                  15

Thr Asn Val Glu Asn Ala Asn Leu Lys Asn Tyr Lys Asp Asp Ser Ser
            20                  25                  30

Cys Phe Gly Val Phe Glu Asn Val Glu Asn Ala Ile Ser Asn Ala Val
        35                  40                  45

His Ala Gln Lys Ile Leu Ser Leu His Tyr Thr Lys Glu Gln Arg Glu
    50                  55                  60

Lys Ile Ile Thr Glu Ile Arg Lys Ala Ala Leu Glu Asn Lys Glu Ile
65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
        115                 120                 125

Glu Met Ser Pro Tyr Gly Val Ile Gly Ala Ile Thr Pro Ser Thr Asn
    130                 135                 140

Pro Thr Glu Thr Val Ile Cys Asn Ser Ile Gly Met Ile Ala Ala Gly
145                 150                 155                 160

Asn Thr Val Val Phe Asn Gly His Pro Gly Ala Lys Lys Cys Val Ala
                165                 170                 175

Phe Ala Val Glu Met Ile Asn Lys Ala Ile Ile Ser Cys Gly Gly Pro
            180                 185                 190

Glu Asn Leu Val Thr Thr Ile Lys Asn Pro Thr Met Asp Ser Leu Asp
        195                 200                 205

Ala Ile Ile Lys His Pro Ser Ile Lys Leu Leu Cys Gly Thr Gly Gly
    210                 215                 220

Pro Gly Leu Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Lys Ser Ile Ile Glu Gly Cys Ser Phe Asp Asn Asn
            260                 265                 270

Leu Pro Cys Ile Ala Glu Lys Glu Val Phe Val Phe Glu Asn Val Ala
        275                 280                 285

Asp Asp Leu Ile Ser Asn Met Leu Lys Asn Asn Ala Val Ile Ile Asn
    290                 295                 300
```

```
Glu Asp Gln Val Ser Lys Leu Ile Asp Leu Val Leu Gln Lys Asn Asn
305                 310                 315                 320

Glu Thr Gln Glu Tyr Ser Ile Asn Lys Lys Trp Val Gly Lys Asp Ala
                325                 330                 335

Lys Leu Phe Leu Asp Glu Ile Asp Val Glu Ser Pro Ser Ser Val Lys
            340                 345                 350

Cys Ile Ile Cys Glu Val Ser Ala Arg His Pro Phe Val Met Thr Glu
        355                 360                 365

Leu Met Met Pro Ile Leu Pro Ile Val Arg Val Lys Asp Ile Asp Glu
    370                 375                 380

Ala Ile Glu Tyr Ala Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415

Ile Asp Thr Thr Ile Phe Val Lys Asn Ala Lys Ser Phe Ala Gly Val
            420                 425                 430

Gly Tyr Glu Ala Glu Gly Phe Thr Thr Phe Thr Ile Ala Gly Ser Thr
        435                 440                 445

Gly Glu Gly Ile Thr Ser Ala Arg Asn Phe Thr Arg Gln Arg Arg Cys
    450                 455                 460

Val Leu Ala Gly
465


<210> SEQ ID NO 94
<211> LENGTH: 1407
<212> TYPE: DNA
<213> ORGANISM: Artificial Sequence
<220> FEATURE:
<223> OTHER INFORMATION: Synthetic bldI

<400> SEQUENCE: 94

atgattaaag acacgctagt ttctataaca aaagatttaa aattaaaaac aaatgttgaa     60

aatgccaatc taaagaacta caaggatgat tcttcatgtt tcggagtttt cgaaaatgtt    120

gaaaatgcta taagcaatgc cgtacacgca caaaagatat tatcccttca ttatacaaaa    180

gaacaaagag aaaaaatcat aactgagata agaaaggccg cattagaaaa taaagagatt    240

ctagctacaa tgattcttga agaaacacat atgggaagat atgaagataa aatattaaag    300

catgaattag tagctaaata cactcctggg acagaagatt taactactac tgcttggtca    360

ggagataacg ggcttacagt tgtagaaatg tctccatatg gcgttatagg tgcaataact    420

ccttctacga atccaactga aactgtaata tgtaatagta taggcatgat agctgctgga    480

aatactgtgg tatttaacgg acatccaggc gctaaaaaat gtgttgcttt tgctgtcgaa    540

atgataaata aagctattat ttcatgtggt ggtcctgaga atttagtaac aactataaaa    600

aatccaacta tggactctct agatgcaatt attaagcacc cttcaataaa actactttgc    660

ggaactggag ggccaggact cgtaaaaacc ctcttaaatt ctggtaagaa agctataggt    720

gctggtgctg gaaatccacc agttattgta gatgatactg ctgatataga aaaggctggt    780

aagagtatca ttgaaggctg ttcttttgat aataatttac cttgtattgc agaaaaagaa    840

gtatttgttt ttgagaacgt tgcagatgat ttaatatcta acatgctaaa aaataatgct    900

gtaattataa atgaagatca agtatcaaag ttaatagatt tagtattaca aaaaaataat    960

gaaactcaag aatactctat aaataagaaa tgggtcggaa aagatgcaaa attattctta   1020

gatgaaatag atgttgagtc tccttcaagt gttaaatgca taatctgcga agtaagtgca   1080
```

-continued

```
aggcatccat ttgttatgac agaactcatg atgccaatat taccaattgt aagagttaaa   1140

gatatagatg aagctattga atatgcaaaa atagcagaac aaaatagaaa acatagtgcc   1200

tatatttatt caaaaaatat agacaaccta aataggtttg aaagagaaat cgatactact   1260

atctttgtaa agaatgctaa atcttttgcc ggtgttggtt atgaagcaga aggctttaca   1320

actttcacta ttgctggatc cactggtgaa ggaataactt ctgcaagaaa ttttacaaga   1380

caaagaagat gtgtactcgc cggttaa                                       1407
```

MICROORGANISM HAVING ENHANCED ACTIVITY OF ALPHA-KETOGLUTARATE DECARBOXYLASE AND A METHOD OF PRODUCING 1,4-BUTANEDIOL USING THE SAME

CROSS-REFERENCE TO RELATED APPLICATIONS

This patent application is the U.S. national phase of International Application No. PCT/KR2014/008293, filed on Sep. 4, 2014, which claims priority to International Application No. PCT/KR2014/003843, filed on Apr. 30, 2014, the entire disclosures of which are incorporated by reference.

TECHNICAL FIELD

The present disclosure relates to a microorganism having an enhanced activity of alpha-ketoglutarate decarboxylase and a method of producing 1,4-butanediol using the same.

BACKGROUND ART 1,4-butanediol (1,4-BDO) may be used as a solvent in the manufacture of plastics, fibers, polyurethanes, etc. 1,4-BDO may be also converted to polytetramethylene ether glycol (PTMEG) as a raw material for spandex fibers via tetrahydrofuran (THF).

1,4-BDO is currently produced by the Reppe process using acetylene and formalin as raw materials or by the Davy Mckee process using butane as a raw material. However, production of 1,4-BDO by chemical methods requires use of gas and oil-associated raw materials, and accordingly, there is a demand for alternative production methods to reduce production costs and improve environmental protection.

In this regard, a method of efficiently producing 1,4-BDO by using a microorganism is required.

DETAILED DESCRIPTION OF THE INVENTION

Technical Problem

An aspect provides a microorganism having an enhanced 4HB or 1,4-BDO productivity.

Another aspect provides a method of efficiently producing 4HB or 1,4-BDO using the microorganism.

Technical Solution

An aspect provides a microorganism having an enhanced activity of converting alpha-ketoglutarate to succinic semialdehyde. As used herein, the term "activity of converting alpha-ketoglutarate to succinic semialdehyde" may refer to an activity of a reaction which is the same as a reaction catalyzed by alpha-ketoglutarate decarboxylase (EC 4.1.1.71).

The microorganism may be a microorganism lacking a metabolic pathway which converts alpha-ketoglutarate to succinic semialdehyde in a non-genetically engineered state. For example, the microorganism may be a prokaryotic or eukaryotic cell or organism, a eukaryotic microorganism such as yeast and fungus, or all species of bacteria, archaebacteria and eubacteria. The microorganism may be a microorganism derived from the genus *Escherichia* or the genus *Corynebacterium*. The genus *Escherichia* microorganism may be *Escherichia coli* (*E. coli*), *Escherichia albertii* (*E. albertii*), *Escherichia blattae* (*E. blattae*), *Escherichia fergusonii* (*E. fergusonii*), *Escherichia hermannii* (*E. hermannii*), or *Escherichia vulneris* (*E. vulneris*). The microorganism may be *Escherichia coli* or *Corynebacterium glutamicum*.

The activity of converting alpha-ketoglutarate to succinic semialdehyde may be increased by increased expression of alpha-ketoglutarate decarboxylase (α-ketoglutarate decarboxylase) and/or increased expression of alpha-ketoglutarate dehydrogenase E1 component. The alpha-ketoglutarate decarboxylase may be an enzyme classified as EC. 4.1.1.71. The alpha-ketoglutarate dehydrogenase E1 component may exist as a subunit that constitutes an alpha-ketoglutarate dehydrogenase complex (α-ketoglutarate dehydrogenase complex: α-KGDH complex) together with transsuccinylase component (E2) and dihydrolipoyl dehydrogenase component (E3) in a non-genetically engineered microorganism. The α-KGDH complex may be an enzyme classified as EC.1.2.4.2. The α-KGDH complex may have an activity of catalyzing a reaction converting alpha-ketoglutarate to succinyl CoA. The α-KGDH complex may be also called oxoglutarate dehydrogenase complex.

The alpha-ketoglutarate dehydrogenase E1 component may be derived from the genus *Escherichia* or the genus *Corynebacterium*. The alpha-ketoglutarate dehydrogenase E1 component derived from the genus *Escherichia* may be derived from *Escherichia coli*. The alpha-ketoglutarate dehydrogenase E1 component derived from *Escherichia coli* may have an amino acid sequence of SEQ ID NO: 1. The alpha-ketoglutarate dehydrogenase E1 component derived from the genus *Corynebacterium* may be derived from *Corynebacterium glutamicum*. The alpha-ketoglutarate dehydrogenase E1 component derived from *Corynebacterium glutamicum* may have an amino acid sequence of SEQ ID NO: 3.

The increased expression of the alpha-ketoglutarate dehydrogenase E1 component may be caused by increased expression of an endogenous polynucleotide encoding the E1 component. The increased expression of the endogenous polynucleotide may be caused by mutation of an expression regulatory region. Further, the increased expression of E1 component may be caused by introduction of an exogenous polynucleotide encoding the E1 component. The polynucleotide may be derived from the genus *Escherichia* or the genus *Corynebacterium*. The polynucleotide may be derived from *Escherichia coli* or *Corynebacterium glutamicum*. The polynucleotide derived from *Escherichia coli* may be sucA. The sucA may have a nucleotide sequence of SEQ ID NO: 2. The polynucleotide derived from *Corynebacterium glutamicum* may be kgd (NCgl1084). The kgd may have a nucleotide sequence of SEQ ID NO: 4.

Introduction of the polynucleotide may be introduction of an expression cassette or introduction of the polynucleotide in itself. The expression cassette may include all elements required for expression of the polynucleotide. The expression cassette may include a promoter, a transcription termination signal, a ribosome binding site, and a translation termination signal, which are operably linked to the polynucleotide. The expression cassette may be in the form of a self-replicable expression vector. The introduction may be transformation. The introduced polynucleotide may be integrated into the host chromosome or/and exit as an extrachromosomal element. The polynucleotide includes DNA or RNA.

Further, the microorganism may have an increased activity of converting alpha-ketoglutarate to succinic semialdehyde, and an activity of converting succinic semialdehyde to 4-hydroxybutyrate. The microorganism may be a microorganism lacking a metabolic pathway which converts succinic semialdehyde to 4-hydroxybutyrate in a non-genetically engineered state. For example, the microorganism may be a microorganism derived from the genus *Escherichia* or the genus *Corynebacterium*. The microorganism may be *Escherichia coli* or *Corynebacterium glutamicum*. The activity of converting alpha-ketoglutarate to succinic semialdehyde and the increased activity are the same as described above.

The activity of converting succinic semialdehyde to 4-hydroxybutyrate may be attributed to expression of a polynucleotide encoding 4-hydroxybutyrate dehydrogenase (4HBd). The 4-hydroxybutyrate dehydrogenase may be oxidoreductase (EC.1.1.1) using $NAD^+$ or $NADP^+$ as an electron acceptor, for example, an enzyme catalyzing conversion of ketone to hydroxyl or conversion of aldehyde to alcohol. The polynucleotide encoding 4-hydroxybutyrate dehydrogenase may be introduced. The polynucleotide encoding 4-hydroxybutyrate dehydrogenase may be derived from *Porphyromonas gingivalis*. The polynucleotide encoding 4-hydroxybutyrate dehydrogenase may encode an amino acid sequence of SEQ ID NO: 5. The polynucleotide encoding 4-hydroxybutyrate dehydrogenase may have a nucleotide sequence of SEQ ID NO: 6.

Further, the microorganism may have an increased activity of converting alpha-ketoglutarate to succinic semialdehyde, and an activity of converting succinic semialdehyde to 4-hydroxybutyrate and an activity of converting 4-hydroxybutyrate to 1,4-butanediol. The microorganism may be a microorganism lacking a metabolic pathway which converts succinic semialdehyde to 4-hydroxybutyrate and/or a metabolic pathway which converts 4-hydroxybutyrate to 1,4-butanediol in a non-genetically engineered state. For example, the microorganism may be a microorganism derived from the genus *Escherichia* or the genus *Corynebacterium*. The microorganism may be *Escherichia coli* or *Corynebacterium glutamicum*. The activity of converting alpha-ketoglutarate to succinic semialdehyde and the increased activity, and the activity of converting succinic semialdehyde to 4-hydroxybutyrate are the same as described above.

The activity of converting 4-hydroxybutyrate to 1,4-butanediol may be attributed to expression of a polypeptide that catalyzes conversion of 4-hydroxybutyrate to 4-hydroxybutyryl-CoA and/or expression of a polypeptide that catalyzes conversion of 4-hydroxybutyryl-CoA to 1,4-butanediol.

The polypeptide that catalyzes conversion of 4-hydroxybutyrate to 4-hydroxybutyryl-CoA may be an enzyme classified as CoA-transferase (EC.2.8.3.a). The polypeptide that catalyzes conversion of 4-hydroxybutyrate to 4-hydroxybutyryl-CoA may be 4-hydroxybutyryl coenzyme A:acetyl coenzyme A transferase (4-hydroxybutyryl CoA:acetyl-CoA transferase: Cat2). The polynucleotide encoding the 4-hydroxybutyryl CoA A:acetyl CoA A transferase may be introduced. The polynucleotide encoding the 4-hydroxybutyryl CoA acetyl CoA transferase may be derived from *Porphyromonas gingivalis*. The polynucleotide encoding the 4-hydroxybutyryl CoA:acetyl CoA transferase may encode an amino acid sequence of SEQ ID NO: 7. The polynucleotide encoding the 4-hydroxybutyryl CoA:acetyl CoA transferase may have a nucleotide sequence of SEQ ID NO: 8.

The polynucleotide that catalyzes conversion of 4-hydroxybutyryl-CoA to 1,4-butanediol may be aldehyde dehydrogenase and alcohol dehydrogenase. The aldehyde dehydrogenase and alcohol dehydrogenase may be enzymes that catalyze two-step conversion of acyl-CoA to alcohol. The aldehyde dehydrogenase and alcohol dehydrogenase may convert 4-hydroxybutyryl-CoA to 1,4-BDO via 4-hydroxybutyraldehyde. The aldehyde dehydrogenase includes, for example, butyraldehyde dehydrogenase (Bld). The polynucleotide encoding butyraldehyde dehydrogenase may be derived from *Clostridium saccharoperbutylacetonicum*. The butyraldehyde dehydrogenase may have an amino acid sequence of SEQ ID NO: 9. The polynucleotide encoding butyraldehyde dehydrogenase may have a nucleotide sequence of SEQ ID NO: 10. The polynucleotide encoding alcohol dehydrogenase may be derived from *Clostridium acetobutylicum*. The alcohol dehydrogenase may have an amino acid sequence of SEQ ID NO: 11. The polynucleotide encoding alcohol dehydrogenase may have a nucleotide sequence of SEQ ID NO: 12.

The microorganism may have a deletion or reduction of an activity of converting pyruvate to lactate, an activity of converting pyruvate to formate, an activity of converting acetyl-CoA to ethanol, an activity of converting oxaloacetate to malate, an activity of controlling aerobic respiration, an activity of converting succinic semialdehyde to succinate, or a combination thereof. The term “reduction” may represent the activity of the engineered microorganism relative to that of a non-engineered microorganism. The activity may be reduced by about 75% or more, about 80% or more, about 85% or more, about 90% or more, about 95% or more, or about 100% or more, compared to that of an appropriate control group.

The microorganism may have a deletion or reduction in the expression of a polypeptide converting pyruvate to lactate, a polypeptide converting pyruvate to formate, a polypeptide converting acetyl-CoA to ethanol, a polypeptide converting oxaloacetate to malate, a polypeptide encoding a factor controlling aerobic respiration, a polypeptide converting succinic semialdehyde to succinate, or a combination thereof. The microorganism may have an inactivation or attenuation of a polynucleotide encoding the polypeptide that converts pyruvate to lactate, a polynucleotide encoding the polypeptide that converts pyruvate to formate, a polynucleotide encoding the polypeptide that converts acetyl-CoA to ethanol, a polynucleotide encoding the polypeptide that converts oxaloacetate to malate, a polynucleotide encoding the polypeptide encoding a factor that controls aerobic respiration, a polynucleotide encoding the polypeptide that converts succinic semialdehyde to succinate, or a combination thereof.

The polypeptide that converts pyruvate to lactate may be an enzyme classified as EC.1.1.1.27 or EC.1.1.1.28. The polypeptide that converts pyruvate to lactate may be derived from *Escherichia coli*. The polypeptide may be derived from *Escherichia coli* W chromosome. The gene encoding the polypeptide that converts pyruvate to lactate may have Gene ID of 12753486. The gene may be *Escherichia coli* ldhA encoding NADH-linked lactate dehydrogenase. The ldhA gene may have an amino acid sequence of SEQ ID NO: 13 and a nucleotide sequence of SEQ ID NO: 14.

The polypeptide that converts pyruvate to formate may be an enzyme that reversibly converts pyruvate to formate. The enzyme may catalyze a reaction of pyruvate+CoA↔formate+acetyl CoA. The enzyme may be *Escherichia coli* pyruvate formate lyase (Pfl). The Pfl may be an enzyme classified as EC.2.3.1.54. The gene encoding the polypeptide that converts pyruvate to formate may have Gene ID of 12752499. The gene may be *Escherichia coli* pflB encoding pyruvate formate lyase. The pflB gene may have an amino acid sequence of SEQ ID NO: 15 and a nucleotide sequence of SEQ ID NO: 16.

The polypeptide that converts acetyl-CoA to ethanol may be alcohol dehydrogenase (Adh). The alcohol dehydrogenase may be an enzyme that reversibly converts acetyl CoA to ethanol with oxidation of NADH to $NAD^+$. The alcohol dehydrogenase may be an enzyme classified as EC.1.1.1.1. The gene encoding the polypeptide that converts acetyl-CoA to ethanol may have Gene ID of 12753141. The gene may be *Escherichia coli* adhE encoding NADH-linked alcohol dehydrogenase. The adhE gene may have an amino acid sequence of SEQ ID NO: 17 and a nucleotide sequence of SEQ ID NO: 18.

The polypeptide that converts oxaloacetate to malate may be an enzyme that catalyzes conversion of oxaloacetate to malate with reduction of $NAD^+$ to NADH. The enzyme may be malate dehydrogenase (Mdh). The malate dehydrogenase may be an enzyme classified as EC 1.1.1.37. The gene encoding the polypeptide that converts oxaloacetate to malate may have Gene ID of 12697256. The gene may be *Escherichia coli* mdh encoding NADH-linked malate dehydrogenase. The mdh gene may have an amino acid sequence of SEQ ID NO: 19 and a nucleotide sequence of SEQ ID NO:20.

The polypeptide of the factor that controls aerobic respiration may be ArcA. The ArcA may be a DNA-binding response regulator. The ArcA may be a DNA-binding response regulator of a two-component system. The ArcA is a member of a two-component (ArcB-ArcA) signal transduction system family, and in concert with its cognate sensory kinase ArcB, constitutes a global regulation system that negatively or positively controls the expression of many operons. The ArcA operates under a microaerobic condition to induce the expression of gene products that permit activities of central metabolic enzymes that are sensitive to low oxygen levels. The deletion of arcA/arcB under the microaerobic condition may increase specific activities of genes such as ldh, icd, gltA, mdh, and gdh genes. The arcA gene may have an amino acid sequence of SEQ ID NO: 21 and a nucleotide sequence of SEQ ID NO: 22.

The polypeptide that converts succinic semialdehyde to succinate may be succinate semialdehyde dehydrogenase (Ssadh). The succinate semialdehyde dehydrogenase may be an enzyme that converts succinic semialdehyde to succinate with reduction of $NAD^+$ or $NADP^+$ to NADH or NADPH. The succinate semialdehyde dehydrogenase may be an enzyme classified as EC.1.2.1.24 or EC.1.2.1.16. The gene encoding the polypeptide that converts succinic semialdehyde to succinate may have Gene ID of 12695413 or 12696616. The gene may be *Escherichia coli* sad encoding NAD-linked succinate semialdehyde dehydrogenase and *Escherichia coli* gabD encoding NADP-linked succinate semialdehyde dehydrogenase. The sad gene may have an amino acid sequence of SEQ ID NO: 23 and a nucleotide sequence of SEQ ID NO: 24. The gabD gene may have an amino acid sequence of SEQ ID NO: 25 and a nucleotide sequence of SEQ ID NO: 26.

The microorganism may express a mutant of a foreign pyruvate dehydrogenase subunit, a mutant of NADH insensitive citrate synthase, or a combination thereof.

The foreign pyruvate dehydrogenase subunit may be derived from *Klebsiella pneumonia*. The pyruvate dehydrogenase subunit may be LpdA. LpdA derived from *Klebsiella pneumonia* may have an amino acid sequence of SEQ ID NO: 27. Expression of the foreign pyruvate dehydrogenase subunit may be caused by introduction of a foreign gene. The foreign gene may be lpdA derived from *Klebsiella pneumonia* and have a nucleotide sequence of SEQ ID NO: 28. The mutant of the foreign pyruvate dehydrogenase subunit may have a substitution of Glu with other amino acid at position 354 of SEQ ID NO: 27. Other amino acid may be Lys. The microorganism may include a polynucleotide encoding the mutant of the foreign pyruvate dehydrogenase subunit. The mutant of the foreign pyruvate dehydrogenase subunit may have an amino acid sequence of SEQ ID NO: 29 and a nucleotide sequence of SEQ ID NO: 30.

The NADH insensitive citrate synthase may be GltA. The GltA may have an amino acid sequence of SEQ ID NO: 31 and a nucleotide sequence of SEQ ID NO: 32. The mutant of the NADH insensitive citrate synthase may have a substitution of Arg with other amino acid at position 164 of SEQ ID NO: 31. Other amino acid may be Leu. The microorganism may include a polynucleotide encoding the mutant of the NADH insensitive citrate synthase. The mutant of the citrate synthase may have an amino acid sequence of SEQ ID NO: 33 and a nucleotide sequence of SEQ ID NO: 34.

The microorganism may have an increased activity of converting alpha-ketoglutarate to succinic semialdehyde, in which the increased activity may be caused by increased expression of alpha-ketoglutarate E1 component; an activity of converting succinic semialdehyde to 4-hydroxybutyrate; and a deletion or reduction of an activity of converting pyruvate to lactate, an activity of converting pyruvate to formate, an activity of converting acetyl-CoA to ethanol, an activity of converting oxaloacetate to malate, an activity of controlling aerobic respiration, an activity of converting succinic semialdehyde to succinate, or a combination thereof; and may express the foreign pyruvate dehydrogenase subunit, NADH insensitive citrate synthase, or a combination thereof.

The microorganism may have an increased activity of converting alpha-ketoglutarate to succinic semialdehyde, in which the increased activity may be caused by increased expression of alpha-ketoglutarate E1 component; an activity of converting succinic semialdehyde to 4-hydroxybutyrate and an activity of converting 4-hydroxybutyrate to 1,4-butanediol; and a deletion or reduction of an activity of converting pyruvate to lactate, an activity of converting pyruvate to formate, an activity of converting acetyl-CoA to ethanol, an activity of converting oxaloacetate to malate, an activity of controlling aerobic respiration, an activity of converting succinic semialdehyde to succinate, or a combination thereof; and may express the foreign pyruvate dehydrogenase subunit, NADH insensitive citrate synthase, or a combination thereof.

The increase of each activity, introduction, or deletion, or the introduction for reduction, the inactivated or attenuated polynucleotide is the same as described above.

Another aspect provides a method of producing 4-hydroxybutyrate or 1,4-butanediol, the method including culturing the microorganism; and recovering 4-hydroxybutyrate or 1,4-butanediol from the culture.

The microorganism is the same as described above. The culturing may be fermentation. The fermentation may be fed-batch fermentation and batch separation, fed-batch fermentation and continuous separation, or continuous fermentation and continuous separation.

The culturing of the microorganism may vary according to suitable media and culturing conditions known in the art. The culturing process may be easily adjusted according to a selected microorganism. The culturing method may include one or more cultures selected from the group consisting of a batch culture, a continuous culture, and a fed-batch culture.

A medium used in the culturing may be a medium to satisfy the requirements of a particular microorganism. The medium may be a medium including a carbon source, a nitrogen source, a trace element or a combination thereof.

The carbon source may be carbohydrates, fats, fatty acids, alcohols, organic acids, or a combination thereof. The carbohydrates may be glucose, sucrose, lactose, fructose, maltose, starch, cellulose, or a combination thereof. The fats may be soybean oil, sunflower oil, castor oil, coconut oil, or a combination thereof. The fatty acids may be palmitic acid, stearic acid, linoleic acid, or a combination thereof. The alcohols may be glycerol or ethanol. The organic acids may include acetic acid. The nitrogen source may include organic nitrogen sources, inorganic nitrogen sources, or a combination thereof. The organic nitrogen sources may be peptone, yeast extract, meat extract, malt extract, corn steep liquor (CSL), soybean meal, or a combination thereof. The inorganic nitrogen sources may be urea, ammonium sulfate, ammonium chloride, ammonium phosphate, ammonium carbonate, ammonium nitrate, or a combination thereof. The medium may include phosphorus, metal salts, amino acids, vitamins, precursors, or a combination thereof. The phosphorus sources may include potassium dihydrogen phosphate, dipotassium hydrogen phosphate, or sodium-containing salts corresponding thereto. The metal salts may be magnesium sulfate or iron sulfate.

The medium or individual components constituting the same may be added in the form of a batch culture, a continuous culture, or a fed-batch culture.

In the culturing method, pH of the culture may be adjusted. The adjustment of pH may be performed by adding to the culture, ammonium hydroxide, potassium hydroxide, ammonia, phosphoric acid, or sulfuric acid. Further, the culturing method may include inhibition of foam generation. The inhibition of foam generation may be performed by using an anti-foaming agent. The anti-foaming agent may include fatty acid polyglycol ester. Further, the culturing of the microorganism may be performed under a substantial anaerobic condition. The substantial anaerobic condition means, when the term is used in relation to culture or growth conditions, that the quantity of oxygen in a liquid medium is less than about 10% of the dissolved oxygen saturation. In addition, the substantial anaerobic condition may include a sealed chamber of a liquid or solid medium maintained in oxygen atmosphere less than about 1% oxygen.

In the culturing, the temperature of the culture may be about 20° C. to about 45° C., for example, about 22° C. to about 42° C., or about 25° C. to about 40° C. The culture duration may be extended until a desired amount of 1,4-butanediol production is acquired.

Advantageous Effects of the Invention

A microorganism according to an aspect may have a 4 HB or 1,4-BDO productivity.

According to a method of producing 4HB or 1,4-BDO according to another aspect, 4 HB or 1,4-BDO may be efficiently produced.

MODE OF THE INVENTION

Figure 1:
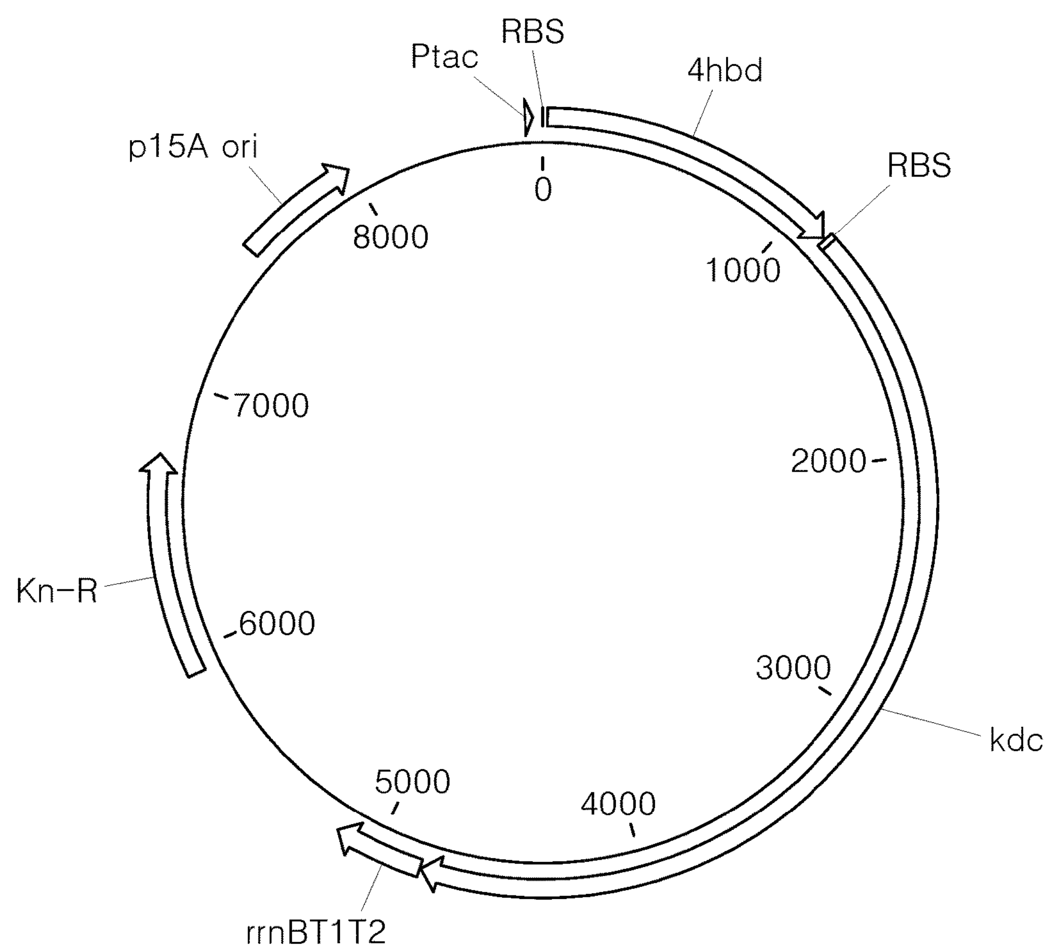
FIG. 1 shows a cleavage map of a pTac15k 4hbd-kdc vector.

Hereinafter, the present invention will be described in more detail with reference to Examples. However, these Examples are for illustrative purposes only, and the scope of the present invention is not intended to be limited by these Examples.

Example 1: Preparation of Microorganism Having 4-Hydroxybutyrate Productivity with Enhanced Alpha-Ketoglutarate Decarboxylase Activity

1.1. Preparation of Microorganism Having Metabolic Pathway Mutated for Prevention of Byproduct (Lactate, Formate, Ethanol, and Succinate) Production and for Cell Growth and Carbon Source Consumption Under Anaerobic Conditions

1.1.1. Deletion of ldhA, pflB, adhE, Mdh, arcA, Sad, and gabD Genes

In *Escherichia* W (ATCC 9637), ldhA, pflB, adhE, mdh, arcA, sad, and gabD genes were deleted by using a one-step inactivation method [Warner et al., PNAS, 6; 97(12):6640-6645, 2000; lee, K. H. et al., Molecular systems biology 3, 149, 2007].

To delete the ldhA gene, PCR was performed with primers of SEQ ID NOS: 35 and 36 using a pMloxC vector [lee, K. H. et al., Molecular systems biology 3, 149, 2007] as a template. The obtained DNA fragment was electroporated to competent cells of the W strain, in which lamda-red recombinase (λ-red recombinase) was expressed, to prepare a mutant strain in which the ldhA gene was deleted. To verify deletion of the ldhA gene, a colony PCR was performed with primers of SEQ ID NOS: 37 and 38. As a result, *Escherichia coli* W ΔldhA was obtained.

Further, in the same manner as described above, a PCR fragment obtained with primers of SEQ ID NOS: 39 and 40 was introduced to prepare a mutant strain in which the pflB gene was deleted. To verify deletion of the pflB gene, primers of SEQ ID NOS: 41 and 42 were used. As a result, *Escherichia coli* W ΔldhAΔpflB was obtained.

Further, in the same manner as described above, a PCR fragment obtained with primers of SEQ ID NOS: 43 and 44 was introduced to prepare a mutant strain in which the adhE gene was deleted. To verify deletion of the adhE gene, primers of SEQ ID NOS: 45 and 46 were used. As a result, *Escherichia coli* W ΔldhAΔpflBΔadhE was obtained.

Further, in the same manner as described above, a PCR fragment obtained with primers of SEQ ID NOS: 47 and 48 was introduced to prepare a mutant strain in which the mdh gene was deleted. To verify deletion of the mdh gene, primers of SEQ ID NOS: 49 and 50 were used. As a result, *Escherichia coli* W ΔldhAΔpflBΔadhEΔmdh was obtained.

Further, in the same manner as described above, a PCR fragment obtained with primers of SEQ ID NOS: 51 and 52 was introduced to prepare a mutant strain in which the arcA gene was deleted. To verify deletion of the arcA gene, primers of SEQ ID NOS: 53 and 54 were used. As a result, *Escherichia coli* W ΔldhAΔpflBΔadhEΔmdhΔarcA was obtained.

Further, in the same manner as described above, a PCR fragment obtained with primers of SEQ ID NOS: 55 and 56 was introduced to prepare a mutant strain in which the sad gene was deleted. To verify deletion of the sad gene, primers of SEQ ID NOS: 57 and 58 were used. As a result, *Escherichia coli* W ΔldhAΔpflBΔadhEΔmdhAarcAΔsad was obtained.

Further, in the same manner as described above, a PCR fragment obtained with primers of SEQ ID NOS: 59 and 60 was introduced to prepare a mutant strain in which the gabD gene was deleted. To verify deletion of the gabD gene, primers of SEQ ID NOS: 61 and 62 were used. As a result, *Escherichia coli* W ΔldhAΔpflBΔadhEΔmdhΔarcAΔsadΔgabD was obtained.

1.1.2. Substitution of *Escherichia coli* lpdA Gene with *Klebsiella Pneumonia*-Derived lpdA Gene Mutant In *Escherichia coli* W ΔldhAΔpflBΔadhEΔmdhΔarcAΔsadΔgabD strain, the 1pdA gene of *Escherichia coli* was substituted with a *Klebsiella Pneumonia*-derived 1pdA gene mutant by the one-step inactivation method.

The *Klebsiella pneumonia*-derived 1pdA gene mutant, K.1pdA(E354K) was obtained by site-directed mutagenesis using the primers of SEQ ID NOS: 63 and 64. PCR was performed using a pSacHR06 vector [US Patent Publication No. 2013-0164805] as a template and primers of SEQ ID NOS: 65 and 66. The obtained DNA fragment was electroporated to competent cells of the W strain, in which λ-red recombinase was expressed, to substitute the IpdA gene with a sacB-Km cassette.

Thereafter, PCR was performed using the obtained *Klebsiella Pneumonia*-derived lpdA gene mutant, K.lpdA (E354K) as a template and primers of SEQ ID NOS: 67 and 68, and the one-step inactivation was further performed to substitute the part, in which the 1pdA gene had been substituted with the sacB-Km cassette, with K.lpdA (E354K). To verify the substituted gene, a colony PCR was performed with the primers of SEQ ID NOS: 69 and 70. As a result, *Escherichia coli* W ΔldhAΔpflBΔadhEΔmdhΔarcAΔsadΔgabD ΔlpdA::K.lpdA (E354K) was obtained.

1.1.3. Introduction of *Escherichia coli* gltA Gene Mutant

In the *Escherichia coli* W ΔldhAΔpflBΔadhEΔmdhΔarcAΔsadΔgabD ΔlpdA::K.lpdA (E354K) strain, gltA(R164L), an *Escherichia coli* gltA gene mutant, was introduced by the one step inactivation method.

The *Escherichia coli* gltA gene mutant, gltA(R164L) was prepared by site-directed mutagenesis using the primers of SEQ ID NOS: 71 and 72. PCR was performed using a pSacHR06 vector as a template and primers of SEQ ID NOS: 73 and 74. The obtained DNA fragment was electroporated to competent cells of the W strain, in which λ-red recombinase was expressed, to substitute the gltA gene with the sacB-Km cassette. Thereafter, PCR was performed using the obtained *Escherichia coli* gltA gene mutant, gltA (R164L) as a template and primers of SEQ ID NOS: 75 and 76, and the one-step inactivation was further performed to substitute the part, in which the gltA gene had been substituted with the sacB-Km cassette, with gltA(R164L). To verify the substituted gene, a colony PCR was performed with the primers of SEQ ID NOS: 77 and 78. The genotype of the *Escherichia coli* W-derived mutant strain prepared by the above-described method was W ΔldhAΔpflBΔadhEΔmdhΔarcAΔsadΔgabD ΔlpdA::K.lpdA (E354K) gltA(R164L), which was designated as W026.

1.2. Preparation of 4HBd and Kdc Expression Vector

Vectors to express each of 4 types of alpha-ketoglutarate decarboxylase (kdc) genes together with the 4-hydroxybutyrate dehydrogenase (4hbd) gene were prepared. The kdc gene is also called sucA or kgd gene depending on microorganisms.

*Porphyromonas gingivalis* (*P. gingivalis*)—derived 4hbd gene, *mycobacterium bovis* (*M. bovis*)—derived sucA gene, and *euglena gracilis* (*E. gracilis*)—derived sucA gene were synthesized by optimizing the known sequences thereof to *Escherichia coli* codons (COSMO GENETECH CO., LTD. Korea). The *Porphyromonas gingivalis*-derived 4hbd gene has an amino acid sequence of SEQ ID NO: 79 and a nucleotide sequence of SEQ ID NO: 80. The *mycobacterium bovis*-derived sucA gene has an amino acid sequence of SEQ ID NO: 81 and a nucleotide sequence of SEQ ID NO: 82. The *euglena gracilis*-derived sucA gene has an amino acid sequence of SEQ ID NO: 83 and a nucleotide sequence of SEQ ID NO: 84.

The obtained 4hbd gene was introduced into a pTac15k [Qian, Z.-G. et al., Biotechnol. Bioeng. 104(4):651-662 (2009)] using restriction enzymes SacI and XbaI to prepare a pTac15k 4hbd vector. The pTac15k 4hbd vector was digested with restriction enzyme XbaI, and then used as a vector DNA fragment, and *M. bovis*-derived sucA amplified by PCR with SEQ ID NOS: 85 and 86, *E. gracilis*-derived sucA amplified by PCR with SEQ ID NOS: 87 and 88, *Escherichia coli*-derived sucA amplified by PCR with SEQ ID NOS: 89 and 90, and *C. glutamicum*-derived kgd amplified by PCR with SEQ ID NOS: 91 and 92 were used as insert DNA fragments, respectively. They were ligated to each other using an InFusion Cloning Kit (Clontech Laboratories, Inc., USA) to prepare 4 types of pTac15k 4hbd-kdc vectors, namely, pTac15k 4hbd-MbosucA, pTac15k 4hbd-EglsucA, pTac15k 4hbd-EcosucA, and pTac15k 4hbd-Cglkgd, respectively. In this regard, *Escherichia coli*-derived sucA gene (SEQ ID NOS: 1 and 2) and *Corynebacterium glutamicum* (*C. glutamicum*)-derived kgd gene (NCgl1084) (SEQ ID NO: 3 and 4) were used obtained by PCR using genomic DNA of each microorganism as a template.

FIG. 1 shows a cleavage map of the pTac15k 4hbd-kdc vector.

1.3. Introduction of 4hbd and kdc Genes

Each of the 4 types of pTac15k 4hbd-kdc vectors prepared in Example 1.2 was introduced into *Escherichia coli* W—derived mutant strain W026 prepared in Example 1.1 by a heat shock method (Sambrook, J & Russell, D. W., New York: Cold Spring Harbor Laboratory Press, 2001) to prepare strains having 4HB productivity. The transformed strains were obtained by selection on LB plates containing 50 μg/mL of kanamycin.

As a result, recombinant microorganisms, *E. coli* W026 (pTac15k 4hbd-MboBCGsucA), *E. coli* W026 (pTac15k 4hbd-EglsucA), *E. coli* W026 (pTac15k 4hbd-EcosucA), and *E. coli* W026 (pTac15k 4hbd-Cglkgd) were obtained. Further, *E. coli* W026 (pTac15k 4hbd) was prepared and used as a control to compare 4HB production in the following Example.

Example 2: Production of 4-Hydroxybutyrate Using Microorganisms Prepared in Example 1

The microorganisms prepared in Example 1 and W026 containing no expression vector and W026 (pTac15k 4hbd) as control groups were inoculated in 10 mL of LB medium containing 50 μg/mL kanamycin, and pre-culture was performed at 30° C. for 12 hours. W026 containing no expression vector was cultured in a medium containing no kanamycin.

Thereafter, each 0.3 mL of the pre-cultures was inoculated to a 125-mL flask containing 30 mL of MR medium containing 20 g/L glucose, 1 g/L yeast extract, 100 mM MOPS, 10 mM $NaHCO_3$, and 50 μg/mL kanamycin, and cultured at 30° C. for 24 hours under shaking at 220 rpm. The MR medium had components of 6.67 g of $KH_2PO_4$, 4 g of $(NH_4)_2HPO_4$, 0.8 g of citric acid, 0.8 g of $MgSO_4.7H_2O$, and 5 mL of a trace metal solution (containing 10 g of $FeSO_4.7H_2O$, 1.35 g of $CaCl_2$, 2.25 g of $ZnSO_4$. $7H_2O$, 0.5 g of $MnSO_4.4H_2O$, 1 g of $CuSO_4$. $5H_2O$, 0.106 g of $(NH_4)_6Mo_7O_{24}$. $4H_2O$, 0.23 g of $Na_2B_4O_7.10H_2O$, and 10 mL of 35% HCl per 1 L of distilled water) per 1 L of distilled water, and pH was adjusted to 7.0 using 10 N NaOH. To induce expression of the introduced genes, the microorganisms were cultured until $OD_{600}$ reached 0.5. When $OD_{600}$ reached 0.5, 0.25 mM IPTG was added to the medium.

The produced 4HB was analyzed in the following method: 1 ml was taken from 30 ml of the medium, and centrifuged at 13000 rpm for 30 minutes. A supernatant was centrifuged once again under the same conditions, and a sample was prepared by filtering 800 μl of the supernatant with a 0.45 μm filter. 10 μl of the sample was analyzed by UHPLC (Ultra High Performance Liquid Chromatography, Water) to measure the quantity of 1,4-BDO. UHPLC was Agilent 1100 equipment employing a refractive index detector (RID). 4 mM $H_2SO_4$ solution was used as a mobile phase, a BIO-RAD Aminex HPX-87H Column was used as a stationary phase, and a flow rate was 0.7 ml/min. The temperature of both the column and the detector was 50° C.

Figure 2:
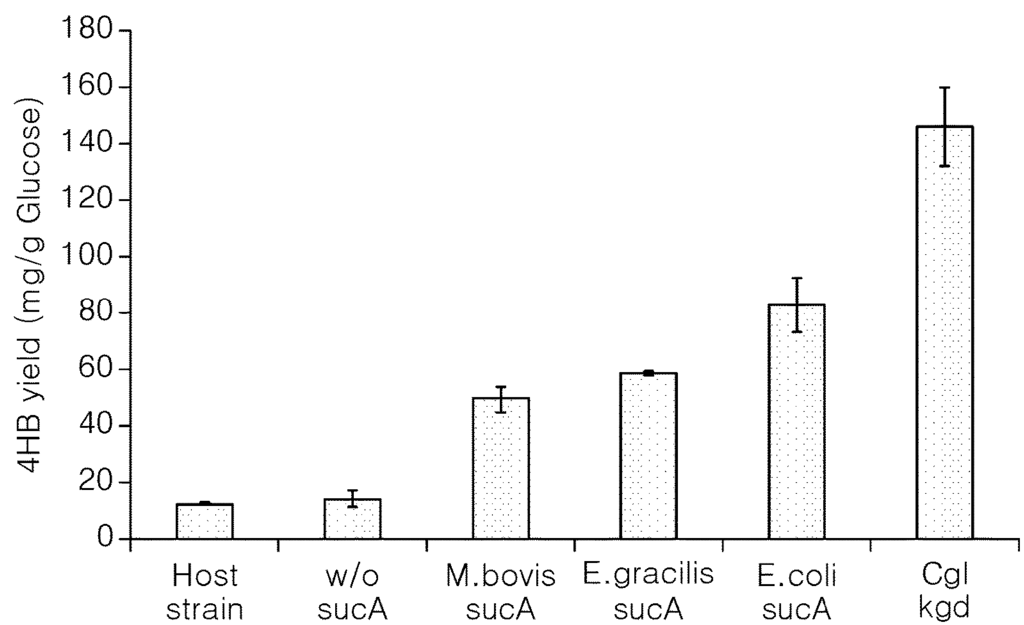
FIG. 2 shows the results of measuring 4HB production by culturing *Escherichia coli* introduced with one of 4 types of alpha-ketoglutarate decarboxylase (kdc) genes and 4-hydroxybutyrate dehydrogenase (4hbd) gene, and *Escherichia coli* introduced with no kdc gene.

FIG. 2 shows the results of measuring 4HB production by culturing *Escherichia coli* introduced with one of 4 types of alpha-ketoglutarate decarboxylase (kdc) genes and 4-hydroxybutyrate dehydrogenase (4hbd) gene, and *Escherichia coli* introduced with no kdc gene;

As a result, *Escherichia coli* introduced with *E. gracilis*-derived sucA showed 1.2-fold increase in 4HB productivity, compared to *Escherichia coli* introduced with *M. bovis*-derived sucA. Further, it was first confirmed that 4HB was produced in *Escherichia coli* introduced with *E. coli*-derived sucA or *C. glutamicum*—derived kgd, showing 1.7- or 2.9-fold increase in 4HB productivity, compared to *Escherichia coli* introduced with *M. bovis*-derived sucA, respectively.

Example 3: Preparation of Microorganism Having 1,4-Butanediol (1,4-BDO) Productivity with Enhanced Alpha-Ketoglutarate Decarboxylase Activity 3.1. Preparation of Cat2 and Bld Expression Vector To construct a production pathway of 1,4-BDO from 4HB, a vector for expression of 4-hydroxybutyryl CoA: acetyl CoA transferase(cat2) and butyraldehyde dehydrogenase(bld) genes was prepared.

*Porphyromonas Gingivalis*-derived cat2 gene of SEQ ID NOS: 7 and 8 was synthesized (COSMO GENETECH CO., LTD. Korea). The obtained cat2 gene was introduced into pTrc99a (manufactured by AP Biotech) using restriction enzymes, EcoRI and HindIII to prepare pTrc99a cat2.

PCR was performed using gDNA of *Clostridium saccharoperbutylacetonicum* as a template and primer sequences of SEQ ID NOS: 61 and 62 to amplify butyraldehyde dehydrogenase gene of SEQ ID NOS: 9 and 10. The obtained butyraldehyde dehydrogenase gene was inserted into the pTrc99a cat2 vector using restriction enzymes, NcoI/EcoR to prepare pTrc99a bld-cat2. In this regard, the used Bld gene is a mutant having increased activity, and is bldI (M227L) gene having an amino acid sequence of SEQ ID NO: 93 and a nucleotide sequence of SEQ ID NO: 94.

Figure 3:
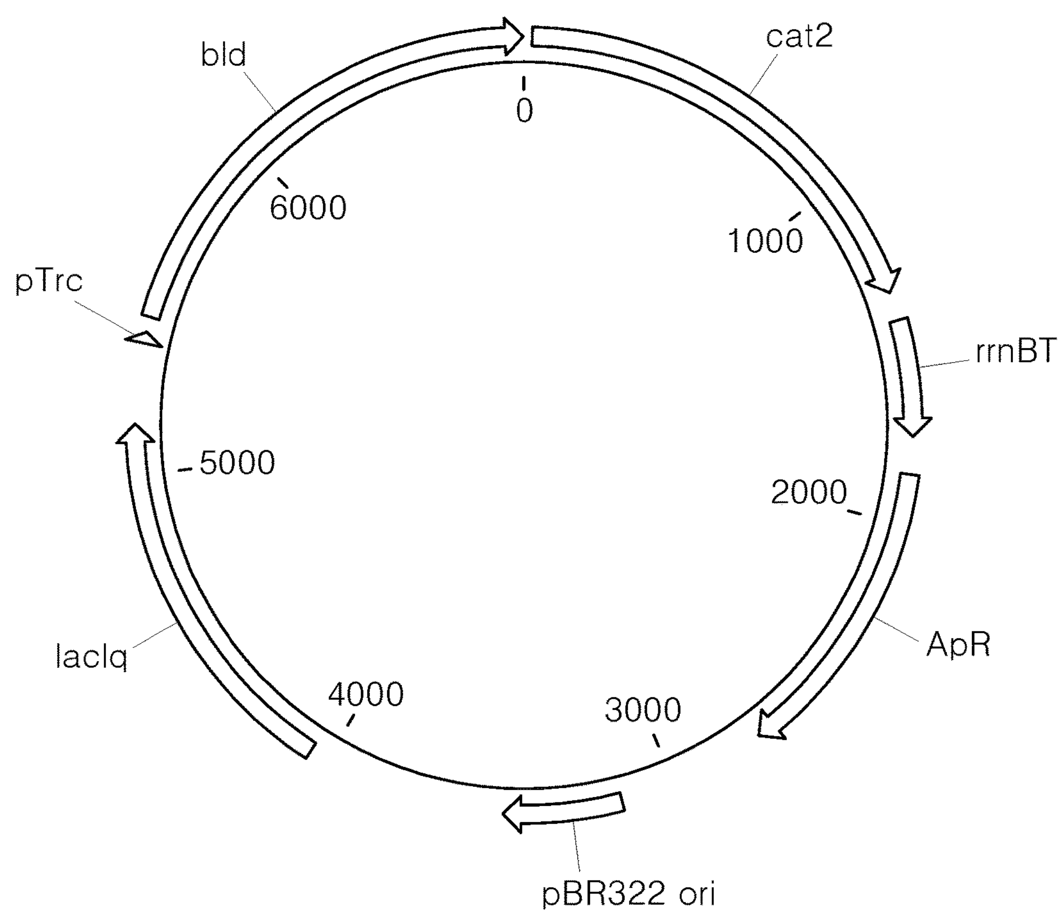
FIG. 3 shows a cleavage map of a pTac99a bld-cat2 vector.

FIG. 3 shows a cleavage map of the pTac99a bld-cat2 vector.

3.2. Introduction of cat2 and bld Genes

The pTac99a bld-cat2 vector prepared in Example 3.1 was introduced into each of the microorganisms prepared in Example 1 by the heat shock method to prepare strains having 1,4-BDO productivity. The transformed strains were obtained by selection on an LB plate containing 50 μg/mL of kanamycin and 100 μg/mL of ampicillin.

As a result, recombinant microorganisms, *E. coli* W026 (pTac15k 4hbd-MboBCGsucA+pTrc99a bld-cat2), *E. coli* W026 (pTac15k 4hbd-EglsucA+pTrc99a bld-cat2), *E. coli* W026 (pTac15k 4hbd-EcosucA+pTrc99a bld-cat2), and *E. coli* W026 (pTac15k 4hbd-Cglkgd+pTrc99a bld-cat2) were obtained. Further, *E. coli* W026 (pTac15k+pTrc99a bld-cat2) and W026 (pTac15k 4hbd+pTrc99a bld-cat2) were prepared and used as controls to compare 1,4-BDO production in the following Example.

Example 4: Production of 1,4-Butanediol using Microorganisms Prepared in Example 3

Each of the microorganisms prepared in Example 3, and W026 (pTac15k+pTrc99a bld-cat2) and W026 (pTac15k 4hbd+pTrc99a bld-cat2) as control groups were inoculated in 10 mL of LB medium containing 50 μg/mL kanamycin and 100 μg/mL of ampicillin, and pre-culture was performed at 30° C. for 12 hours.

Thereafter, in the same manner as in Example 2, the microorganisms were cultured for 24 hours under shaking, and the quantity of produced 1,4-BDO was measured. 1,4-BDO was analyzed by the same method as in the 4HB analysis of Example 2.

Figure 4:
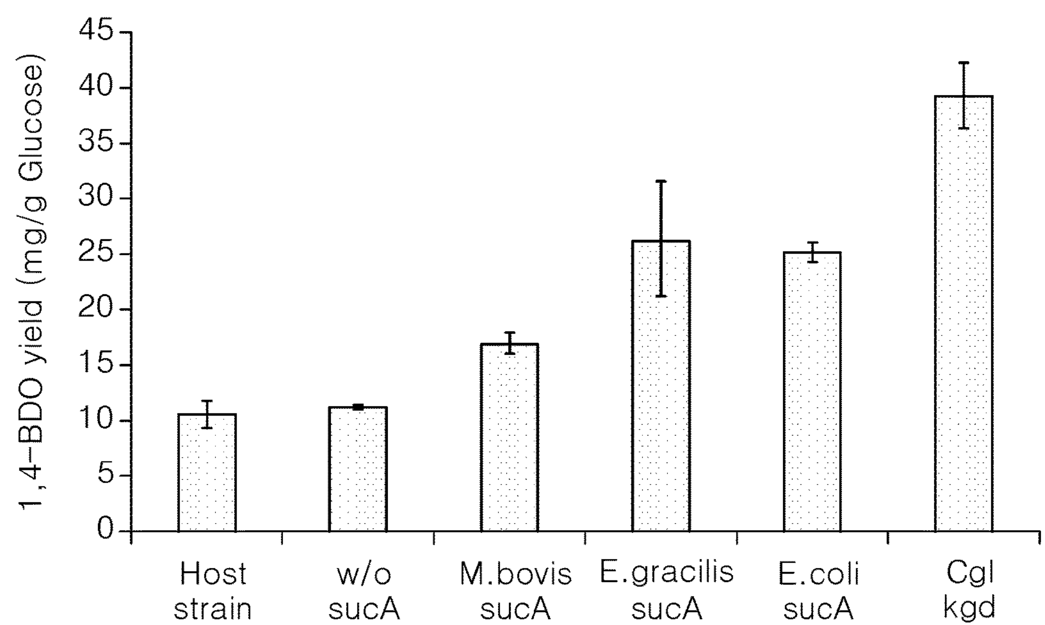
FIG. 4 shows the results of measuring 1,4-BDO production by culturing *Escherichia coli* introduced with one of 4 types of kdc genes, 4hbd gene, cat2 gene and bld gene, and *Escherichia coli* introduced with no kdc gene.

FIG. 4 shows the results of measuring 1,4-BDO production by culturing *Escherichia coli* introduced with one of 4 types of kdc genes, 4hbd gene, cat2 gene and bld gene, and *Escherichia coli* introduced with no kdc gene.

As a result, *Escherichia coli* introduced with *E. gracilis*-derived sucA showed 1.5-fold increase in 1,4-BDO productivity, compared to *Escherichia coli* introduced with *M.*

Bovis-derived sucA. Further, it was first confirmed that 1,4-BDO was produced in *Escherichia coli* introduced with *E. coli*-derived sucA or *C. glutamicum*—derived kgd, showing 1.5- or 2.3-fold increase in 1,4-BOD productivity, compared to *Escherichia coli* introduced with *M. bovis*-derived sucA, respectively.

The invention claimed is:

1. A method of producing 4-hydroxybutyrate or 1,4-butanediol, the method comprising:

culturing an *Escherichia coli* (*E. coli*) microorganism comprising an exogenous polynucleotide encoding an *E. coli* alpha-ketoglutarate dehydrogenase E1 component, a *Corynebacterium glutamicum* alpha-ketoglutarate dehydrogenase E1 component, or a *Euglena gracilis* alpha-ketoglutarate dehydrogenase E1 component; and recovering 4-hydroxybutyrate or 1,4-butanediol from the culture.

2. The method of claim 1, wherein the culturing is performed under anaerobic conditions.

3. The method of claim 1, wherein the microorganism comprises an exogenous polynucleotide encoding an endogenous alpha-ketoglutarate dehydrogenase E1 component.

4. The method of claim 1, wherein the alpha-ketoglutarate dehydrogenase E1 component has an amino acid sequence of SEQ ID NO: 1 or 3.

5. The method of claim 1, wherein the polynucleotide encoding the alpha-ketoglutarate dehydrogenase E1 component has a nucleotide sequence of SEQ ID NO: 2 or SEQ ID NO: 4.

6. The method of claim 1, wherein the microorganism converts succinic semi-aldehyde to 4-hydroxybutyrate.

7. The method of claim 6, wherein the microorganism expresses 4-hydroxybutyrate dehydrogenase that converts succinic semi-aldehyde to 4-hydroxybutyrate.

8. The method of claim 7, wherein the 4-hydroxybutyrate dehydrogenase comprises the amino acid sequence of SEQ ID NO: 5.

9. The method of claim 1, wherein the microorganism converts succinic semi-aldehyde to 4-hydroxybutyrate and converts 4-hydroxybutyrate to 1,4-butanediol.

10. The method of claim 9, wherein the microorganism expresses 4-hydroxybutyrate dehydrogenase, and expresses 4-hydroxybutyryl coenzyme A:acetyl coenzyme A transferase, aldehyde dehydrogenase, and alcohol dehydrogenase, which converts 4-hydroxybutyrate to 1,4-butanediol.

11. The method of claim 10, wherein the 4-hydroxybutyrate dehydrogenase, 4-hydroxybutyryl coenzyme A:acetyl coenzyme A transferase, the aldehyde dehydrogenase, and alcohol dehydrogenase comprise amino acid sequences of SEQ ID NOS: 5, 7, 9, and 11, respectively.

12. The method of claim 1, wherein an enzyme classified as EC.1.1.1.27 or EC.1.1.1.28 that converts pyruvate to lactate, an enzyme classified as EC.2.3.1.54 that converts pyruvate to formate, an enzyme classified as EC.1.1.1.1 that converts acetyl CoA to ethanol, an enzyme classified as 1.1.1.37 that converts oxaloacetate to malate, ArcA, an enzyme classified as EC.1.2.1.24 or EC.1.2.1.16 that converts succinic semi-aldehyde to succinate, or a combination thereof is removed or reduced in the microorganism.

13. The method of claim 12, wherein a polynucleotide encoding an enzyme classified as EC.1.1.1.27 or EC.1.1.1.28 that converts pyruvate to lactate, a polynucleotide encoding an enzyme classified as EC.2.3.1.54 that converts pyruvate to formate, a polynucleotide encoding an enzyme classified as EC.1.1.1.1 that converts acetyl CoA to ethanol, a polynucleotide encoding an enzyme classified as 1.1.1.37 that converts oxaloacetate to malate, a polynucleotide encoding ArcA, a polynucleotide encoding an enzyme classified as EC.1.2.1.24 or EC.1.2.1.16 that converts succinic semi-aldehyde to succinate, or a combination thereof is inactivated or attenuated in the microorganism.

14. The method of claim 1, wherein the microorganism expresses a foreign pyruvate dehydrogenase subunit mutant, a NADH-insensitive citrate synthase mutant, or a combination thereof.

* * * * *